Figure 1:
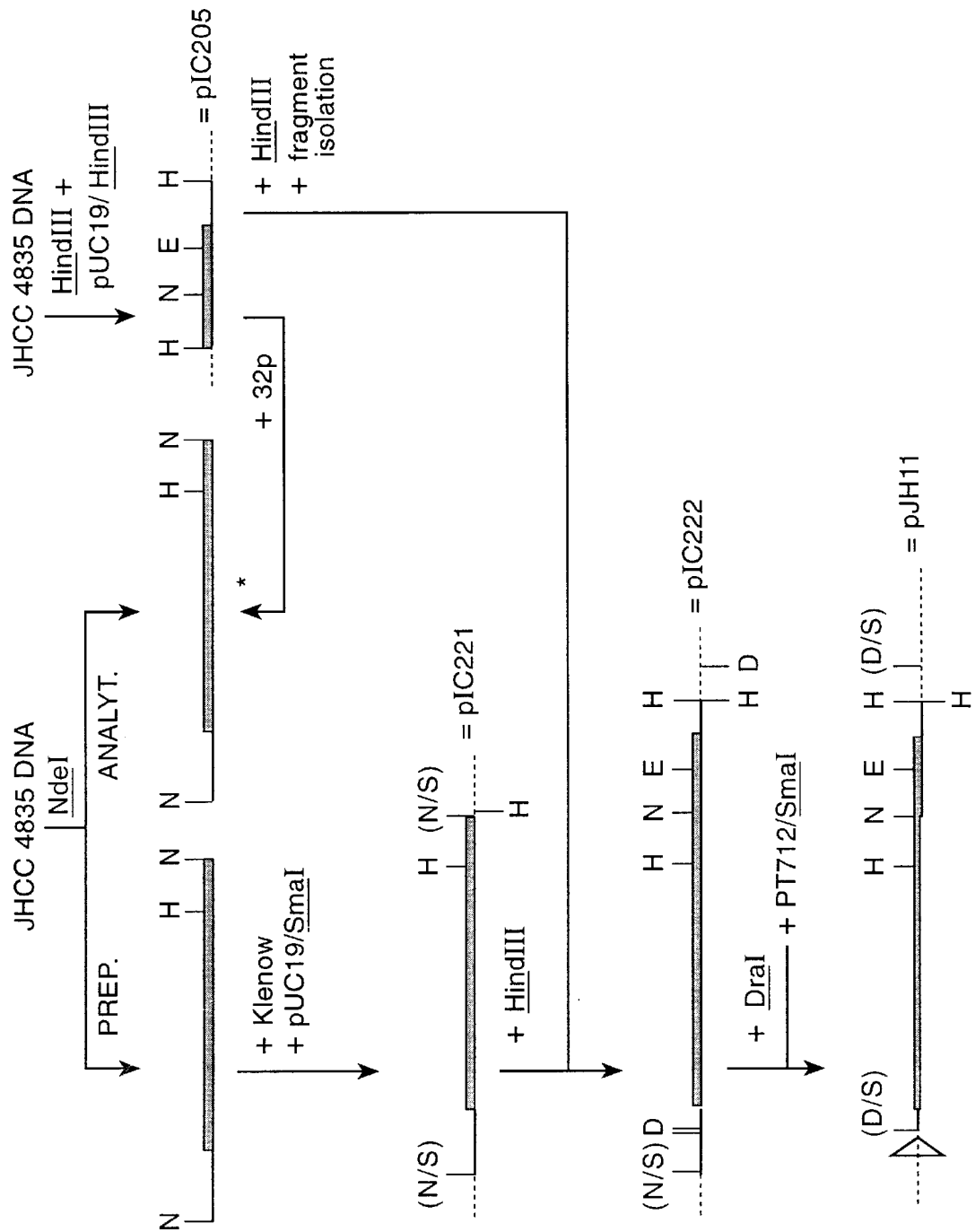
Figure 2:
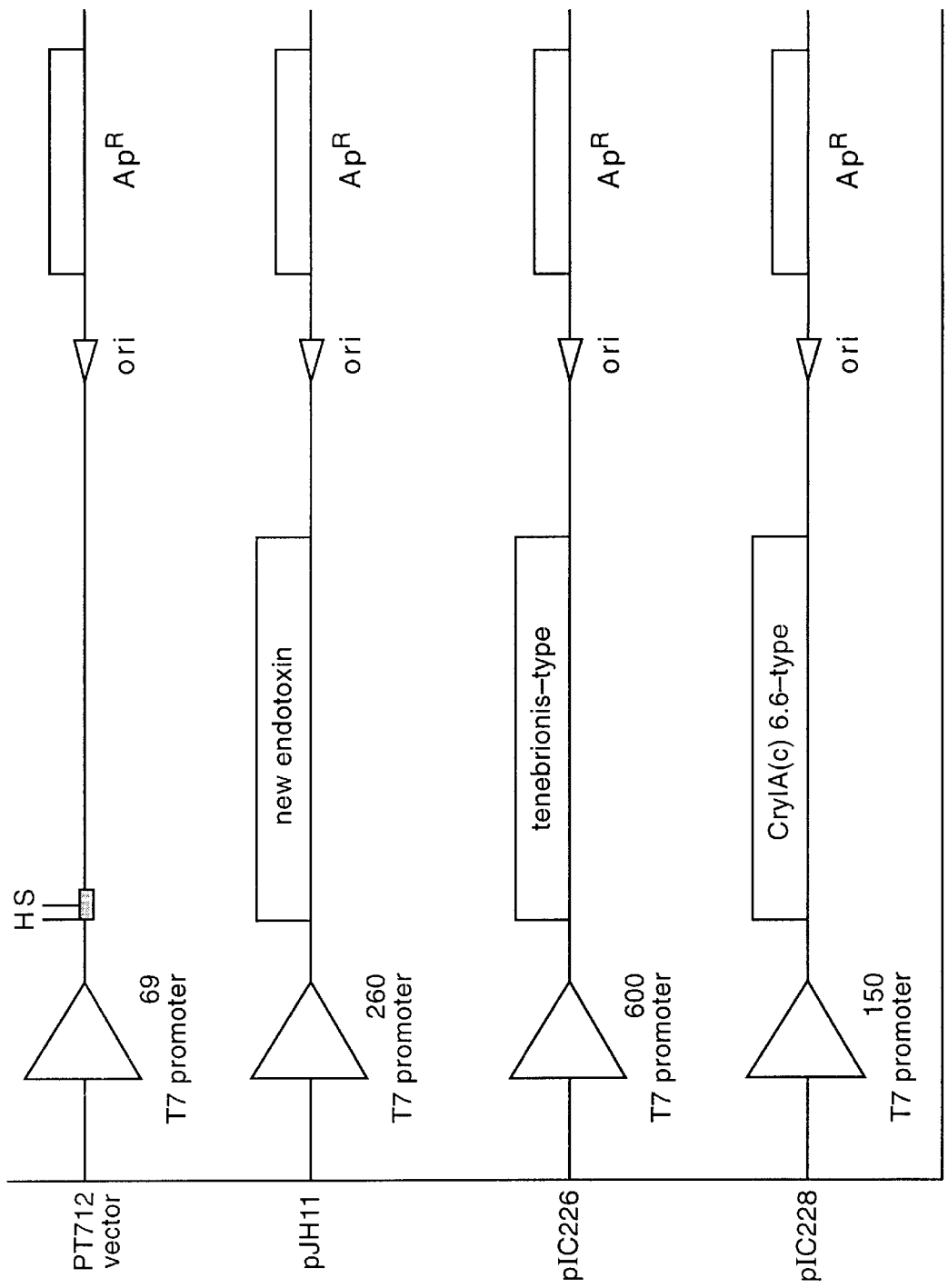
Figure 3:
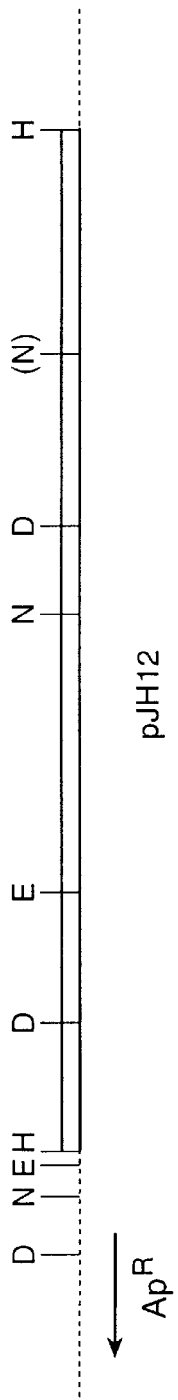

United States Patent [19]
Ely et al.

[11] Patent Number: 6,063,605
[45] Date of Patent: May 16, 2000

[54] *BACILLUS THURINGIENSIS* ENDOTOXIN GENES AND METHODS OF USE

[75] Inventors: Susan Ely, North Lansing, N.Y.; Ravindra Haribhai Tailor, Bracknell, United Kingdom; Janet Mary Tippett; Bruce Marvin Held, both of Ames, Iowa; Robert Gerard Blenk, deceased, late of Raleigh, N.C., by Muriel R. Blenk, executor

[73] Assignee: Zeneca Limited, London, United Kingdom

[21] Appl. No.: 08/286,870

[22] Filed: Aug. 5, 1994

Related U.S. Application Data

[63] Continuation-in-part of application No. 07/520,228, May 9, 1990, Pat. No. 5,573,766.

[30] Foreign Application Priority Data

May 9, 1989 [GB] United Kingdom ............... 8910624

[51] Int. Cl.$^7$ ............................. C12N 15/32; C12N 15/75
[52] U.S. Cl. .............. 435/172.3; 435/69.1; 435/240.1; 435/252.31; 435/252.33; 435/320.1; 536/23.71; 424/93.2
[58] Field of Search ................................ 435/69.1, 172.3, 435/320.1, 252.3, 240.1, 240.2, 252.31, 252.33; 536/23.71, 23.1; 514/2; 424/93.7, 93.461, 93.2

[56] References Cited

FOREIGN PATENT DOCUMENTS 0 202 739 11/1986 European Pat. Off. .
0 238 311 9/1987 European Pat. Off. .

OTHER PUBLICATIONS

Chambers, Judith A., Amy Jelen, M. Pearce Gilbert, Christine S. Jany, Timothy B. Johnson, and Cynthia Gawron--Burke. Isolation and Characterization of a Novel Insecticidal Crystal Protein Gene from *Bacillus thuringiensis* subsp. *aizawai*, p. 3966–3976. Journal of Bacteriology, vol. 173, No. 13. Langhorne, Pennsyvania. 1991.

Gleave, Andrew P., Ruth Williams, and Rebecca J. Hedges. Screening by Polymerase Chain Reaction of *Bacillus thuringiensis* Serotypes for the Present of cryV–Like Insecticidal Protein Genes and Characterization of a cryV Gene Cloned from *B. thuringiensis* subsp. *kurstaki*, p. 1683–1687. Applied and Environmental Microbiology, vol. 59, No. 5. Auckland, New Zealand. 1993.

*Primary Examiner*—John L. LeGuyader
*Attorney, Agent, or Firm*—Cushman Darby & Cushman Intellectual Property Group of Pillsbury Madison & Sutro LLP

[57] ABSTRACT

Novel strains of the insecticidal microorganism *Bacillus thurinaiensis* are described. These contain novel genes, and in particular a gene coding for a novel insecticidal endotoxin, 81 kilodaltons in length, toxic to both Lepidoptera and Coleoptera. The novel strains and the genes they contain may be used to combat insect attack against plants.

29 Claims, 57 Drawing Sheets

FIG. 5A

```
                                                  N        M                                                    C  T
                                                  D        S                                       H            L  A
                                                  E        E                                       P            A  Q
                                                  1        1                                       H            1  1
CAT ATG TAT AGA GCA ACT TAA TCA AGC AGA GAT ATT TTC ACC TAT CGA                                                         48
His Met Tyr Arg Ala Thr Ter Ser Ser Arg Asp Ile Phe Thr Tyr Arg
 1            5                  10                  15

A
                                        T
                                        Q
                                        1
TGA AAA TAT CTC TGC TTT TTC TTT TAT TTG GTA TAT GCT TTA CTT                                                              96
Ter Lys Tyr Leu Cys Phe Phe Phe Tyr Leu Val Tyr Ala Leu Leu
            20                  25                  30

GTA ATC GAA AAT AAA GCA CTA ATA AGA GTA TTT ATA GGT GTT TGA AGT                                                         144
Val Ile Glu Asn Lys Ala Leu Ile Arg Val Phe Ile Gly Val Ter Ser
            35                  40                  45
```

FIG. 5B

```
                            MD          MD      M       M
                            SR          SR      A       S
                            EA          EA      E       E
                            11          11      2       1
TAT TTC AGT TCA TTT TTA AAG AAG GTT TAA AGA CGT TAG AAA GTT ATT    192
Tyr Phe Ser Ser Phe Leu Lys Lys Val Ter Arg Arg Ter Lys Val Ile
 50                  55                  60

A M
        S                                                   S S
        S                                                   E E
        P                                                   1 1
        1                                                    /
AAG GAA TAA TAT TTA TTA GTA AAT TCC ACA TAT ATT ATA TAA TTA ATT    240
Lys Glu Ter Tyr Leu Leu Val Asn Ser Thr Tyr Ile Ile Ter Leu Ile
 65                  70                  75                  80

A D
                                                            L D
                                                            U E
                                                            1 1
ATG AAA TAT ATG TAT AAA TTG AAA ATG CTT TAT TTG ACA TTA CAG CTA    288
Met Lys Tyr Met Tyr Lys Leu Lys Met Leu Tyr Leu Thr Leu Gln Leu
                 85                  90                  95
```

FIG. 5C

```
                                                         M
                                                         N
                                                         L
                                                         1
                        M
                        S
                        E
                        1
AGT ATA ATT TTG TAT GAA TAA AAT TAT ATC TGA AAA TTA AAT AAT AGT    336
Ser Ile Ile Leu Tyr Glu Ter Asn Tyr Ile Ter Lys Leu Asn Asn Ser
             100             105             110

S   A M               H
        B   S S               N
        O   E E               F
        1   1 1               1
              /
ATA AGT GGA GGG ATT AAT ATG AAA CTA AAG AAT CAA GAT AAG CAT CAA    384
Ile Ser Gly Gly Ile Asn Met Lys Leu Lys Asn Gln Asp Lys His Gln
             115             120             125

M                                                    H
    A                                                    N
    E                                                    F
    1                                                    1
S
F
A
N
AGT TTT TCT AGC AAT GCG AAA GTA GAT AAA ATC TCT ACG GAT TCA CTA    432
Ser Phe Ser Asn Ala Lys Val Asp Lys Ile Ser Thr Asp Ser Leu
             130             135             140
```

FIG. 5D

```
                                                          AM    B     N
                                                          SS    S     L
                                                          EE    P     A
                                                          11    H     3
                                                          /
AAA AAT GAA ACA GAT ATA GAA TTA CAA AAC ATT AAT CAT GAA GAT TGT    480
Lys Asn Glu Thr Asp Ile Glu Leu Gln Asn Ile Asn His Glu Asp Cys
145                 150                 155                 160

M           D
    B           D
    O           E
    2           1
                /
TTG AAA ATG TCT GAG TAT GAA AAT GTA GAG CCG TTT GTT AGT GCA TCA    528
Leu Lys Met Ser Glu Tyr Glu Asn Val Glu Pro Phe Val Ser Ala Ser
            165                 170                 175

BAN  RKS  ASN
    S                                       ASL  SPT  WEA
    F                                       NPA  ANY  RCE
    A                                       114  111  211
    N                                       /    /    ///
ACA ATT CAA ACA GGT ATT GGT ATT GCG GGT AAA ATA CTT GGT ACC CTA    576
Thr Ile Gln Thr Gly Ile Gly Ile Ala Gly Lys Ile Leu Gly Thr Leu
        180                 185                 190
```

FIG. 5E

```
                    E                           AH                          D
                    C                           LA                          D
                    O                           UE                          E
                    1                           11                          1
GGC GTT CCT TTT GCA GGA CAA GTA GCT AGT CTT TAT AGT TTT ATC TTA    624
Gly Val Pro Phe Ala Gly Gln Val Ala Ser Leu Tyr Ser Phe Ile Leu
            195                 200                 205

A       HH  HMD                                         A
        L       AP  ASD                                         F
        V       EH  ETE                                         L
        1       11  321                                         3
GGT GAG CTA TGG CCT AAG GGG AAA AAT CAA TGG GAA ATC TTT ATG GAA    672
Gly Glu Leu Trp Pro Lys Gly Lys Asn Gln Trp Glu Ile Phe Met Glu
            210                 215                 220

NNK     E                       AM  M
SLS     A                       SS  B
PAP     R                       EE  O
H32     1                       11  2
CAT GTA GAA GAG ATT ATT AAT CAA AAA ATA TCA ACT TAT GCA AGA AAT    720
His Val Glu Glu Ile Ile Asn Gln Lys Ile Ser Thr Tyr Ala Arg Asn
225                 230                 235                 240
```

FIG. 5F

```
                                            S           D         A
                                            F           D         L  A
                                            A           E         U  C
                                            N           1         1  1
AAA GCA CTT ACA GAC TTG AAA GGA TTA GGA GAT GCC TTA GCT GTC TAC       768
Lys Ala Leu Thr Asp Leu Lys Gly Leu Gly Asp Ala Leu Ala Val Tyr
             245                 250                 255

NH    H                                                  M
    LN    N                                                  A
    AF    F                                                  E
    31    3                                                  1
    /
CAT GAT TCG CTT GAA AGT TGG GTT GGA AAT CGT AAT AAC ACA AGG GCT       816
His Asp Ser Leu Glu Ser Trp Val Gly Asn Arg Asn Asn Thr Arg Ala
             260                 265                 270

AGG AGT GTT GTC AAG AGC CAA TAT ATC GCA TTA GAA TTG ATG TTC GTT       864
Arg Ser Val Val Lys Ser Gln Tyr Ile Ala Leu Glu Leu Met Phe Val
             275                 280                 285
```

FIG. 5G

```
                                              M  AM         B  ANR  K
                                              N  LN         A  SLS  P
                                              L  WL         N  PAA  N
                                              1  H1         1  141  1
                                                                / /
CAG AAA CTA CCT TCT TTT GCA GTG TCT GGA GAG GTA CCA TTA TTA       912
Gln Lys Leu Pro Ser Phe Ala Val Ser Gly Glu Val Pro Leu Leu
290                 295                 300

B   AF                                              S   M
       B   LN                                              F   S
       V   UU                                              A   E
       1   1H                                              N   1
CCG ATA TAT GCC CAA GCT GCA AAT TTA CAT TTG CTA TTA AGA GAT       960
Pro Ile Tyr Ala Gln Ala Ala Asn Leu His Leu Leu Leu Arg Asp
305                 310                 315                 320

N  A      S                              M
   S  V      F                              B
   1  A      A                              O
   1  3      N                              2
     / /
GCA TCT ATT TTT GGA AAA GAG TGG GGA TTA TCA TCT TCA GAA ATT TCA  1008
Ala Ser Ile Phe Gly Lys Glu Trp Gly Leu Ser Ser Ser Glu Ile Ser
                325                 330                 335
```

FIG. 5H

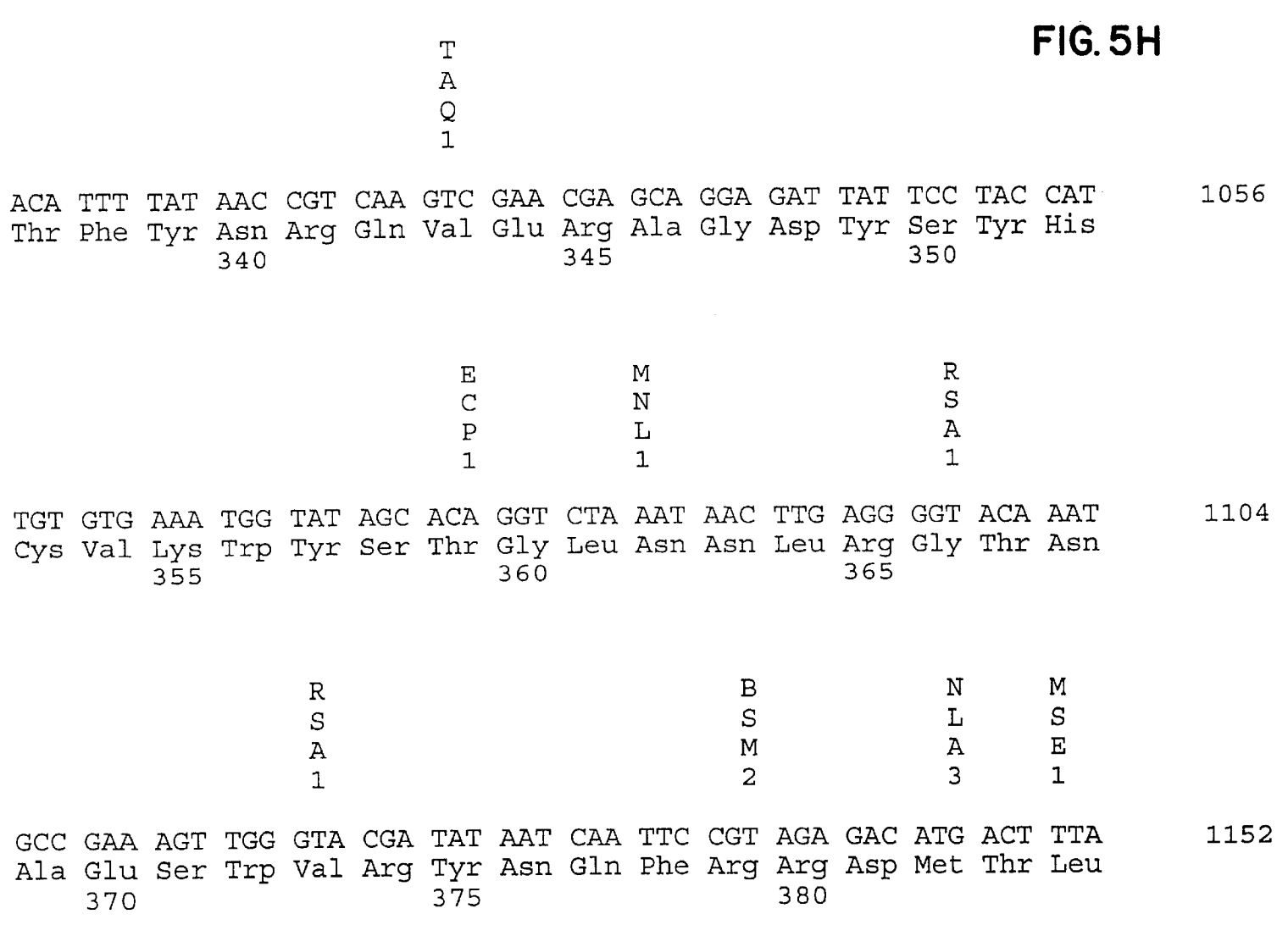

```
                                                T
                                                A
                                                Q
                                                1
ACA TTT TAT AAC CGT CAA GTC GAA CGA GCA GGA GAT TAT TCC TAC CAT    1056
Thr Phe Tyr Asn Arg Gln Val Glu Arg Ala Gly Asp Tyr Ser Tyr His
        340             345             350

E                       R
                            C                       S
                            P                       A
                            1                       1
                    M
                    N
                    L
                    1
TGT GTG AAA TGG TAT AGC ACA GGT CTA AAT AAC TTG AGG GGT ACA AAT    1104
Cys Val Lys Trp Tyr Ser Thr Gly Leu Asn Asn Leu Arg Gly Thr Asn
        355             360             365

R               B               N       M
            S               S               L       S
            A               M               A       E
            1               2               3       1
GCC GAA AGT TGG GTA CGA TAT AAT CAA TTC CGT AGA GAC ATG ACT TTA    1152
Ala Glu Ser Trp Val Arg Tyr Asn Gln Phe Arg Arg Asp Met Thr Leu
        370             375             380
```

FIG. 5I

```
ECOD  ERMA   ALU
      SAE    1
      1
ATG GTA CTA GAT TTA GTG GCA CTA TTT CCA AGC TAT GAT ACA CAA ATG    1200
Met Val Leu Asp Leu Val Ala Leu Phe Pro Ser Tyr Asp Thr Gln Met
385                 390                 395                 400

MSE
            1
TAT CCA ATT AAA ACT ACA GCC CAA CTT ACA AGA GAA GTA TAT ACA GAC    1248
Tyr Pro Ile Lys Thr Thr Ala Gln Leu Thr Arg Glu Val Tyr Thr Asp
            405                 410                 415

FOK  HF  FR   SF   RS
1    GO  IS   AA   AA
     AK  NA   N    1
     11  1    1
GCA ATT GGG ACA GTA CAT CCG CAT CCA AGT TTT ACA AGT ACG ACT TGG    1296
Ala Ile Gly Thr Val His Pro His Pro Ser Phe Thr Ser Thr Thr Trp
            420                 425                 430
```

FIG. 5J

```
                                                                    BBN  BML                BGL  FNU  ECI  ASA
                                                                    BVV  NLI                LI1  NUH  C1I  SUA
                                                                    I1   1                  1    H    5    I2
TAT AAT AAT AAT GCA CCT TCG TTC TCT GCC ATA GAG GCT GCT GTT GTT     1344
Tyr Asn Asn Asn Ala Pro Ser Phe Ser Ala Ile Glu Ala Ala Val Val
                435                 440                 445

TAQ1           TSQA1N              XBA1   MAE3                           MAE1  ALU1
CGA AAC CCG CAT CTA GAT CTC TTT CTA GAA CAA GTT ACA ATT TAC AGC     1392
Arg Asn Pro His Leu Asp Leu Phe Leu Glu Gln Val Thr Ile Tyr Ser
                450                 455                 460

MSE1  TAQ1   MAE3   DDE1                    MKL1
TTA TTA AGT CGA TGG AGT AAC ACT CAG TAT ATG AAT ATG TGG GGA GGA     1440
Leu Leu Ser Arg Trp Ser Asn Thr Gln Tyr Met Asn Met Trp Gly Gly
                465                 470                 475                 480
```

FIG. 5K

```
                 M           M
                 A           N
                 E           L
                 1           1

CAT AAA CTA GAA TTC CGA ACA ATA GGA GGA ACG TTA AAT ATC TCA ACA    1488
His Lys Leu Glu Phe Arg Thr Ile Gly Gly Thr Leu Asn Ile Ser Thr
             485                 490                 495

M   M
                                             A   S
                                             E   E
                                             2   1

B  XMD                              AM                M
   1  HBP                              SS                A
   N  OON                              EE                E
   1  211                              11                3
      / /                              //
CAA GGA TCT ACT AAT ACT TCT ATT AAT CCT GTA ACA TTA CCG TTC ACT    1536
Gln Gly Ser Thr Asn Thr Ser Ile Asn Pro Val Thr Leu Pro Phe Thr
             500                 505                 510

XA  TB  AM  A                              H            H
HV  AS  HA  A                              N            N
OA  QM  AE  T                              F            F
11  12  22  2                              1            1
 /   /   /
TCT CGA GAC GTC TAT AGG ACT GAA TCA TTG GCA GGG CTG AAT CTA TTT    1584
Ser Arg Asp Val Tyr Arg Thr Glu Ser Leu Ala Gly Leu Asn Leu Phe
             515                 520                 525
```

FIG. 5L

```
MSE1    MSE1    RSA1    SPO1    FOK1
                SAS M   SAS M   
                TVE A   
                YRC E   
                121 1

TTA ACT CAA CCT GTT AAT GGA GTA CCT AGG GTT GAT TTT CAT TGG AAA    1632
Leu Thr Gln Pro Val Asn Gly Val Pro Arg Val Asp Phe His Trp Lys
530                     535                     540

MAEF3   MBO1    TES SAS
                DPNU11  TCEPC
                        HRCYR
                        22 111

TTC GTC ACA CAT CCG ATC GCA TCT GAT AAT TTC TAT TAT CCA GGG TAT    1680
Phe Val Thr His Pro Ile Ala Ser Asp Asn Phe Tyr Tyr Pro Gly Tyr
545                     550                     555                     560

FIN1    HGA1    HNF1

GCT GGA ATT GGG ACG CAA TTA CAG GAT TCA GAA AAT GAA TTA CCA CCT    1728
Ala Gly Ile Gly Thr Gln Leu Gln Asp Ser Glu Asn Glu Leu Pro Pro
                565                     570                     575
```

FIG. 5M

```
                                                    H
                                                    N
                                                    F
                                                    1
GAA GCA ACA GGA CAG CCA AAT TAT GAA TCT TAT AGT CAT AGA TTA TCT    1776
Glu Ala Thr Gly Gln Pro Asn Tyr Glu Ser Tyr Ser His Arg Leu Ser
             580                 585                 590

P   H                             A
    L   N                             F   S N N
    E   F                             L   F S L
    1   1                             3   A P A
                                          N H 3
                                          //
CAT ATA GGA CTC ATT TCA GCA TCA CAT GTG AAA GCA TTG GTA TAT TCT    1824
His Ile Gly Leu Ile Ser Ala Ser His Val Lys Ala Leu Val Tyr Ser
         595                 600                 605

H   S   M D   R
        G   F   B P   S
        A   A   O N   A
        1   N   1     1
TGG ACG CAT CGT AGT GCA GAT CGT ACA AAT ACA ATT GAG CCA AAT AGC    1872
Trp Thr His Arg Ser Ala Asp Arg Thr Asn Thr Ile Glu Pro Asn Ser
         610                 615                 620
```

FIG.5N

```
                                    H     M           B  B N   F
                                    A     B           B  A L A N U H
                                    L     O           V  N A 1 A H
                                    U     2           2    4   U
                                    1
                                    N
                                    3
ATT ACA CAA ATA CCA TTA GTA AAA GCT TTC AAT CTG TCT TCA GGT GCC    1920
Ile Thr Gln Ile Pro Leu Val Lys Ala Phe Asn Leu Ser Ser Gly Ala
625             630             635             640

N M         A A E   A S                         E           A  T
    S N         V S C   P C                         C           S  A
    P L         A U R   Y R                         R           U  Q
    B 1         2 1 2   1 1                         V           2  1
                        /                                          /
GCT GTA GTG AGA GGA CCA GGA TTT ACA GGT GGG GAT ATC CTT CGA AGA    1968
Ala Val Val Arg Gly Pro Gly Phe Thr Gly Gly Asp Ile Leu Arg Arg
                645             650             655

H       M  R                                        S  A M
    N       B  S                                        S  S S
    F       O  A                                        P  E E
    3       2  1                                        1  1 1
                                                                /
ACG AAT ACT GGT GGA ACA TTT GGG GAT ATA CGA GTA AAT ATT AAT CCA CCA   2016
Thr Asn Thr Gly Gly Thr Phe Gly Asp Ile Arg Val Asn Ile Asn Pro Pro
            660             665             670
```

FIG. 50

```
                EM    T           H        H
                CN    H           N        N
                RL    A           F        F
                V1    1           1        3
TTT GCA CAA AGA TAT  CGC GTG AGG ATT CGC TAT GCT TCT ACC ACA GAT   2064
Phe Ala Gln Arg Tyr  Arg Val Arg Ile Arg Tyr Ala Ser Thr Thr Asp
            675              680              685

M       M                          A    AM
        A       S                          L    SS
        E       E                          U    EE
        2       1                          1    11
TTA CAA TTC CAT ACG TCA ATT AAC GGT AAA GCT ATT AAT CAA GGT AAT   2112
Leu Gln Phe His Thr Ser Ile Asn Gly Lys Ala Ile Asn Gln Gly Asn
            690              695              700

M            M                    D
            N            N                    D
            L            L                    E
            1            1                    1
TTT TCA GCA ACT ATG AAT AGA GGA GAG GAC TTA GAC TAT AAA ACC TTT   2160
Phe Ser Ala Thr Met Asn Arg Gly Glu Asp Leu Asp Tyr Lys Thr Phe
            705              710              715              720
```

FIG. 5P

```
                                              A       R   R
                                              L       S   S
                                              U       A   A
                                              1       1   1
AGA ACT GTA GGC TTT ACC ACT CCA TTT AGC TTT TTA GAT GTA CAA AGT    2208
Arg Thr Val Gly Phe Thr Thr Pro Phe Ser Phe Leu Asp Val Gln Ser
                725                 730                 735

M               K  EM
                        B               S  AA
                        O               P  RE
                        2               2  13
                                           //
ACA TTC ACA ATA GGT GCT TGG AAC TTC TCT TCA GGT AAC GAA GTT TAT    2256
Thr Phe Thr Ile Gly Ala Trp Asn Phe Ser Ser Gly Asn Glu Val Tyr
                740                 745                 750

X       H       M       M   N
        M       P       A       A   D
        N       A       E       N   E
        1       2       3       L   1
                                1
ATA GAT AGA ATT GAA TTT GTT CCG GTA GAA GTA ACA TAT GAG GCA GAA    2304
Ile Asp Arg Ile Glu Phe Val Pro Val Glu Val Thr Tyr Glu Ala Glu
                755                 760                 765
```

FIG. 5Q

```
                                                        HH          M
                                                        IH          A
                                                        NA          E                                                  2352
                                                        P1          3
TAT GAT TTT GAA AAA GCG CAA GAG AAG GTT ACT GCA CTG TTT ACA TCT
Tyr Asp Phe Glu Lys Ala Gln Glu Lys Val Thr Ala Leu Phe Thr Ser
770                     775                     780

HHM                 M                                                  E
            MNN                 S                                                  C
            FFL                 E                                                  R                                   2400
            311                 1                                                  2
ACG AAT CCA AGA GGA TTA AAA ACA GAT GTA AAG GAT TAT CAT ATT GAC
Thr Asn Pro Arg Gly Leu Lys Thr Asp Val Lys Asp Tyr His Ile Asp
785                     790                     795                     800

AS      H           BP                                  E
            PC      N           SL                                  C
            YR      F           ME                                  D                                                  2448
            11      1           21                                  X
CAG GTA TCA AAT TTA GTA GAG TCT CTA TCA GAT GAA TTC TAT CTT GAT
Gln Val Ser Asn Leu Val Glu Ser Leu Ser Asp Glu Phe Tyr Leu Asp
        805                     810                     815
```

FIG.5R

```
                T    H                   M         T
                A    N                   S         H
                Q    F                   E         A
                1    3                   1         1
GAA AAG AGA GAA TTA TTC GAG ATA GTT AAA TAC GCG AAG CAA CTC CAT    2496
Glu Lys Arg Glu Leu Phe Glu Ile Val Lys Tyr Ala Lys Gln Leu His
        820                 825                 830

M   A   N               M
    A   F   S               S
    E   L   P               E
    3   3   A               1
            H
            3
            /
ATT GAG CGT AAC ATG TAG AAT TAA AAT CTA CCT AAA TCC AGA AAA ATA    2544
Ile Glu Arg Asn Met Ter Asn Ter Asn Leu Pro Lys Ser Arg Lys Ile
        835                 840                 845

M                   R           S
    S                   S           S
    E                   A           P
    1                   1           1
AAA GGG TTA AAT ATA CAA TTC TTG TAC CAA TAT TTT GAG TGA TTA GAT    2592
Lys Gly Leu Asn Ile Gln Phe Leu Tyr Gln Tyr Phe Glu Ter Leu Asp
        850                 855                 860
```

FIG.5S

```
                                              M             M
                                              S             S
                                              E             E
                                              1             1
              M       F
              S       O
              E       K
              1       1
GTA GGA TGA AAT TTA ATT GTA TGC TAT TTA ACA GTA GAG ATA TTA AAA    2640
Val Gly Ter Asn Leu Ile Val Cys Tyr Leu Thr Val Glu Ile Leu Lys
865             870             875             880

A  M
        S  S
        E  E
        1  1
AM
SS
EE
11
ATT AAT TTA TCT ATA CAT TAA TAG TAT AGA CAT ACA AAC ATA AGA GAG    2688
Ile Asn Leu Ser Ile His Ter Ter Tyr Arg His Thr Asn Ile Arg Glu
            885             890             895

CAT TGT CTT TTC GTA GGC TAC AAT GCT CTC TAT TTA CTA TTT ATT TTT    2736
His Cys Leu Phe Val Gly Tyr Asn Ala Leu Tyr Leu Leu Phe Ile Phe
900             905             910
```

FIG. 5T

```
                                                          MAE2         DDE1              FA
                                                                                         NL
                                                                                         UU
                                                                                         H1
MBO2
CTT TTG TAT CTT CAA ATT GAC GTT GTT CTA AGC GTT CTA TTG CAG CTC       2784
Leu Leu Tyr Leu Gln Ile Asp Val Val Leu Ser Val Leu Leu Gln Leu
            915             920             925

BBV1
GTC GTT TAG TAT CAT CAA TGT TTG TAT AAA GAG ATG TTG TTT CCA TAG       2832
Val Val Ter Tyr His Gln Cys Leu Tyr Lys Glu Met Leu Phe Pro Ter
            930             935             940

FHN1
AAT TAT GTC CCA TTT GAT TTG CTA ATA ATA CTA AAT CTT TAT TTT CAT       2880
Asn Tyr Val Pro Phe Asp Leu Leu Ile Ile Leu Asn Leu Tyr Phe His
            945             950             955             960
```

FIG.5U

```
                              MAE2    MNL1
TAT AGT GAT TAG TAG CAT AAG TAT GAC GTA ATT TAT GAG GGC TTT TCT    2928
Tyr Ser Asp Ter Ter His Lys Tyr Asp Val Ile Tyr Glu Gly Phe Ser
            965                 970                 975

HINT3  HAL
TTT CAT CAA AAG CCC TTG TGT ATT TCT CTG TAA GCT T                  2965
Phe His Gln Lys Pro Leu Cys Ile Ser Leu Ter Ala Ser
            980                 985
```

FIG. 6A

```
ATG AAA CTA AAG AAT CAA GAT AAG CAT CAA AGT TTT TCT AGC AAT GCG       48
Met Lys Leu Lys Asn Gln Asp Lys His Gln Ser Phe Ser Ser Asn Ala
 1               5                  10                  15

AAA GTA GAT AAA ATC TCT ACG GAT TCA CTA AAA AAT GAA ACA GAT ATA       96
Lys Val Asp Lys Ile Ser Thr Asp Ser Leu Lys Asn Glu Thr Asp Ile
                20                  25                  30

GAA TTA CAA AAC ATT AAT CAT GAA GAT TGT TTG AAA ATG TCT GAG TAT      144
Glu Leu Gln Asn Ile Asn His Glu Asp Cys Leu Lys Met Ser Glu Tyr
                35                  40                  45

GAA AAT GTA GAG CCG TTT GTT AGT GCA TCA ACA ATT CAA ACA GGT ATT      192
Glu Asn Val Glu Pro Phe Val Ser Ala Ser Thr Ile Gln Thr Gly Ile
                50                  55                  60
```

FIG. 6B

```
GGT ATT GCG GGT AAA ATA CTT GGT ACC CTA GGC GTT CCT TTT GCA GGA   240
Gly Ile Ala Gly Lys Ile Leu Gly Thr Leu Gly Val Pro Phe Ala Gly
 65                  70                  75                  80

CAA GTA GCT AGT CTT TAT AGT TTT ATC TTA GGT GAG CTA TGG CCT AAG   288
Gln Val Ala Ser Leu Tyr Ser Phe Ile Leu Gly Glu Leu Trp Pro Lys
             85                  90                  95

GGG AAA AAT CAA TGG GAA ATC TTT ATG GAA CAT GTA GAA GAG ATT ATT   336
Gly Lys Asn Gln Trp Glu Ile Phe Met Glu His Val Glu Glu Ile Ile
        100                 105                 110

AAT CAA AAA ATA TCA ACT TAT GCA AGA AAT AAA GCA CTT ACA GAC TTG   384
Asn Gln Lys Ile Ser Thr Tyr Ala Arg Asn Lys Ala Leu Thr Asp Leu
    115                 120                 125
```

FIG. 6C

```
AAA GGA TTA GGA GAT GCC TTA GCT GTC TAC CAT GAT TCG CTT GAA AGT    432
Lys Gly Leu Gly Asp Ala Leu Ala Val Tyr His Asp Ser Leu Glu Ser
130                 135                 140

TGG GTT GGA AAT CGT AAT AAC ACA AGG GCT AGG AGT GTT AAG AGC        480
Trp Val Gly Asn Arg Asn Asn Thr Arg Ala Arg Ser Val Val Lys Ser
145                 150                 155                 160

CAA TAT ATC GCA TTA GAA TTG ATG TTC GTT CAG AAA CTA CCT TCT TTT    528
Gln Tyr Ile Ala Leu Glu Leu Met Phe Val Gln Lys Leu Pro Ser Phe
            165                 170                 175

GCA GTG TCT GGA GAG GTA CCA TTA TTA CCG ATA TAT GCC CAA GCT        576
Ala Val Ser Gly Glu Val Pro Leu Leu Pro Ile Tyr Ala Gln Ala
180                 185                 190
```

FIG. 6D

```
GCA AAT TTA CAT TTG CTA TTA AGA GAT GCA TCT ATT TTT GGA AAA      624
Ala Asn Leu His Leu Leu Leu Arg Asp Ala Ser Ile Phe Gly Lys
        195                 200                 205

GAG TGG GGA TTA TCA TCT TCA GAA ATT TCA ACA TTT TAT AAC CGT CAA  672
Glu Trp Gly Leu Ser Ser Ser Glu Ile Ser Thr Phe Tyr Asn Arg Gln
    210                 215                 220

GTC GAA CGA GCA GGA GAT TAT TCC GAC CAT TGT GTG AAA TGG TAT AGC  720
Val Glu Arg Ala Gly Asp Tyr Ser Asp His Cys Val Lys Trp Tyr Ser
225                 230                 235                 240

ACA GGT CTA AAT AAC TTG AGG GGT ACA AAT GCC GAA AGT TGG GTA CGA  768
Thr Gly Leu Asn Asn Leu Arg Gly Thr Asn Ala Glu Ser Trp Val Arg
            245                 250                 255
```

FIG. 6E

```
TAT AAT CAA TTC CGT AGA GAC ATG ACT TTA ATG GTA CTA GAT TTA GTG    816
Tyr Asn Gln Phe Arg Arg Asp Met Thr Leu Met Val Leu Asp Leu Val
        260                 265                 270

GCA CTA TTT CCA AGC TAT GAT ACA CAA ATG TAT CCA ATT AAA ACT ACA    864
Ala Leu Phe Pro Ser Tyr Asp Thr Gln Met Tyr Pro Ile Lys Thr Thr
        275                 280                 285

GCC CAA CTT ACA AGA GAA GTA TAT ACA GAC GCA ATT GGG ACA GTA CAT    912
Ala Gln Leu Thr Arg Glu Val Tyr Thr Asp Ala Ile Gly Thr Val His
        290                 295                 300

CCG CAT CCA AGT TTT ACA AGT ACG ACT TGG TAT AAT AAT GCA CCT        960
Pro His Pro Ser Phe Thr Ser Thr Thr Trp Tyr Asn Asn Ala Pro
        305                 310                 315             320
```

FIG. 6F

```
TCG TTC TCT GCC ATA GAG GCT GCT GTT GTT CGA AAC CCG CAT CTA CTC    1008
Ser Phe Ser Ala Ile Glu Ala Ala Val Val Arg Asn Pro His Leu Leu
            325                 330                 335

GAT TTT CTA GAA CAA GTT ACA ATT TAC AGC TTA TTA AGT CGA TGG AGT    1056
Asp Phe Leu Glu Gln Val Thr Ile Tyr Ser Leu Leu Ser Arg Trp Ser
            340                 345                 350

AAC ACT CAG TAT ATG AAT ATG TGG GGA GGA CAT AAA CTA GAA TTC CGA    1104
Asn Thr Gln Tyr Met Asn Met Trp Gly Gly His Lys Leu Glu Phe Arg
            355                 360                 365
```

FIG. 6G

```
ACA ATA GGA GGA ACG TTA AAT ATC TCA ACA CAA GGA TCT ACT AAT ACT   1152
Thr Ile Gly Gly Thr Leu Asn Ile Ser Thr Gln Gly Ser Thr Asn Thr
370                 375                 380

TCT ATT AAT CCT GTA ACA TTA CCG TTC ACT TCT CGA GAC GTC TAT AGG   1200
Ser Ile Asn Pro Val Thr Leu Pro Phe Thr Ser Arg Asp Val Tyr Arg
385                 390                 395                 400

ACT GAA TCA TTG GCA GGG CTG AAT CTA TTT TTA ACT CAA CCT GTT AAT   1248
Thr Glu Ser Leu Ala Gly Leu Asn Leu Phe Leu Thr Gln Pro Val Asn
        405                 410                 415

GGA GTA CCT AGG GTT GAT TTT CAT TGG AAA TTC GTC ACA CAT CCG ATC   1296
Gly Val Pro Arg Val Asp Phe His Trp Lys Phe Val Thr His Pro Ile
420                 425                 430
```

FIG. 6H

```
GCA TCT GAT AAT TTC TAT TAT CCA GGG TAT GCT GGA ATT GGG ACG CAA    1344
Ala Ser Asp Asn Phe Tyr Tyr Pro Gly Tyr Ala Gly Ile Gly Thr Gln
435                 440                 445

TTA CAG GAT TCA GAA AAT GAA TTA CCA CCT GAA GCA ACA GGA CAG CCA    1392
Leu Gln Asp Ser Glu Asn Glu Leu Pro Pro Glu Ala Thr Gly Gln Pro
450                 455                 460

AAT TAT GAA TCT TAT AGT CAT AGA TTA TCT CAT ATA GGA CTC ATT TCA    1440
Asn Tyr Glu Ser Tyr Ser His Arg Leu Ser His Ile Gly Leu Ile Ser
465                 470                 475                 480

GCA TCA CAT GTG AAA GCA TTG GTA TAT TCT TGG ACG CAT CGT AGT GCA    1488
Ala Ser His Val Lys Ala Leu Val Tyr Ser Trp Thr His Arg Ser Ala
                485                 490                 495
```

FIG. 6I

```
GAT CGT ACA AAT ACA ATT GAG CCA AAT AGC ATT ACA CAA ATA CCA TTA    1536
Asp Arg Thr Asn Thr Ile Glu Pro Asn Ser Ile Thr Gln Ile Pro Leu
            500                 505                 510

GTA AAA GCT TTC AAT CTG TCT TCA GGT GCC GCT GTA GTG AGA GGA CCA    1584
Val Lys Ala Phe Asn Leu Ser Ser Gly Ala Ala Val Val Arg Gly Pro
            515                 520                 525

GGA TTT ACA GGT GGG GAT ATC CTT CGA AGA ACG AAT ACT GGT ACA TTT    1632
Gly Phe Thr Gly Gly Asp Ile Leu Arg Arg Thr Asn Thr Gly Thr Phe
            530                 535                 540

GGG GAT ATA CGA GTA AAT ATT AAT CCA CCA TTT GCA CAA AGA TAT CGC    1680
Gly Asp Ile Arg Val Asn Ile Asn Pro Pro Phe Ala Gln Arg Tyr Arg
            545                 550                 555

GTG AGG ATT CGC TAT GCT TCT ACC ACA GAT TTA CAA TTC CAT ACG TCA    1728
Val Arg Ile Arg Tyr Ala Ser Thr Thr Asp Leu Gln Phe His Thr Ser
            560                 565                 570                 575
```

FIG. 6J

```
ATT AAC GGT AAA GCT ATT AAT CAA GGT AAT TTT TCA GCA ACT ATG AAT    1776
Ile Asn Gly Lys Ala Ile Asn Gln Gly Asn Phe Ser Ala Thr Met Asn
        580                 585                 590

AGA GGA GAG GAC TTA GAC TAT AAA ACC TTT AGA ACT GTA GGC TTT ACC    1824
Arg Gly Glu Asp Leu Asp Tyr Lys Thr Phe Arg Thr Val Gly Phe Thr
        595                 600                 605

ACT CCA TTT AGC TTT TTA GAT GTA CAA AGT ACA TTC ACA ATA GGT GCT    1872
Thr Pro Phe Ser Phe Leu Asp Val Gln Ser Thr Phe Thr Ile Gly Ala
        610                 615                 620

TGG AAC TTC TCT TCA GGT AAC GAA GTT TAT ATA GAT AGA ATT GAA TTT    1920
Trp Asn Phe Ser Ser Gly Asn Glu Val Tyr Ile Asp Arg Ile Glu Phe
        625                 630                 635                 640

GTT CCG GTA GAA GTA ACA TAT GAG TG                                 1947
Val Pro Val Glu Val Thr Tyr Glu
                    645
```

FIG.7A

```
ATG AAA CTA AAG AAT CAA GAT AAG CAT CAA AGT TTT TCT AGC AAT GCG     48
Met Lys Leu Lys Asn Gln Asp Lys His Gln Ser Phe Ser Ser Asn Ala
 1               5                  10                  15

AAA GTA GAT AAA ATC TCT ACG GAT TCA CTA AAA AAT GAA ACA GAT ATA     96
Lys Val Asp Lys Ile Ser Thr Asp Ser Leu Lys Asn Glu Thr Asp Ile
            20                  25                  30

GAA TTA CAA AAC ATT AAT CAT GAA GAT TGT TTG AAA ATG TCT GAG TAT    144
Glu Leu Gln Asn Ile Asn His Glu Asp Cys Leu Lys Met Ser Glu Tyr
        35                  40                  45

GAA AAT GTA GAG CCG TTT GTT AGT GCA TCA ACA ATT CAA ACA GGT ATT    192
Glu Asn Val Glu Pro Phe Val Ser Ala Ser Thr Ile Gln Thr Gly Ile
    50                  55                  60
```

FIG. 7B

```
GGT ATT GCG GGT AAA ATA CTT GGT ACC CTA GGC GTT CCT TTT GCA GGA   240
Gly Ile Ala Gly Lys Ile Leu Gly Thr Leu Gly Val Pro Phe Ala Gly
 65                  70                  75                  80

CAA GTA GCT AGT CTT TAT AGT TTT ATC TTA GGT GAG CTA TGG CCT AAG   288
Gln Val Ala Ser Leu Tyr Ser Phe Ile Leu Gly Glu Leu Trp Pro Lys
             85                  90                  95

GGG AAA AAT CAA TGG GAA ATC TTT ATG GAA CAT GTA GAA GAG ATT ATT   336
Gly Lys Asn Gln Trp Glu Ile Phe Met Glu His Val Glu Glu Ile Ile
        100                 105                 110

AAT CAA AAA ATA TCA ACT TAT GCA AGA AAT AAA GCA CTT ACA GAC TTG   384
Asn Gln Lys Ile Ser Thr Tyr Ala Arg Asn Lys Ala Leu Thr Asp Leu
115                 120                 125
```

FIG. 7C

```
AAA GGA TTA GGA GAT GCC TTA GCT GTC TAC CAT GAT TCG CTT GAA AGT      432
Lys Gly Leu Gly Asp Ala Leu Ala Val Tyr His Asp Ser Leu Glu Ser
130                 135                 140

TGG GTT GGA AAT CGT AAT AAC ACA AGG GCT AGG AGT GTT GTC AAG AGC      480
Trp Val Gly Asn Arg Asn Asn Thr Arg Ala Arg Ser Val Val Lys Ser
145                 150                 155                 160

CAA TAT ATC GCA TTA GAA TTG ATG TTC GTT CAG AAA CTA CCT TCT TTT      528
Gln Tyr Ile Ala Leu Glu Leu Met Phe Val Gln Lys Leu Pro Ser Phe
        165                 170                 175

GCA GTG TCT GGA GAG GTA CCA TTA TTA CCG ATA TAT GCC CAA GCT          576
Ala Val Ser Gly Glu Val Pro Leu Leu Pro Ile Tyr Ala Gln Ala
180                 185                 190
```

FIG. 7D

```
GCA AAT TTA CAT TTG TTG CTA TTA AGA GAT GCA TCT ATT TTT GGA AAA    624
Ala Asn Leu His Leu Leu Leu Leu Arg Asp Ala Ser Ile Phe Gly Lys
        195                 200                 205

GAG TGG GGA TTA TCA TCT TCA GAA ATT TCA ACA TTT TAT AAC CGT CAA    672
Glu Trp Gly Leu Ser Ser Ser Glu Ile Ser Thr Phe Tyr Asn Arg Gln
        210                 215                 220

GTC GAA CGA GCA GGA GAT TAT TCC GAC CAT TGT GTG AAA TGG TAT AGC    720
Val Glu Arg Ala Gly Asp Tyr Ser Asp His Cys Val Lys Trp Tyr Ser
        225                 230                 235                 240

ACA GGT CTA AAT AAC TTG AGG GGT ACA AAT GCC GAA AGT TGG GTA CGA    768
Thr Gly Leu Asn Asn Leu Arg Gly Thr Asn Ala Glu Ser Trp Val Arg
                245                 250                 255
```

FIG. 7E

```
TAT AAT CAA TTC CGT AGA GAC ATG ACT TTA ATG GTA CTA GAT TTA GTG
Tyr Asn Gln Phe Arg Arg Asp Met Thr Leu Met Val Leu Asp Leu Val
        260                 265                 270                       816

GCA CTA TTT CCA AGC TAT GAT ACA CAA ATG TAT CCA ATT AAA ACT ACA
Ala Leu Phe Pro Ser Tyr Asp Thr Gln Met Tyr Pro Ile Lys Thr Thr
        275                 280                 285                       864

GCC CAA CTT ACA AGA GAA GTA TAT ACA GAC GCA ATT GGG ACA GTA CAT
Ala Gln Leu Thr Arg Glu Val Tyr Thr Asp Ala Ile Gly Thr Val His
        290                 295                 300                       912

CCG CAT CCA AGT TTT ACA AGT ACG ACT TGG TAT AAT AAT GCA CCT
Pro His Pro Ser Phe Thr Ser Thr Thr Trp Tyr Asn Asn Ala Pro
305                 310                 315         320                    960
```

FIG.7F

```
TCG TTC TCT GCC ATA GAG GCT GCT GTT CGA GTT GTT CGA AAC CCG CAT CTA CTC    1008
Ser Phe Ser Ala Ile Glu Ala Ala Val Val Val Arg Asn Pro His Leu Leu
            325                 330                 335

GAT TTT CTA GAA CAA GTT ACA ATT TAC AGC TTA TTA AGT CGA TGG AGT            1056
Asp Phe Leu Glu Gln Val Thr Ile Tyr Ser Leu Leu Ser Arg Trp Ser
            340                 345                 350

AAC ACT CAG TAT ATG AAT ATG TGG GGA GGA CAT AAA CTA GAA TTC CGA            1104
Asn Thr Gln Tyr Met Asn Met Trp Gly Gly His Lys Leu Glu Phe Arg
            355                 360                 365

ACA ATA GGA GGA ACG TTA AAT ATC TCA ACA CAA GGA TCT ACT AAT ACT            1152
Thr Ile Gly Gly Thr Leu Asn Ile Ser Thr Gln Gly Ser Thr Asn Thr
            370                 375                 380
```

FIG. 7G

```
TCT ATT AAT CCT GTA ACA TTA CCG TTC ACT TCT CGA GAC GTC TAT AGG   1200
Ser Ile Asn Pro Val Thr Leu Pro Phe Thr Ser Arg Asp Val Tyr Arg
385                 390                 395                 400

ACT GAA TCA TTG GCA GGG CTG AAT CTA TTT TTA ACT CAA CCT GTT AAT   1248
Thr Glu Ser Leu Ala Gly Leu Asn Leu Phe Leu Thr Gln Pro Val Asn
        405                 410                 415

GGA GTA CCT AGG GTT GAT TTT CAT TGG AAA TTC GTC ACA CAT CCG ATC   1296
Gly Val Pro Arg Val Asp Phe His Trp Lys Phe Val Thr His Pro Ile
    420                 425                 430

GCA TCT GAT AAT TTC TAT TAT CCA GGG TAT GCT GGA ATT GGG ACG CAA   1344
Ala Ser Asp Asn Phe Tyr Tyr Pro Gly Tyr Ala Gly Ile Gly Thr Gln
435                 440                 445
```

FIG. 7H

```
TTA CAG GAT TCA GAA AAT GAA TTA CCT GAA GCA ACA GGA CAG CCA      1392
Leu Gln Asp Ser Glu Asn Glu Leu Pro Pro Glu Ala Thr Gly Gln Pro
450                 455                 460

AAT TAC GAA TCT TAT AGT CAT AGA TTA TCT CAT ATA GGA CTC ATT TCA  1440
Asn Tyr Glu Ser Tyr Ser His Arg Leu Ser His Ile Gly Leu Ile Ser
        465                 470                 475         480

GCA TCA CAT GTG AAA GCA TTG GTA TAT TCT TGG ACG CAT CGT AGT GCA  1488
Ala Ser His Val Lys Ala Leu Val Tyr Ser Trp Thr His Arg Ser Ala
                485                 490                 495

GAT CGT ACA AAT ACA ATT GAG CCA AAT AGC ATT ACA CAA ATA CCA TTA  1536
Asp Arg Thr Asn Thr Ile Glu Pro Asn Ser Ile Thr Gln Ile Pro Leu
        500                 505                 510
```

FIG. 7I

```
GTA AAA GCT TTC AAT CTG TCT TCA GGT GCC GCT GTA GTG AGA GGA CCA    1584
Val Lys Ala Phe Asn Leu Ser Ser Gly Ala Ala Val Val Arg Gly Pro
515                 520                 525

GGA TTT ACA GGT GGG GAT ATC TAG                                    1608
Gly Phe Thr Gly Gly Asp Ile
530                 535
```

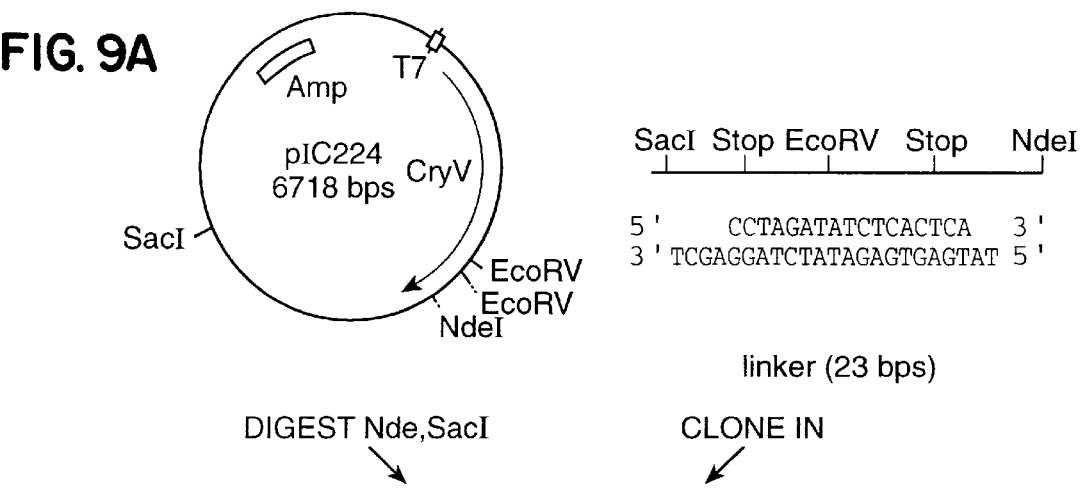
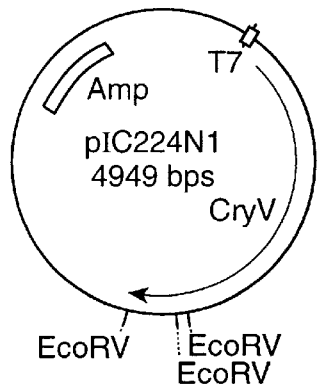
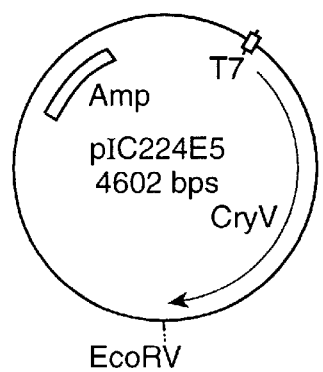
FIG. 9A
FIG. 9B
FIG. 9C

FIG. IIA

```
ATG AAG CTG AAG AAC CAA GAC AAG CAC CAA TCG TTC TCC AGC AAC GCG      48
Met Lys Leu Lys Asn Gln Asp Lys His Gln Ser Phe Ser Ser Asn Ala
 1               5                  10                  15

AAA GTG GAC AAG ATC AGC ACC GAC TCC CTG AAG AAC GAG ACC GAC ATC      96
Lys Val Asp Lys Ile Ser Thr Asp Ser Leu Lys Asn Glu Thr Asp Ile
             20                  25                  30

GAG CTC CAG AAC ATC AAC CAC GAA GAT TGC CTG AAG ATG TCC GAG TAC     144
Glu Leu Gln Asn Ile Asn His Glu Asp Cys Leu Lys Met Ser Glu Tyr
         35                  40                  45

GAG AAC GTG GAG CCG TTC GTG AGC GCC TCC ACC ATC CAG ACC GGC ATC     192
Glu Asn Val Glu Pro Phe Val Ser Ala Ser Thr Ile Gln Thr Gly Ile
     50                  55                  60
```

FIG. 11B

```
GGC ATC GCG GGC AAG ATC CTG GGT ACC CTG GGC GTG CCG TTT GCC GGC    240
Gly Ile Ala Gly Lys Ile Leu Gly Thr Leu Gly Val Pro Phe Ala Gly
 65                  70                  75                  80

CAA GTG GCT AGC CTG TAC AGC TTC ATC CTC GGC GAG CTG TGG CCT AAG    288
Gln Val Ala Ser Leu Tyr Ser Phe Ile Leu Gly Glu Leu Trp Pro Lys
                 85                  90                  95

GGC AAG AAC CAA TGG GAG ATC TTC ATG GAG CAC GTG GAG GAG ATC ATC    336
Gly Lys Asn Gln Trp Glu Ile Phe Met Glu His Val Glu Glu Ile Ile
            100                 105                 110

AAC CAG AAG ATT TCC ACC TAC GCC CGC AAC AAG GCC CTT ACC GAC CTG    384
Asn Gln Lys Ile Ser Thr Tyr Ala Arg Asn Lys Ala Leu Thr Asp Leu
        115                 120                 125
```

FIG. IIC

```
AAG GGC CTC GGC GAC GCC CTG GCT GTC TAC CAC GAC TCC CTG GAG AGC     432
Lys Gly Leu Gly Asp Ala Leu Ala Val Tyr His Asp Ser Leu Glu Ser
130                 135                 140

TGG GTG GGC AAC CGC AAC ACG AGG GCC CGC AGC GTG AAG AGC            480
Trp Val Gly Asn Arg Asn Thr Arg Ala Arg Ser Val Val Lys Ser
145                 150                 155                 160

CAG TAC ATC GCC CTG GAG CTG ATG TTC GTG CAG AAG CTG CCG TCC TTC    528
Gln Tyr Ile Ala Leu Glu Leu Met Phe Val Gln Lys Leu Pro Ser Phe
        165                 170                 175

GCC GTG TCT GGT GAG GAG GTG CCC CTG CTG CCG ATC TAC GCC CAG GCC    576
Ala Val Ser Gly Glu Glu Val Pro Leu Leu Pro Ile Tyr Ala Gln Ala
                180                 185                 190
```

FIG. 11D

```
GCC AAC CTC CAC CTC CTG CTC CTG CGC GAC GCC AGC ATC TTC GGC AAG     624
Ala Asn Leu His Leu Leu Leu Leu Arg Asp Ala Ser Ile Phe Gly Lys
        195                 200                 205

GAG TGG GGC CTG TCC AGC GAG ATC AGC ACG TTC TAC AAC AGG CAG         672
Glu Trp Gly Leu Ser Ser Ser Glu Ile Ser Thr Phe Tyr Asn Arg Gln
    210                 215                 220

GTG GAG CGC GCC GGC GAC TAC AGC GAC CAT TGC GTG AAG TGG TAC AGC     720
Val Glu Arg Ala Gly Asp Tyr Ser Asp His Cys Val Lys Trp Tyr Ser
225                 230                 235                 240

ACC GGC CTG AAC AAC CTG AGG GGC ACC AAC GCC GAG AGC TGG GTC CGC     768
Thr Gly Leu Asn Asn Leu Arg Gly Thr Asn Ala Glu Ser Trp Val Arg
                245                 250                 255
```

FIG. 11E

```
TAC AAT CAG TTC CGC GAC ATG CTG ACC ATG GTG CTG GAC CTG GTG      816
Tyr Asn Gln Phe Arg Asp Met Leu Thr Met Val Leu Asp Leu Val
    260                 265                 270

GCC CTG TTC CCG AGC TAC GAC ACC CAG ATG TAC CCG ATC AAG ACC ACC  864
Ala Leu Phe Pro Ser Tyr Asp Thr Gln Met Tyr Pro Ile Lys Thr Thr
        275                 280                 285

GCC CAG CTG ACC CGC GAG GTG TAC ACC GAC GCC ATT GGC ACC GTG CAC  912
Ala Gln Leu Thr Arg Glu Val Tyr Thr Asp Ala Ile Gly Thr Val His
    290                 295                 300

CCG CAC CCG AGC TTC ACG AGC ACC TGG TAC AAC AAC GCC CCA          960
Pro His Pro Ser Phe Thr Ser Thr Trp Tyr Asn Asn Ala Pro
305                 310                 315             320
```

FIG. IIF

```
AGC TTC AGC GCC ATC GAG GCC GCC GTG GTG CGC AAC CCC CAC CTC CTG    1008
Ser Phe Ser Ala Ile Glu Ala Ala Val Val Arg Asn Pro His Leu Leu
             325                 330                 335

GAC TTC CTG GAG CAG GTG ACC ATC TAC AGC CTG CTG AGC CGG TGG AGC    1056
Asp Phe Leu Glu Gln Val Thr Ile Tyr Ser Leu Leu Ser Arg Trp Ser
         340                 345                 350

AAC ACG CAG TAC ATG AAC ATG TGG GGC CAT AAG CTG GAG TTC AGG        1104
Asn Thr Gln Tyr Met Asn Met Trp Gly His Lys Leu Glu Phe Arg
             355                 360                 365

ACC ATC GGC GGC ACC CTC AAC ATC AGC ACC CAA GGC AGC ACC AAC ACC    1152
Thr Ile Gly Gly Thr Leu Asn Ile Ser Thr Gln Gly Ser Thr Asn Thr
         370                 375                 380
```

FIG. 11G

```
AGC ATC AAC CCG GTC ACC AGC CTG CCC TTC ACC AGC CGC GAC GTG TAC CGC    1200
Ser Ile Asn Pro Val Thr Ser Leu Pro Phe Thr Ser Arg Asp Val Tyr Arg
385                 390                 395                 400

ACC GAG AGC CTG GCC GGC CTG AAC CTG TTC CTG ACC CAG CCC GTG AAC        1248
Thr Glu Ser Leu Ala Gly Leu Asn Leu Phe Leu Thr Gln Pro Val Asn
        405                 410                 415

GGC GTG CCC CGC GTG GAC TTT CAC TGG AAG TTC GTG ACC CAC CCG ATC        1296
Gly Val Pro Arg Val Asp Phe His Trp Lys Phe Val Thr His Pro Ile
    420                 425                 430

GCC AGC GAC AAC TTC TAC TAC CCC GGC TAC GCT GGC ATT GGC ACC CAA        1344
Ala Ser Asp Asn Phe Tyr Tyr Pro Gly Tyr Ala Gly Ile Gly Thr Gln
435                 440                 445
```

FIG. 11H

```
CTC CAG GAC AGC GAG AAC GAG CTG CCG CCC GAG GCC ACC GGT CAG CCG      1392
Leu Gln Asp Ser Glu Asn Glu Leu Pro Pro Glu Ala Thr Gly Gln Pro
450                 455                 460

AAC TAC GAG AGC TAC AGC CAC CGC CTG AGC CAC ATC GGC CTG ATC TCC      1440
Asn Tyr Glu Ser Tyr Ser His Arg Leu Ser His Ile Gly Leu Ile Ser
465                 470                 475                 480

GCC TCC CAC GTG AAG GCC CTG GTG TAC TCC TGG ACC CAC CGC AGC GCC      1488
Ala Ser His Val Lys Ala Leu Val Tyr Ser Trp Thr His Arg Ser Ala
485                 490                 495

GAC CGC ACC AAC ACC ATC GAG CCG AAC AGC ATC ACG CAG ATC CCG CTG      1536
Asp Arg Thr Asn Thr Ile Glu Pro Asn Ser Ile Thr Gln Ile Pro Leu
500                 505                 510
```

FIG. III

```
GTG AAG GCC TTC AAC CTG AGC TCC GGT GCT GCA GTG CGC GGT CCA    1584
Val Lys Ala Phe Asn Leu Ser Ser Gly Ala Ala Val Arg Gly Pro
515                 520                 525

GGC TTC ACA GGC GAC ATC CTG CGC AGG ACC AAC ACC GGC ACC TTC    1632
Gly Phe Thr Gly Asp Ile Leu Arg Arg Thr Asn Thr Gly Thr Phe
530                 535                 540

GGC GAC ATC CGC GTG AAC ATC AAC CCC CCG TTC GCC CAG CGC TAC AGG    1680
Gly Asp Ile Arg Val Asn Ile Asn Pro Pro Phe Ala Gln Arg Tyr Arg
545                 550                 555                 560

GTG AGG ATC AGG TAC GCC AGC ACC ACC GAC CTC CAG TTC CAC ACC AGC    1728
Val Arg Ile Arg Tyr Ala Ser Thr Thr Asp Leu Gln Phe His Thr Ser
565                 570                 575
```

FIG. 11J

```
ATC AAC GGC AAG GCC ATC AAC CAG GGC AAC TTC AGC GCC ACC ATG AAC    1776
Ile Asn Gly Lys Ala Ile Asn Gln Gly Asn Phe Ser Ala Thr Met Asn
        580                 585                 590

CGC GGT GAG GAC CTG GAC TAC AAG ACC TTC CGC ACC GTG GGC TTC ACC    1824
Arg Gly Glu Asp Leu Asp Tyr Lys Thr Phe Arg Thr Val Gly Phe Thr
        595                 600                 605

ACC CCG TTC AGC TTC CTG GAC GTG CAG AGC ACC TTC ACC ATC GGC GCC    1872
Thr Pro Phe Ser Phe Leu Asp Val Gln Ser Thr Phe Thr Ile Gly Ala
        610                 615                 620

TGG AAC TTC AGC AGC GGC AAC GAG GTG TAC ATC GAC CGC ATC GAG TTC    1920
Trp Asn Phe Ser Ser Gly Asn Glu Val Tyr Ile Asp Arg Ile Glu Phe
        625                 630                 635             640
```

FIG. 11K

```
GTG CCC GTG GAG GTG ACC TAC GAG GCC GAG TAC GAC TTC GAG AAG GCC       1968
Val Pro Val Glu Val Thr Tyr Glu Ala Glu Tyr Asp Phe Glu Lys Ala
645                 650                 655

CAG GAG AAG GTC ACC GCC CTG TTC ACC AGC ACC AAC CCG CGC GGC CTG       2016
Gln Glu Lys Val Thr Ala Leu Phe Thr Ser Thr Asn Pro Arg Gly Leu
        660                 665                 670

AAG ACC GAC GTG CAG GAC TAC CAC ATC GAC CAG GTG AGC AAC TTG GTG       2064
Lys Thr Asp Val Gln Asp Tyr His Ile Asp Gln Val Ser Asn Leu Val
675                 680                 685

GAG TCC CTG AGC GAC GAG TTC TAC CTG GAC GAG AAG CGC GAG CTG TTC       2112
Glu Ser Leu Ser Asp Glu Phe Tyr Leu Asp Glu Lys Arg Glu Leu Phe
        690                 695                 700

GAG ATC GTG AAG TAC GCC AAG CAG CTG CAC ATC GAG CGC AAC ATG TA        2160
Glu Ile Val Lys Tyr Ala Lys Gln Leu His Ile Glu Arg Asn Met
705                 710                 715                 720
```

BACILLUS THURINGIENSIS ENDOTOXIN GENES AND METHODS OF USE

This application is a continuation in part of U.S. patent application Ser. No. 07/520,228 filed on May 9, 1990, now U.S. Pat. No. 5,573,766.

The present invention relates to novel bacterial genes, and to novel strains of the bacterium *Bacillus thuringiensis*; and to uses therefor.

The organism *Bacillus thuringiensis* produces a protein crystal endotoxin which kills insect larvae. It is not however toxic to mammals. It is thus very useful as an agricultural insecticide, in particular against Lepidoptera, Coleoptera and Diptera. Strains of *Bacillus thuringiensis* have been used as agricultural insecticides for a number of years.

The most extensively characterized strain of *Bacillus thuringiensis* active against coleopteran pests is *Bacillus thuringiensis* variety (var.) *tenebrionis*, as deposited in the German Collection of Microorganisms (Deutsche Sammlung von Microorganism) under the reference DSM 2803. We have now discovered novel strains of *Bacillus thurinciensis*, which contain at least one novel gene encoding a protein which is insecticidal to either Lepidoptera or Coleoptera. The novel properties of these strains appear to arise from novel genes that they contain.

According to the present invention we provide the novel strains JHCC 4835 and JHCC 4353 of *Bacillus thuringiensis*, deposited at the National Collections of Industrial and Marine Bacteria under the accession numbers NCIB 40091 and 40090, respectively.

We further provide novel δ-endotoxin genes capable of isolation from said strains JHCC 4835 and JHCC 4353, and truncated novel δ-endotoxin genes having insecticidal properties. Such genes may be located either on the bacterial chromosome or on a plasmid. In a further aspect, our invention comprises recombinant DNA homologous with the DNA sequence set out in FIGS. 5A–5U hereof and coding for a novel insecticidally-active endotoxin of molecular weight about 81 kilodaltons (hereinafter referred to as "the 81 kD endotoxin") Additionally our invention comprises recombinant DNA homologous with the DNA sequence set out in FIGS. 6A–6J and coding for novel insecticidally-active protein. In specific embodiments of our invention, recombinant DNA coding for insect endotoxins has been cloned from *Bacillus thuringiensis* JHCC 4835 into *E. coli* strains BL21/pJH11 and MC1022/pJH12, deposited at the National Collections of Industrial and Marine Bacteria under the accession numbers 40275 and 40278 respectively. The endotoxin gene in the latter deposit is lepidopteran-specific. We further provide recombinant DNA coding for a second lepidopteran-specific endotoxin gene derived from *Bacillus thurinaiensis* strain JHCC 4835, which has been deposited in the form of a bacteriophage Lambda EMBL4 clone CL5 with the National Collections of Industrial and Marine Bacteria under the accession number 40279.

Recombinant DNA according to our invention may comprise genes of varying lengths encoding insecticidally-active proteins. When cloning DNA from the bacterial chromosome it is convenient to use bacteriophage Lambda vectors or other cloning vectors that sequester the recombinant DNA from host cell enzymes that might cause homologous recombination.

We further provide novel insecticidal compositions characterized in that they contain the δ-endotoxin produced by said strains JHCC 4835, JHCC 4353 and *E. coli* BL21/pJH11, and a method of protecting plants from insect attack which comprises exposing the larvae to a δ-endotoxin produced by the said strains JHCC 4353, JHCC 4835 and *E. coli* BL21/pJH11.

The strains JHCC 4835 and JHCC 4353 were soil isolates from Marshall, Iowa, USA and Dallas, Iowa, USA respectively. In colony morphology they are somewhat similar to DSM 2803, and to strain HD-1 which is insecticidal to lepidopteran larvae.

The morphology of the strains of the invention is compared with that of known strains in Table 1.

Biochemical properties of the new and the known strains are compared in Tables 2–4. It will be seen that there are many similarities between the strains.

In view of these similarities in insecticidal profile, especially in light of the Coleopteran activity is surprising that the gene encoding the 81 kD endotoxin in *E. coli* BL21/pJH11 shows very little DNA sequence homology to the *B. thurinctiensis* var. *tenebrionis* endotoxin gene of DSM 2803. Use of the coding sequence for *B. thuringiensis* var. *tenebrionis* endotoxin gene as a DNA probe under relatively mild stringency conditions (3× Standard Saline Citrate at 37° C.) is not sufficient to generate a signal from the coding sequences for this endotoxin gene in strains JHCC 4835 and JHCC 4353. Similarly, use of the coding sequence for the lepidopteran-specific cryIA(c) (this being the nomenclature described by Höfte and Whitely in Microbiol. Reviews, 53, 1989 at pages 242–255) endotoxin gene from a *Bacillus thuringiensis* var. *kurstaki* strain is not sufficient to generate a DNA hybridization signal from the coding sequence for the 81 kD endotoxin. Also, use of the novel gene coding sequence as a DNA probe does not generate a hybridization signal from the *tenebrionis* gene or the three cryIA(c) genes.

The newly-discovered *B. thuringiensis* strains JHCC 4835 and JHCC 4353 show a significantly different specificity of insecticidal activity as compared with DSM 2803. In particular, 4835 and 4353 show selective activity against Lepidopteran larvae unlike known coleopteran-active *B. thuringiensis* strains. On the molecular level, the newly discovered gene in *Bacillus thuringiensis* strains JHCC 4835 and 4353 and the truncated form of this gene encode gene products which show significantly different specta of insecticidal activity as compared with the coleopteran-specific endotoxin gene product from DSM 2803 or the lepidopteran-specific cryIA endotoxin gene product from HD-1 and other var. *kurstaki* strains.

The new endotoxin gene encodes an 81.2 kilodalton endotoxin that has a completely novel activity spectrum: it is toxic to both lepidopteran and coleopteran larvae. The truncated portion of this new endotoxin gene encodes for an insecticidal protein which is not less than 537 amino acids.

The *Bacillus thuringiensis* strains according to the invention may be prepared in any quantity required by fermenting a sample of NCIB 40091 or 40090 obtained from the National Collections of Industrial and Marine Bacteria under suitable conditions in an appropriate medium. Such conditions and media are well known to the art. The media will, for example, generally contain a nitrogen source (eg fish protein) and a carbohydrate source such as starch. Suitable conditions include a temperature in the range 15–45° C., and an approximately neutral pH. Fermentation may be conveniently carried out in batches, typically for periods of 3–5 days.

*E. coli* strains carrying cloned endotoxin genes according to the invention may be prepared by growing cells to stationary phase on solid nutrient media (e.g., L agar) prior to scraping cell growth from the medium surface, lyophilizing, and freezing before thawing and weighing out the insecticidal material.

Insecticidal compositions according to the invention may be obtained from the fermentation liquor by concentration, for example by centrifugation or filtration followed by addition of any desired and appropriate formulating agents. Formulating agents which may be useful include for example surface active agents, eg, wetting agents: solid diluents, dispersing agents and UV stabilizers. If desired, solid formulations may be prepared by known methods.

The process of the invention is generally carried out by treating (eg spraying) plants infested or liable to infestation by insects with insecticidal compositions as described above diluted with a diluent such as water. The insecticidal agent is the toxic δ-endotoxin: if desired this may be applied to the plants or insects infesting them independently of the bacteria that produce it. Separation of the endotoxin protein from the bacterium *E. coli,* is however generally not necessary when the gene is expressed. For genes not expressed, the protein is preferably separated from the crystal.

Another method of carrying out the process of the invention is to arrange for the plant susceptible to insect attack to produce the δ-endotoxin in situ. This is done by cloning a δ-endotoxin gene from strain NCIB 40090 or NCIB 40091, by known means; providing it with a promoter sequence (for example the CaMV35S promoter) which will cause expression of the gene in plants; and transforming the plant by known methods. Suitable transformation methods may include the use of Ti plasmid vectors for Agrobacterium-mediated transformation of dicots, or direct DNA uptake methods such as embryo microinjection, or use of microprojectiles followed by plant regeneration. To obtain the greatest degree of expression of the gene the promoter sequence should be selected and engineered appropriately and other factors (for example codon usage) should be adapted to maximize expression in planta.

Lepidopteran larvae which are combatted by the process of the invention may include those listed in Table 5.

TABLE 5

| Common Name | Lating Name |
|---|---|
| Tobacco budworm | *Heliothis virescens* |
| Corn earworm | *Heliothis zea* |
| European corn borer | *Ostrinia nubilalis* |
| Cabbage looper | *Trichoplusia ni* |
| Diamondback moth | *Plutella xylostella* |
| Fall army worm | *Spodoptera frugiperda* |
| Beet army worm | *Spodoptera exigua* |

The process of the invention may be used to protect a wide variety of plants prone to infestation by Lepidoptera and Coleoptera. Specific examples of commercially important plants to be protected by the invention are maize (corn), tomatoes, potatoes, cotton, tobacco and cucurbits.

*Bacillus thuringiensis* JHCC 4835 and 4353 are var. *kurstaki* strains according to tests with antibody to flagellar antigens. These strains and indeed other *kurstaki* strains previously described (e.g. strain A20 deposited at the National Collections of Industrial and Marine Bacteria under accession number NCIB 12570 and the subject of prior UK application no 8730132 filed 24 December 1987) are active against Lepidoptera. If the 81 kD endotoxin gene is used as a hybridization probe, strongly hybridizing sequences can be found in both chromosomal and plasmid DNA samples from other known *Bacillus thuringiensis* strains. These strains include var. *kurstaki* strains such as HD-1, HD-73 and HD-241, and the var. *kenvae* strain HD-123. In spite of this, the 81 kD endotoxin gene has not been previously described, or recognized as being present in these or other *Bacillus thurinaiensis* strains than 648 amino acids and not less than 536 amino acids.

The invention may be further understood with reference to the accompanying drawings, in which:

FIG. 1 shows diagrammatically the derivation of the cloned 81 kD endotoxin gene in the recombinant plasmid pJH11;

FIG. 2 shows diagrammatically the structure of pJH11, and the structures of the coleopteran-specific tenebrionis-type gene and the CryA 6.6-type gene cloned into the same vector system (PT712) and designated pIC 226 and pIC 228 respectively;

FIG. 3 shows diagrammatically the structure of the cloned lepidopteran-specific endotoxin gene in the recombinant plasmid pJH12;

FIG. 4 shows diagrammatically the structure of the cloned lepidopteran-specific endotoxin gene in the recombinant lambda clone CL5;

FIGS. 5A–5U show the base sequence (SEQ ID NO:1), the amino acid sequence (SEQ ID NO:2) and the main restriction endonuclease recognition sites of the 81 kD endotoxin gene carried by pJH11;

FI. 6A–6J shows the base sequence (SEQ ID NO:3) of the truncated cryV gene pIC224N1 encoding for 648 amino acids (SEQ ID NO:4). The amino acid sequence and the main restriction sites of the gene are readily determined by comparison of FIGS. 6A–6K with FIGS. 5A–5U.

FIG. 7A–7I shows the base sequence (SEQ ID NO:5) of the truncated cryV gene pIC224E5 encoding for the 535 amino acid (SEQ ID NO:6) which is not an active insecticidal protein.

FIG. 8 shows a schematic representation of the full-length cryV gene in pIC224, and the truncated versions in pIC224N1 and pIC224E5. Restriction sites used for cloning are EcoRV, NdeI, and SacI. The solid bars denote the five blocks of amino acids that share homology among cryI, –III, –IV, and V genes FIGS. 9A–9C explains the cloning strategy for the truncation of cryV.

FIG. 10 shows a visualization of CryV proteins in feeding assay supernatants.

FIGS. 11A–11K shows an optimized version of the wild type cryV DNA sequence (SEQ ID NO:7) encoding for the same amino acids (SEQ ID NO:8) as the wild type cryV gene.

DESCRIPTION OF THE PREFERRED EMBODIMENTS OF THE INVENTION

With further reference to FIG. 1, in this diagram, which is not drawn to scale, N represents restriction endonuclease NdeI, H=HindIII, E=EcoR1, D=DraI and S=SmaI. Restriction sites above the maps are in the cloned DNA, whereas sites below the maps are in the vector. Parentheses indicate sites rendered non-functional by "filling-in" with Klenow DNA polymerase. Dashed lines represent pUC19 vector DNA. Dotted Lines represent PT712 vector DNA in clone pJH11 and the arrowhead represents the bacteriophage T7 promoter. The star represents a $^{32}$P-labelled DNA fragment.

In FIG. 2, the figures below the maps represent the number of basepairs between the T7 RNA polymerase transcriptional start site and the beginning of the open reading frame. The large arrowhead represents the bacteriophage T7 promoter. The solid block in PT712 represents the cloning site; H=HindIII and S=SmaI. $Ap^r$ indicates the gene encoding resistance to ampicillin.

In FIG. 3, the open box represents the cloned fragment which is about 7 kilobasepairs in length. The dashed lines indicate pUC19 vector DNA and Ap$^R$ is the gene encoding ampicillin resistance. The parentheses indicate an NdeI site which is only provisionally placed in the region shown; other restriction sites are represented by D=DraI, E=EcoR1, H=HindIII and N=NdeI.

Figure 4:
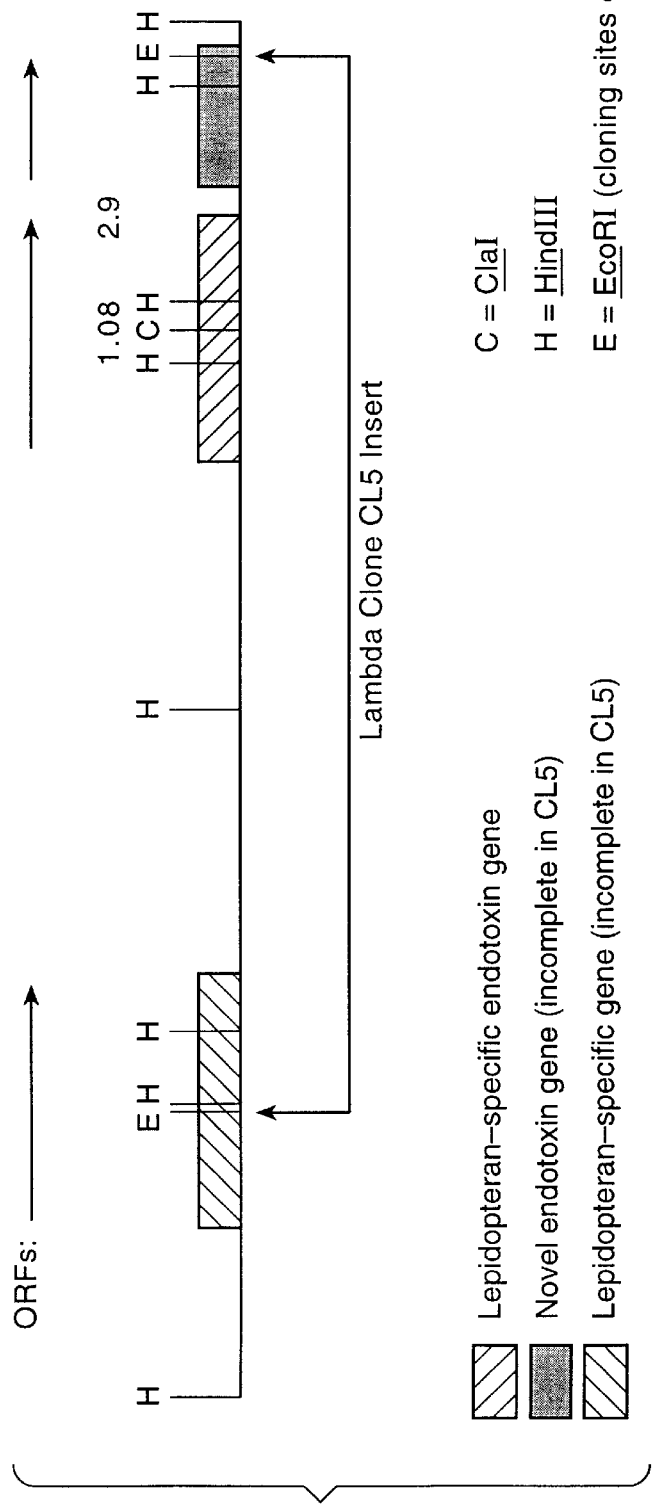

With reference to FIG. 4, the only EcoR1 (E) sites shown are those at which the Lambda vector and the cloned insert fragment are joined. Open reading frames (ORFs) are shown by arrows above the map. The numbers above the map are the approximate fragment lengths of selected HindIII fragments. The ClaI (C) site shown is not the only ClaI site in the insert. The diagram is not drawn to scale; the cloned insert fragment is approximately 16 kilobase pairs in length.

FIGS. 5A–5U show the base sequence, the amino-acid sequence and the main restriction sites of the gene encoding the 81 kD endotoxin protein and flanking DNA. The open reading frame begins at base number 355 and ends at base number 2514 with the G of the termination (Ter) codon TAG.

This new endotoxin gene (cryV) encodes an insecticidal control protein. This new gene cryV like cryI, cryIII and cryIV have five blocks of conserved amino acid sequence. Amino acid sequence alignment by conserved regions reveals that size differences between cryIA, cryIIIA and cryV are due to the number of amino acids extending past the fifth conserved domain of cryV. The present invention included a truncated form of the CryV protein which is insecticidal. This truncated insecticidal protein permits a synthetic gene to be formed with less DNA sequence than the wild-type (untruncated) gene. Synthetic genes are used in transformation of plants such as corn to permit the AT rich BT gene to be optimized to a GC rich gene.

Based on the wild type vs. synthetic gene difference the following definition of substantially homologous recombinant DNA is defined as a DNA sequence that encodes for a protein having substantially the same insecticidal properties evidenced by the protein in FIGS. 6A–6J. To determine the insecticidal property of a protein a person of ordinary skill in the art would follow the teachings of the following examples and feed the expressed protein to susceptible insects of the orders Coleoptera and Lepidoptera and compare the results with the data herein. If the results are similar and the amino acids in the five conserved blocks are substantially similar to those listed herein then the definition is met.

The insecticidal activity of the truncated form of the CryV protein is shown herein. Specifically the insecticidal activity against *Ostrinia nubilalis* (European corn borer) herein has been determined.

The truncated form of the CryV protein remains insecticidal to ECB larvae after 71 amino acids were deleted from the C-terminus.

Figure 8:
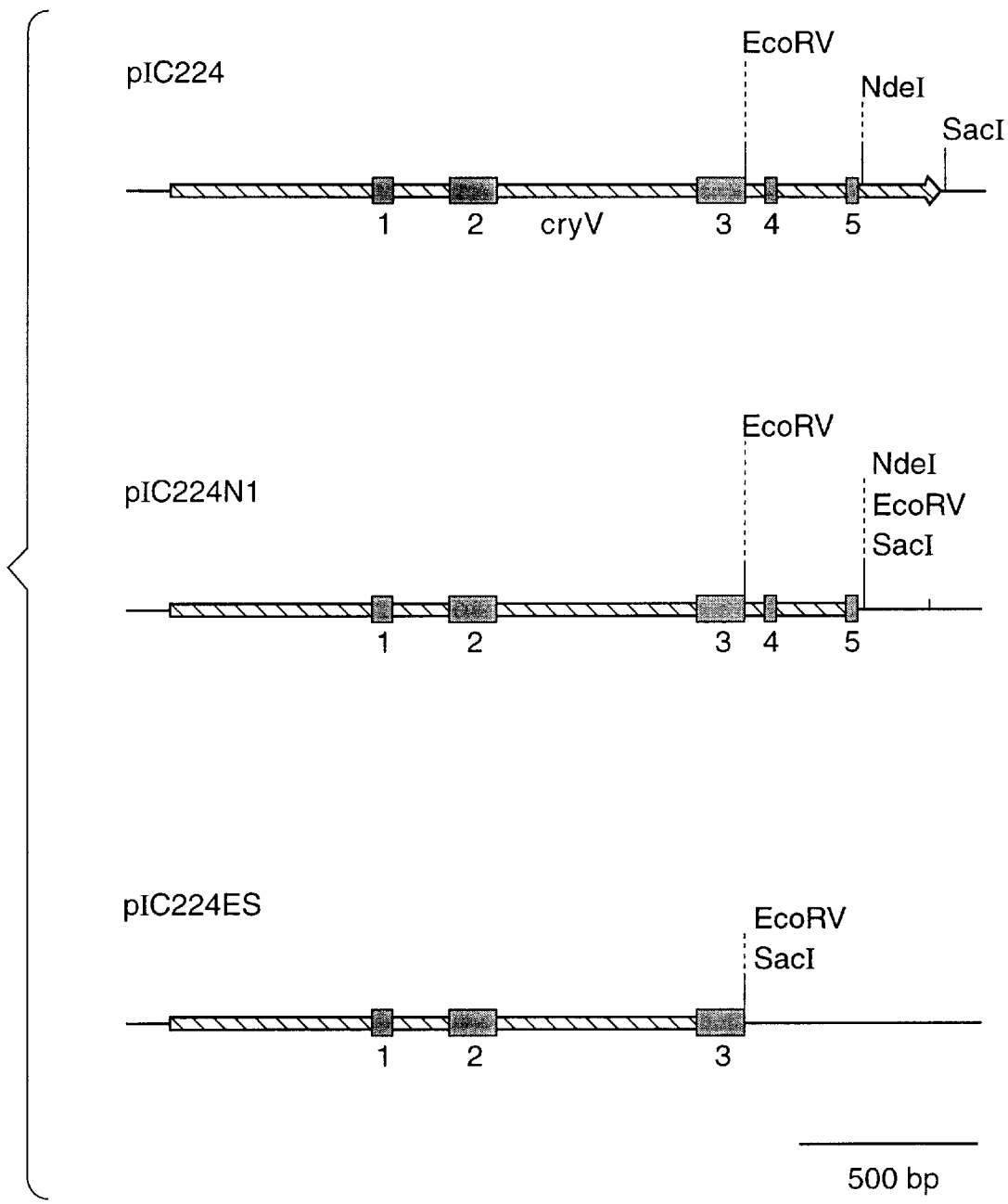

The truncations at the carboxyl end of the cryV gene were achieved via cloning. Plasmid pIC224 containing the full-length cryV gene (FIG. 8) was digested with NdeI and SacI (SstI) restriction enzymes. A linker comprised of the following oligonucleotides: 5' CCTAGATATCTCACTCA 3', 5' TATGAGTGAGATATCTAGGAGCT 3', (SEQ ID NO:9 and SEQ ID NO:10, respectively), which provided an in-frame stop codon, an EcoRV site, and a second stop codon, was cloned into the NdeI and SacI sites. The resulting plasmid, named pIC224N1, encoded 648 amino acids of the CryV protein and ended five amino acids downstream of the fifth homologous block (FIGS. 9A–9C). Plasmid pIC224N1 was digested with EcoRV and religated to form pIC224E5, which encoded 535 amino acids of the CryV protein, and ended at the three-prime-end of the third homologous block (FIG. 8). Constructs were verified by restriction analysis and transformed into *E. coli* BL21DE3.

The Western blot was probed with antibody against CryV to determine the presence of the cryV-gene. Total protein (about 5.0 ug/lane) from recombinant *E. coli*lysates pIC224, pIC224N1, pIC224E5, and pIC234 were run on a 10% SDS-PAGE, transferred to a nitrocellulose membrane, and probed with antibodies raised against the CryV protein. Differences in size among full-length (224), first truncation (N1), and second truncation (E5) are readily apparent.

Western blot analysis of proteins found in recombinant *E. coli* lysates revealed that clones pIC224N1 and pIC224E5 produced truncated CryV proteins as predicted. The results of the experiments run demonstrated that the truncated protein encoded by pIC224N1 remained insecticidal to ECB larvae, while the protein encoded by pIC224E5 lost its toxicity completely. The mortality that resulted from pIC224N1 was slightly less than that of the full-length CryV protein, this could be because the pIC224N1 is less toxic, however, the expression of the truncated pIC224N1 was less than the full-length pIC224. The data indicates that the fourth and fifth homologous blocks of sequence located between the EcoRV and NdeI sites of the cryV gene are essential for insecticidal activity.

It is not known if the 81.2 kDa CryV insecticidal control protein (ICP) is processed in any way. Other *B. thuringiensis* endotoxins are processed by proteases associated with the insect gut, or *B. thurinciensis* itself. The present invention clearly evidences that the deletion that ended five amino acids downstream of the fifth block (pIC224N1) did not eliminate toxicity.

The function of the CryV amino acid sequence beyond the fifth homologous block is unclear. In the instance of the 135 kDa CryIA proteins, the carboxyl half of the protein is thought to be involved in crystal formation. However, the CryV protein was not detected in preparations of solubilized crystal proteins from *B. thurinaiensis* subsp. *kurstaki* in Western blot analyses. In fact, reported cryV genes are a distal part of an operon located approximately 500 bp 3' of a cryI-type gene, and they are expressed either weakly or not at all because of an intergenic transcriptional terminator and a lack of an upstream promoter-like sequence.

We have herein demonstrated that the CryV protein remained insecticidal to ECB larvae after 71 amino acids were deleted from the C-terminus. When 184 amino acid residues were deleted, the insecticidal function was lost.

It has been recognized that placing wild type genes such as evidenced in FIGS. 5A–5U into plants through known transformation techniques often shows less than desirable expression levels in the plant. Thus it is often preferred to create a synthetic optimized gene which is GC rich instead of AT rich. Optimization of a synthetic gene is a lengthy process which can result in a number of various nucleic acids sequences all of which encode for the desired amino acids which form the protein. An example of an optimized nucleic acid sequence which encodes for a similar protein which the wild type cryV encodes for is shown in FIGS. 11A–11K. In FIGS. 11A–11K the amino acids are listed above the corresponding nucleotides in this Figure.

The gene, optimized as described above in FIGS. 11A–11K can be introduced into plants by a variety of approaches (particle bombardment, electroporation, polyethylene glycol treatment of protoplasts, or whiskers). In addition to the plasmid carrying the optimized gene, cells are also transformed with a DNA fragment containing a gene which can serve as a selectable or screenable marker. Such a marker fragment DNA can be located on the same DNA fragment as the optimized gene or on a separate DNA fragment. Transformed cells can be readily separated from non-transformed cells by culturing on a selective medium, and plants carrying the optimized gene can be regenerated from the selected cells.

As an example, whiskers, U.S. Pat. No. 5,302,523, can be used to effect uptake of DNA into maize cells. The pat gene can be used as the selectable marker although other marker genes can also be used. The optimized coding sequence, under the control of a promoter sequence capable of directing expression of the coding sequence in the plant cell, together with suitable 3' transcription regulatory signals, functions in the maize cells to produce insecticidal levels of protein. European corn borer larvae fed transformed cells became stunted in development and die.

The following Examples illustrate the invention.

EXAMPLE 1

Isolation of the B. thuringiensis strain JHCC 4835 according to the invention.

Soil samples were diluted by placing 5.0 g of the sample into 45 ml of 0.5% peptone to give a $10^{-1}$ dilution prior to emulsification. The sample was then heated to 60° C. for 10 minutes in a water bath. Sequential dilutions were then made prior to plating 0.1 ml of the $10^{-3}$ and $10^{-5}$ dilutions onto B. cereus selective agar plates (Bacillus cereus agar base, Oxoid) and esculin agar plates (in g/liter of $H_2O$: esculin 1.0; ferric citrate 0.5; peptone 10; NaCl 5; Oxoid agar 10). The plated samples were incubated at 30° C. for 5 days. Slides were made of potential B. thurinaiensis colonies, stained according to Smirnoff's procedure and examined microscopically at 1000× magnification for the presence of stained, parasporal crystals.

Crystal-positive colonies were streaked onto L agar (10 g tryptone, 10 g yeast extract, 5 g NaCl, 10 g agar per liter) in order to ensure a pure culture, and incubated at 30° C. Purified colonies were incubated overnight in L broth; after incubation an equal volume of 80% sterile glycerol was added prior to storage at −70° C.

The strain JHCC 4353 was extracted by a similar procedure.

EXAMPLE 2

Propagation of the B. thuringiensis strains JHCC 4835 and JHCC 4353 on solid media.

Inoculum was transferred from a glycerol storage vial onto an L agar plate to check for purity. A representative sweep of colonies was then used to inoculate 5 ml of broth (10 g tryptone, 10 g yeast extract, 5 g NaCl per liter) prior to incubation with shaking at 30° C. for 3–5 hours. One milliliter of this culture was then used to inoculate a preparative (210 mm×210 mm) Petri plate containing 300 ml of CRL 1 medium agar (in g or ml/liter of water: nutrient broth 8; glucose 6; yeast extract 5; xylose 0.5; cotton seed flour extract 30 ml; corn steep liquor 3.2 ml; Mary Mendells salt mixture 1 ml; Oxoid agar 15). Mary Mendel's salt mixture is:

| Mary Mendel's Salts | |
|---|---|
| Distilled Water | 495 ml |
| HCl conc. | 5 ml |
| $FeSO_4$ | 2.5 g |
| $MnSO_4, H_2O$ or $MnCl_2.4H_2O$ | 0.98 g |
| $ZnCl_2$ or $ZnSO_4.4H_2O$ | 1.76 g |

Cultures were incubated for 5 days at 30° C. The cells, spores and crystals were then harvested by scraping confluent growth from the agar surface prior to freeze-drying.

EXAMPLE 3

Propagation of the B. thuringiensis strain JHCC 4835 and JHCC 4353 in liquid culture according to the invention.

Inoculum was transferred from a glycerol storage vial to a 250 ml Erylenmeyer flask containing 100 ml of CRL 1 medium (in g or ml/liter of water: nutrient broth 8; glucose 6; yeast extract 5; xylose 0.5; cotton seed flour extract 30 ml; corn steep liquor 3.2 ml; Mary Mendel's salt mixture 1 ml) and incubated with agitation at 30° C. and 3400 rpm. After 24 hours, the entire 100 ml was used to inoculate 1 liter of the same medium in a 2L flask; this was incubated with agitation for 5 days at 30° C. The cells, spores and crystals were then harvested by centrifugation and acetone precipitated using the Dulmage method.

EXAMPLE 4

Formulation according to the invention.

Upon completion of the fermentation cycle, JHCC 4353 or JHCC 4835 bacteria can be harvested by first separating the B. thurinaiensis spores and crystals from the fermentation broth as described in Example 2. The recovered spores and crystals can be resuspended in 100 ml of water and formulated into a liquid concentrate by adding 4.9 g of Morwet D-425 (dispersing agent), 4.9 g of Veegum HV (suspending agent), 4.9 ml of Tween 80 (wetting agent) and 24.4 ml of Sorbo (anti-freezing agent). Each ingredient is added separately in order stated above. The product is kept at 40° C. prior to use.

EXAMPLE 5

Cloning of plasmid-derived endotoxin genes from B. thuringiensis strain 4835.

Endotoxin genes are cloned from covalently closed circular (ccc) plasmid DNA prepared from B. thurinaiensis strain 4835 as follows:

A 500 ml culture of strain 4835 is grown in L broth at 37° C., with shaking, to an absorbance value at 600 mm of 1.00 optical density (O.D) units. Cells are harvested by centrifugation at 8000 revolutions per minute (rpm) for 10 minutes at 4° C., then re-suspended in 5 ml TE buffer [50 mM Tris HCl pH7.6, 20 mM EDTA). The resuspended cells are added to 95 ml of TE buffer containing 1% sodium dodecyl sulphate (SDS) and 0.085M NaOH, pH12.4 lysin of the cell suspension occurs during an incubation at room temperature. 10 ml of 10% SDS are then added to the lysate; the solution is mixed gently prior to the gradual addition of 10 ml 2M Tris HCl pH7.0 with gentle mixing. 34 ml of 5M NaCl is added and the solution is mixed well prior to overnight incubation on ice-water. The lysate is centrifuged at 9000 rpm for 15 minutes at 4° C. and the supernatant carefully transferred to a new centrifuged bottle prior to the addition of m 50% polyethylene glycol (PEG) 600 in TE buffer. The lysate is incubated on ice-water for 3 hours (minimum) to overnight prior to centrifugation at 10,000 rpm for 10 minutes at 4° C. The pellet is dissolved in 9 ml TE buffer and 100ul 5mg/ml RNA (treated at 100° C. for 5 minutes, prior to use) and incubated at 45° C. for 10 minutes, prior to the addition of 9.23 g caesium chloride (CsCl). After CsCl is dissolved, 0.9 ml of 5 mg/ml ethidium bromide is added prior to isopyonic centrifugation of the mixture at 40,000 rpm for 48 hours at 15° C., and isolation of the ccc DNA band. After removal of the CsCl and ethidium bromide by conventional techniques, high molecular weight plasmid ccc DNA (greater then 40 kilobase pairs) is isolated by size fractionation on 10%–40% sucrose step gradients prior to digestion with appropriate restriction endonucleases (ie, those which do not cleave the DNA in the endotoxin structural gene), ligation into appropriately digested plasmid cloning vectors (eg pUC18 or pUC19), and transformation into an appropriate E. coli host strain (the specific strain used is MC1022, which is an ampicillin-sensitive strain of the genotype ara D139, Δ(ara, leu) 7697, Δ(lac Z) M15, gal U, gal K, str A). Transformants resistant to appropriate antibiotics which select for the introduced plasmid vector were then screened for recombinant endotoxin genes by standard DNA hybridization methods, using as probes the cloned tenebrionis gene (plus flanking sequences) and a cloned cryIA gene.

EXAMPLE 6

Cloning of chromosomal endotoxin genes from *B. thurinaiensis* strain 4835.

Endotoxin genes were cloned from chromosomal DNA prepared from strain 4835 as follows:

A 500 ml culture of strain 4835 was grown in L-broth at 37° C., with shaking, to an Absorbance value at 600 nm of 1.00 optical density units. Cells were harvested by centrifugation at 8000 rounds per minute (rpm) for 10 minutes at 4° C., then re-suspended in 5 ml TES buffer (50mM Tris-HCl pH7.5, 50 mM NaCl, 5mM EDTA). Cells were treated for 30 minutes at 37° C. with lysozyme (0.5 mg/ml final concentration) and RNase (0.1 mg/ml final concentration taken from a stock solution of 5 mg/ml boiled at 100° C. for 5 minutes prior to use). Lysis was completed by the addition of Sarcosyl to give a final concentration of 0.8% and incubation at 37° C. for 60 minutes in the presence of Pronase (0.5 mg/ml final concentration taken from a stock solution of 5 mg/ml pre-incubated at 37° C. for 60 minutes prior to use). Lysate volume was adjusted to 9.0 ml in the 50 mM Tris-HCl pH7.6, 10 mM EDTA, prior to the addition of 9.2 g caesium chloride (CsCl). After the CsCl dissolved, 1.25 ml of the 5 mg/ml solution of ethidium bromide was added prior to isopyonic centrifugation of the mixture at 40,000 rpm for 48 hours at 15° C.

After removal of CsCl and ethidium bromide by conventional techniques, an aliquot of purified chromosomal DNA was partially digested with the restriction endonuclease EcoR1 prior to ligation into EcoR1-digested bacteriophage λ EMBL4 vector DNA. Ligation reaction mixtures were packaged into viable phage particles using a commercially-available kit from Amersham International PLC.

The resultant recombinant phage particles were selected by growth on *E. coli* host strain PE392, a P2 lysogen of strain LE392 which has the genotype hsd R514 ($r_K^-$, $M_K^+$), sup E44, sup F58, lacY1 or Δ (lac12Y), gal K2, gal T22, met B1, trp R55. Recombinant phage carrying one or more endotoxin genes were detected by hybridization of lysed phaques fixed to a duplicate set of nitrocellulose filters using as probes radiolabelled fragments of a CryIA-endotoxin gene and a 3'-terminal fragment of the gene for the 81 kD protein.

Plaques containing endotoxin genes were purified and characterized by restriction endonuclease mapping techniques well known in the art.

Chromosomal endotoxin genes can also be cloned directly into plasmid vectors (e.g. pUC19). This may necessitate cloning the gene in small fragments by the technique well known in the art as "chromosome walking". Problems with deletion events due to host-mediated homologous recombination can be circumvented by cloning in this manner and reconstructing the desired open reading frame by piecing the gene together after sequencing an appropriate number of overlapping gene fragments.

EXAMPLE 7

Solid media propagation of insecticidally-active *E. coli* strains carrying cloned endotoxin genes according to the invention.

Inoculum was transferred from a glycerol storage vial to L agar Petri plates containing antibiotics suitable for selection of the cloning vector. Inoculated plates were incubated 24–72 hours to allow for the appearance of characteristic colonial morphology. A selection of single colonies of the correct appearance (e.g. rough colonies in the case of *E. coli* strain BL21/pJH11 carrying the cloned the 81 kD endotoxin gene) was used to inoculate a small volume of L broth [15 g Tryptone, 7.5 yeast extract, 7.5 g NaCl per 1500 ml total volume] containing an antibiotic (e.g. ampicillin) suitable for selection for the plasmid vector carrying the cloned endotoxin gene. Cultures were grown to an Absorbance value at 600 nm of 0.5–0.7 O.D. units. One milliliter (ml) of culture was used to inoculate, by spreading with a glass "spreader", a preparative (i.e. 245 mm×245 mm×20 mm) Petri plate containing L agar [L broth as above supplemented with 16 g Oxoid agar, an appropriate antibiotic and IPTG to a final concentration of 120 microgram/ml.]. Preparative plates were incubated overnight at 37° C. Bacterial growth was scraped from the preparative plates using a glass spreader. The scraped product, pooled from several plates if necessary, was transferred to a sterile plastic container and frozen for 2 hours at −20° C. prior to lyophilization for 16–18 hours. The material was stored at −20° C. The dried product is crushed into an even powder prior to use as an insecticidal material in insect bioassays.

EXAMPLE 8

Purification of the novel 81.2 kilodalton endotoxin protein from the recombinant *E. coli* strain MC1022/pJH11. *E. coli* strain MC1022/pJH11 was prepared on solid media as described in Example 7, but the scraped cell mass was stored at −20° C. without lyophilization. Frozen cells were thawed on ice prior to disruption by sonication at an amplitude of 14 microns for 9×20 seconds using a 1 cm diameter probe. The sonicated cells were then centrifuged at 9300×g at 4° C. to remove unbroken cells, prior to high-speed centrifugation (100,000×g for 60 minutes at 4° C.) to remove membranes. The high-speed extract was then subjected to ion-exchange chromatography over DEAE-Sepharose at pH 8.0. The column was then eluted with a 0–500 mM NaCl gradient, and fractions monitored by SDS-PAGE. Fractions containing the 81.2 kD protein were pooled, dialyzed against 10 mM Tris pH8.0, and subjected to a second FPLC ion-exchange chromatography step, again eluting the bound proteins with a 0–500 mM NaCl gradient. Fractions containing the partially-purified 81.2 kD protein were identified and pooled prior to further purification by gel filtration chromatography. This process results in an endotoxin protein which is 90% pure and which may be used (with or without a concentration step) in insect bioassays.

Examples 9 and 10 illustrate the activity of the novel *B. thuringiensis* strains of the invention against different Diabrotica spp.

EXAMPLE 9

Specificity of insecticidal activity of *B. thuringiensis* strains JHCC 4835 and JHCC 4353.

A mixture of spores and crystals was prepared by incubating the organism at 30° C. for 5 days on 210 mm×210 mm Petri plates as in Example 2, scraping confluent growth from the agar surface and freeze-drying. Freeze-dried spores and crystals were mixed with a sterile 2.5% sucrose solution for tests on first-instar. Freeze-dried spores and crystals were mixed with sterile $H_2O$ and presented on potato leaves dipped in this suspension for tests on first-instar Colorado potato beetle (*Leptinotarsa decemlineata*) larvae. Freeze-dried spores and crystals were mixed with sterile $H_2O$ and presented on cotton cotyledons dipped in this suspension for tests on Boll Weevil (*Anthonomus arandis*) adults. The efficacy of these preparations at various concentrations in parts per million (ppm) is shown in Table 6. Comparison on the activity spectrum *B. thuringiensis* variety *tenebrionis* (DSM 2803) with those of strains JHCC 4835 and JHCC 4353 shows the more selective effect of the latter two strains (Table 6).

The efficacy of *B. thurinciensis* strain JHCC 4835 in the control of various lepidopteran larvae is illustrated in Examples 10–13.

EXAMPLE 10

Efficacy of *B. thuringiensis* strain JHCC 4835 in the control of various lepidopteran larvae.

A mixture of spores and crystals was prepared as in Example 2, and mixed with an appropriate conventional artificial insect diet. Comparison of the efficacy of *B. thuringiensis* variety *tenebrionis* (DSM 2803) with that of strain JHCC 4835 shows that only strain 4835, and the known var. *kurstaki* strain JHCC 4360, are insecticidal to lepidopteran larvae (Table 7).

EXAMPLE 11

Efficacy of *B. thuringiensis* strain JHCC 4835 in the control of Fall Army Worm (*Spodoptera fruailerda*).

A mixture of spores and crystals was prepared as in Example 2, and mixed with an appropriate conventional artificial insect diet. Results are shown in Table 8 below. Comparison of the efficacy of *B. thuringiensis* strain JHCC 4580 (an isolate very similar to var. *tenebrionis*) with that of strain JHCC 4835 shows that only strain 4835, and the known *kurstaki* strain JHCC 4360, are insecticidal to *S. fruainerda* (Table 8).

EXAMPLE 12

Efficacy of *B. thuringiensis* strain JHCC 4835 in the control of Beet Army Worm (*Spodoptera exigua*).

A mixture of spores and crystals was prepared as in Example 2, and mixed with an appropriate conventional artificial insect diet. Results are shown in below. Comparison of the efficacy of *B. thuringiensis* strains JHCC 4580 (an isolate very similar to var. *tenebrionis*) with that of strain JHCC 4835 shows that only strain 4835, and the known *kurstaki* strain JHCC 4360, are insecticidal to *S. exicua*.

EXAMPLE 13

Efficacy of *Bacillus thurinaiensis* strains JHCC 4835 and 4353 in the control of *Heliothis virescens*.

A mixture of spores and crystals was prepared as in Example 2, and mixed with an appropriate conventional artificial insect diet. Control of larvae obtained is shown in Table 10 below.

The efficacy and novel larvacidal activity spectrum of recombinant *E. coli* cells carrying the cloned endotoxin gene encoding the 81.2 kD protein are illustrated in Examples 14–16.

EXAMPLE 14

Efficacy of the larvacidal activity of the 81 kD endotoxin expressed by recombinant *E. coli* strain MC1022/pJH11 in controlling European Corn Borer (*Ostrinia nubilalis*).

*E. coli* strain MC1022/pJH11 was prepared on solid media as described in Example 7. Freeze-dried cells were thawed-and mixed with an appropriate conventional artificial insect diet to give the final treatment concentration in parts per million (ppm) shown in Table 11. Tests were infested with first instar European corn borer larvae and evaluated at 6 days after treatment (DAT). *E. coli* strains carrying the recombinant plasmid with the 81 kD endotoxin gene (pJH11) and those carrying the cryIA 6.6 type lepidopteran-specific gene (pIC228) were insecticidal, whereas those carrying the vector only (PT712) or the *tenebrionis*-type gene (pIC226) were not.

EXAMPLE 15

Efficacy of the larvacidal activity of the 81 kD endotoxin expressed by recombinant *E. coli* strain MC1022/pJH11 in controlling Colorado Potato Beetle (*Leptinotarsa decemlineata*).

*E. coli* strain-MC1022/pJH11 was prepared on solid media as described in Example 7. Freeze-dried cells were thawed, mixed with sterile $H_2O$ and presented on potato leaves dipped in this suspension for tests on first-instar larvae of Colorado Potato Beetles (*Leptinotarsa decemlineata*) to give the final treatment concentration in parts per million (ppm) shown in Table 12. *E. coli* strains carrying the recombinant plasmid with the 81 kD endotoxin gene (pJH11) and those carrying the *tenebrionis*-type gene (pIC226) were insecticidal whereas those carrying the vector only (PT712) or the cryIA 6.6 type *lepidopteran*-specific gene (pIC228) were not.

EXAMPLE 16

Efficacy of the larvacidal activity of the partially-purified and purified 81 kD endotoxin in controlling European Corn Borer (*Ostrinia nubilalis*).

Partially-purified and purified 81 kD endotoxin protein was prepared from freeze-dried recombinant *E. coli* cells MC1022/pJH11 as described in Example 8. Fractions from the second FPLC ion-exchange column were designated MonoQ A, B, and C and contained about 50%, 50%, and 25% 81.2 kD endotoxin protein respectively. These fractions were added to conventional artificial insect diet to give the treatment rates in ppm shown in Table 13 in bioassays to test insecticidal activity on first-instar larvae of European corn borer (*Ostrinia nubilalis*). The results in Table 13 show that all fractions were active in producing either mortality or stunting of larval growth Purified 81.2 kD protein was also tested and found to be insecticidal to European corn borer larvae and to stunt larval growth (Table 14).

EXAMPLE 17

Efficacy of the larvacidal activity of the partially-purified and purified 81 kD endotoxin in controlling Colorado Potato Beetle (*Leptinotarsa decemlineata*).

Partially-purified and purified 81.2 kD endotoxin protein was prepared from freeze-dried recombinant *E. coli* cells MC1022/pJH11 as described in Example 8. Fractions from the second, FPLC ion-exchange column were designated MonoQ A, B, and C and contained about 50%, 50%, and 25% 81.2 kD endotoxin protein respectively. These fractions and the purified 81.2 kD protein were mixed with sterile $H_2O$ and presented on potato leaves dipped in this suspension for tests on first-instar larvae of Colorado Potato Beetles (*Leptinotarsa decemlineata*) to give the final treatment concentration in parts per million (ppm) show in Table 15. The results in Table 15 shown that all fractions were insecticidal to Colorado Potato Beetle larvae.

EXAMPLE 18

C. terminal truncations of the cryV gene and their effect on insecticidal activity.

The truncations at the carboxyl end of the cryV gene were achieved via cloning. Plasmid DNA was grown in and cloned into Subcloning Efficiency DH5α™ Competent Cells (GIBCO BRL) according to the manufacturer, and isolated according to the manufacturer QIAGEN. Restriction enzymes, ligase, and procedures for restriction digestions and ligations were performed according to the manufacturer NEW ENGLAND BioLabs. Plasmid pIC224 containing the full-length cryV gene was digested with NdeI and SacI (SstI) restriction enzymes (FIG. 9A). A linker synthesized by NATIONAL BIOSCIENCES (NBI) and consisting of the following bases (SEQ ID NO:10 and SEQ ID NO:9)

```
                   stop EcoRV stop
       5' TATGAGTGAGATATCTAGGAGCT 3'

3'    ACTCACTCTATAGATCC      5'
``` was cloned into the NdeI and SacI sites (FIGS. 9A and 9B). The resulting plasmid, named pIC224N1 (FIGS. 8 & 9B), encoded 648 amino acids of the CryV protein (FIGS. 6A–6J). Plasmid pIC224N1 was digested with EcoRV and relegated to form pIC224E5 (FIGS. 8 and 9C), which encoded 535 amino acids of the CryV protein. Constructs were transformed via electroporation into *E. coli* BL21DE3 with a Gene Pulser Apparatus (165–2076) BIORAD hooked up to a Pulse Controller (165–2098) BIORAD. Cuvettes with a 0.2 cm electrode gap (165–2086) BIORAD were used and the protocol from Current Protocols in Molecular Biology Ausubel et al., Wiley-Interscience, pg 1.8.4, New York was followed.

For Western blot analyses, 10 ul of supernatant from *E. coli* lysates were mixed with 90 ul of sample buffer (0.0625M Tris pH 6.8, 2% SDS, 10% glycerol, 0.001% bromphenol blue, 5% 2-β-mercaptoethanol). The mixture was vortexed, boiled, and quenched on ice. Extracts (5 ul) were electrophoresed on a 10% sodium dodecyl sulfate polyacrylamide gel (SDS-PAGE) according to the instructions of Bio-Rad Mini-Protean II Dual Slab Cell apparatus. Proteins were transferred to Hybond-C Super (Amersham) in the Mini Trans-Blot Electrophoretic Transfer Cell (Bio-Rad). The blot was then probed by the method described in the manual for the Amersham ECL chemiluminescent detection kit (RPN 2108). A CryV antibody in rabbit serum served as the primary antibody, while the secondary antibody (donkey anti-rabbit IgG coupled to horseradish peroxidase) was supplied by the above kit, as were the HRP-based chemiluminescent detection reagents. The bound luminescent antibodies were visualized on X-ray film (Kodak XAR).

Lysates from recombinant *E. coli* were incorporated into an ECB artificial diet and fed to ECB neonates. Essentially, recombinant *E. coli* were grown in Luria broth containing the antibiotic carbenicillin (100 ug/ml) and IPTG (120 ug/ml) until stationary phase, then the bacterial pellet was lyophilized and pulverized. The dry powder was resuspended in $H_2O$ and the suspension was sonicated for three to four minutes. Supernatant (10 ul) from this mixture was set aside for use on a Western blot. Bacterial lysate was incorporated into the diet, resulting in a final concentration of 5000 ug of cell mass per ml of diet. Treatments were equally distributed among ten replications of three larvae/dish. The bioassay was held for six days at 23° C. prior to scoring for mortality and larval growth.

Figure 10:
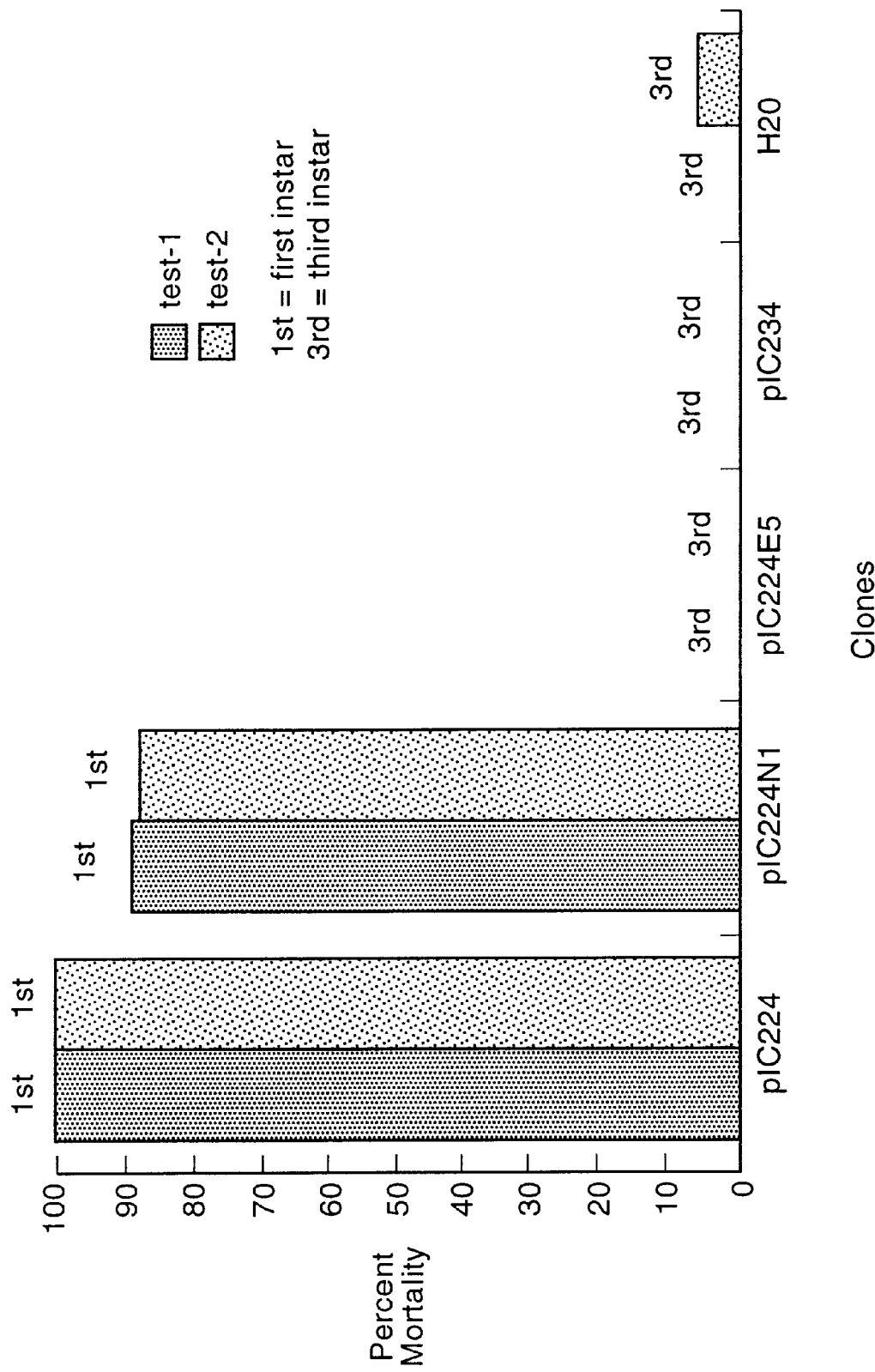

The results from this and a second representative experiment are displayed in FIG. 10. Each experiment consisted of four treatments: 1) pIC224, 2) pIC224N1, 3) pIC224E5, 4) and pIC234. As a control the cryV gene in pIC234 contains a proline hinge that disrupts the protein's secondary structure and renders it non-insecticidal to ECB larvae. The results of these experiments indicate that while the deletion of 213 basepairs has little effect on toxicity, the deletion of 551 base pairs abolished the insecticidal activity of the cryV gene. Thus the insecticidal protein necessary for expression in plants or for habitat application can be a smaller and therefore more easily formed protein then previously discovered.

EXAMPLE 19

Introduction of the optimized cryV gene into plants.

Maize cells were transformed with the optimized gene listed in FIG. 17 which had a promoter, an intron, and a selection marker in the plasmid. The cells grown in N6 medium, containing 6 mM L-proline, 2% (w/v) sucrose, 2 mg/l 2,4-dichlorophenoxyacetic acid (2,4-D) and 0.3% (w/v) Gelrite (Carolina Biological Supply Company, Burlington, N.C., USA) at pH 6.0; and these cells were bombarded with gold particles coated with DNA.

The cells, incubated in dark 28° C., were allowed to express the protein and then the cells were fed to ECB neonates. One neonate per plate was fed for 3–4 days in dim light at 23° C. There after instar larvae development was evaluated. The results are shown in Table 9. The control which was used contains corn cells which were transformed with a different plasmid. This plasmid did not contain any insecticidal gene but had the same promoter, intron and selectable marker as the cryV gene. Looking at the data on table 9 it can be seen that on day four, the larvea in the control were evaluated and the results showed all larvae at the second instar stage except one which was on the side of the container. This larvae was at the first instar stage. The surviving larvae fed the insecticidally transformed cells, on the fourth day were all at the first instar stage. Two of the larvae feeding on transformed cells were close to the molt stage and one instar was dead.

Replication of the experiment resulted in almost the same results, all larvae at the first instar stage by day four, but two larvae feeding on the transformed cells died and one reached the second instar stage (though this larva did not appear to be feeding). The controlled replication results on day four showed basically all larvae at the second instar stage.

Thus the optimized cryV gene shown in FIGS. 11A–11K was expressing protein in maize cells which resulted in stunting the growth of the ECB larvae.

The following microorganisms and clones referred to in this specification have been deposited at the National Collections of Industrial and Marine Bacteria, 23 St. Machar Drive, Aberdeen AB2 1RY, Scotland:

| Name | Deposit Number | Date |
|---|---|---|
| *Bacillus thuringiensis* | | |
| A20 | 12570 | 20 October 1987 |
| JHCC 4835 | 40091 | 7 December 1988 |
| JHCC 4353 | 40090 | 7 December 1988 |
| *E. coli* | | |
| BL21/pJH11 | 40275 | 6 April 1990 |
| MC1022/pJH12 | 40278 | 24 April 1990 |
| Bacteriophage Lambda EMBL4 clone | | |
| CL5 | 40279 | 26 April 1990 |

TABLE 1

MORPHOLOGY

| Strain | Crystals | Cell Morphology | Colony Morphology (Cultured on *Bacillus Cereus* selective Agar) |
|---|---|---|---|
| HD-1 | Medium bipyramids plus undefined shaped crystals | Rods with terminal spores which do not distend the cell | Large colonies, yellow centres. Egg yolk lecithinase: NEGATIVE |
| DMS 2803 | Small irregular crystals; few bipyrimidal crystals | Rods with terminal spores with do not distend the cell | Large Colonies, blue centres. Egg yolk lecithinase: NEGATIVE |
| JHCC 4353 | Large, mainly regular bipyrimidal crystals | Rods with oval, terminal or subterminal spores which do not distend the cell | Large blue colonies with yellow centres. Egg yolk lecithinase: POSITIVE |
| JHCC 4835 | Large, mainly regular bipyrimidal crystals | Rods with oval, terminal or subterminal spores which do not distend the cell | Large blue colonies with yellow centres Egg yolk lecithinase POSITIVE |

TABLE 2

Biochemical Markers on Microtitre Plate

| Reagent | HD-1 | DSM 2803 | JHCC 4353 | JHCC 4835 |
|---|---|---|---|---|
| Glycerol | − | − | − | − |
| Erythritol | − | − | − | − |
| D-arabinose | − | − | − | − |
| L-arabinose | − | − | − | − |
| Ribose | + | +/− | + | + |
| D-xylose | − | − | − | − |
| L-xylose | − | − | − | − |
| Adonitol | − | − | − | − |
| β-methyl-xyloside | − | − | − | − |
| Galactose | − | − | − | − |
| D-glucose | + | + | + | + |
| D-fructose | + | + | + | + |
| D-mannose | − | + | − | − |
| L-sorbose | − | − | − | − |
| Rhamnose | − | − | − | − |
| Dulcitol | − | − | − | − |
| Inositol | − | − | − | − |
| Mannitol | − | − | − | − |
| Sorbitol | − | − | − | − |
| α-methyl-D-mannoside | − | − | − | − |
| α-methyl-D-glucoside | − | − | − | − |
| N acetyl glucosamine | + | + | + | + |
| Amygdaline | − | − | − | − |
| Arbutine | + | + | + | + |
| Esculine | + | +/− | + | + |
| Salicine | + | − | + | + |
| Cellobiose | + | − | + | + |
| Maltose | + | + | + | + |
| Lactose | − | − | − | − |
| Melibiose | − | − | − | − |
| Saccharose | − | + | − | − |
| Trehalose | + | + | + | + |
| Inuline | − | − | − | − |
| Melezitose | − | − | − | − |
| D-raffinose | − | − | − | − |
| Amidon | + | + | + | + |
| Glycogene | + | + | + | + |
| Xylitol | − | − | − | − |
| β-gentiobiose | − | − | − | − |
| D-turanose | − | − | − | − |
| D-lyxose | − | − | − | − |
| D-tagatose | − | − | − | − |
| D-fucose | − | − | − | − |
| L-fucose | − | − | − | − |
| D-arabitol | − | − | − | − |
| L-arabitol | − | − | − | − |
| Gluconate | − | − | − | − |
| 2-ceto-gluconate | − | − | − | − |
| 5-ceto-gluconate | − | − | − | − |
| Ortho-nitro-phenyl galactoside (ONPG) | − | − | − | − |
| Arginine (ADC-arginine dihydrolase) | + | + | + | + |
| Lysine (LDH-lysine Decarboxylase) | + | − | − | − |
| Sodium Citrate (citrate utilisation) | − | + | + | + |
| Sodium Thiosulphate ($H_2S$ production) | − | − | − | − |
| Urea (urease) | + | − | + | + |
| Tryptophane (deaminase detection) | − | − | − | − |
| Tryptophane (indole production) | − | − | − | − |
| Sodium Pyruvate (VP) | + | + | + | + |
| Gelatine (Gelatinase) | + | + | + | + |
| $NO_3$—$NO_2$ Reduction | + | − | + | + |
| Ornithine decarboxylase (ODC) | − | − | − | − |

+ = Positive Reaction
− = Negative Reaction
+/− = Weak Reaction

TABLE 3

Biochemical Markers on ID-IDENT Plates

| Reagent | HD-1 | DSM 2803 | JHCC 4353 | JHCC 4835 |
|---|---|---|---|---|
| 2-naphthyl-phosphate | − | − | − | − |
| 2-naphthyl-butyrate | + | + | + | + |
| 2-naphthyl-caprylate | + | + | + | + |
| 2-naphthyl-myristate | + | + | + | + |
| L-leucyl-2-naphthylamide | + | + | + | + |
| L-valyl-2-naphthylamide | + | + | + | + |
| L-cystyl-2-naphthylamide | + | + | + | + |
| N-benzoyl-DL-arginine-2-naphthylamide | 0 | + | + | + |
| N-glutaryl-phenylalanine-2-naphthylamine | 0 | + | + | + |
| 2-naphthyl-phosphate | + | + | + | + |
| naphthol-AS-B1-phosphate | + | + | + | + |

| Reagent | HD-1 | DSM 2830 | JHCC 4353 | JHCC 4835 |
|---|---|---|---|---|
| 6-bromo-2-naphthyl-αD-galactopyranoside | − | − | − | − |
| 2-naphthyl-βD-galactopyranoside | − | − | − | − |
| Naphtol-AS-B1-βD glucuronide | − | − | − | − |
| 2-naphthyl-αD-glucopyranoside | + | + | + | + |
| 6-bromo-2-naphthyl-βD-glucopyranoside | + | − | + | + |
| 1-naphthyl-N-acetyl-βD-glucosaminide | − | − | − | − |
| 6-Bromo-2-naphthyl-αD-mannopyranoside | − | − | − | − |
| 2-naphthyl-αL-fucopyranoside | − | − | − | − |

ID-IDENT is a Trade Mark of API Analytab Products

TABLE 4

SENSITIVITIES TO ANTIBIOTICS

| STRAIN | C | CT | F | SF | NA | AMP | S | TET | OA | K | VA | RIF | LI | CN | CR | CAR | E |
|---|---|---|---|---|---|---|---|---|---|---|---|---|---|---|---|---|---|
| HD-1 | S | R | S | S | S | R | S | S | S | S | S | S | S | S | S | S | S |
| DSM 2803 | S | R | S | R | S | R | S | S | S | R | S | S/R | S | S | S | R | S |
| JHCC 4353 | S | R | S | S | S | R | S | S | S | S | S | S | S | S | S | R | S |
| JHCC 4835 | S | R | S | S | S | R | S | S | S | S | S | S | S | S | S | R | S |

S = SENSITIVE  R = RESISTANT  S/R = REDUCED SENSITIVITY
C = Chloramphenicol 50 ug/ml  CT = Colistin Sulphate 10 ug/ml
F = Nitrofuration 200 ug/ml  SF = Sulphfurazole 500 ug/ml
NA = Naladixic Acid 30 ug/ml  AMP = Ampicillin 25 ug/ml
S = Streptomycin 25 ug/ml  CR = Cephaloridine 25 ug/ml
TET = Tetracycline 50 ug/ml  K = Kanamycin 30 ug/ml
VA = Vancomycin 30 ug/ml  RIF = Rifampicin 2 ug/ml
OA = Oxolinic Acid 2 ug/ml  LI = Lincomycin 15 ug/ml
CN = Centamicin 10 ug/ml  CAR = Carbenicillin 100 ug/ml
E = Erythromycin 10 ug/ml

TABLE 6

| Bt Strain | Boll Weevil | Colorado Potato Beetle |
|---|---|---|
|  | 3 DAT 1200 ppm | 3 DAT 200 ppm |
| DSM 2803 tenebrionis | 87 | 100 |
| 4835 | 13 | 7 |
| 4353 | 13 | 0 |
| Control | 20 | 0 |

RESULTS = % MORTALITY
DAT = DAYS AFTER TREATMENT

TABLE 7

| Bt Strain | Rate (ppm) | H. zea | T. ni | P. xylostella |
|---|---|---|---|---|
| 4360 kurstaki | 5 | 85 | 95 | 100 |
| 4835 | 25 | 100 | 100 | 100 |
|  | 250 | 100 | — | — |
| 4580 tenebrionis type | 25 | 0 | 0 | 0 |
|  | 250 | 5 | — | — |
| Control | — | 0 | 0 | 10 |

RESULTS = % MORTALITY AT 4 DAYS AFTER TREATMENT

TABLE 8

Bt STRAINS VERSUS Spodoptera Frugiperda AT 6 DAYS AFTER TREATMENT

|  | 4580 tenebrionis | 4835 | 4360 kurstaki | Control |
|---|---|---|---|---|
| PREP 1 | 0 | 92 | 84 | 3 |
| PREP 2 | 0 | 60 | 80 | 3 |
| PREP 3 | 0 | 92 | 88 | 3 |
| PREP 4 | 8 | 100 | 100 | 3 |

TABLE 8-continued

Bt STRAINS VERSUS Spodoptera Frugiperda
AT 6 DAYS AFTER TREATMENT

| 4580 tenebrionis | 4835 | 4360 kurstaki | Control |
|---|---|---|---|

RESULTS EXPRESSED AS % MORTALITY AT 80 PARTS PER MILLION

TABLE 9

| Neonates | Control | 3 Days | 4 Days |
|---|---|---|---|
| Cells Transformed with cry V optimized Gene (FIG. 17) | | | |
| 1 | | D | D |
| 2 | | 1st–2nd | 1st–2nd |
| 3 | | 1st | 1st |
| 4 | | 1st | 1st |
| 5 | | 1st | 1st–2nd |
| 6 | | 1st | 1st |
| 7 | | 1st | 1st |
| 8 | | 1st | 1st |
| 9 | | 1st | 1st |
| 10 | | 1st | ** |
| Cells Transformed with Plasmid (not containing insecticidal gene) | | | |
| 1 | | 1st–2nd | 2nd |
| 2 | | 2nd | 2nd |
| 3 | | 2nd | 2nd |
| 4 | | 2nd | 2nd |
| 5 | | 2nd | 2nd |
| 6 | | 1st | 1st–2nd |
| 7 | | 1st | 2nd |
| 8 | | 1st | 2nd |
| 9 | | 2nd | 2nd |
| 10 | | 2nd | 2nd |
| REPLICATION | | | |
| Cells Transformed with cry V optimized Gene (FIG. 17) | | | |
| 1 | | 1st | 2nd |
| 2 | | D | D |
| 3 | | 1st | 1st |
| 4 | | 1st | 1st |
| 5 | | D | D |
| 6 | | 1st | 1st |
| 7 | | 1st | 1st |
| 8 | | 1st | 1st |
| 9 | | 1st | 1st |
| 10 | | 1st | 1st |
| Cells Transformed with Plasmid (not containing insecticidal gene) | | | |
| 1 | | 1st–2nd | 2nd |
| 2 | | 2nd | 2nd |
| 3 | | 2nd | 2nd |
| 4 | | 2nd | 2nd |
| 5 | | 2nd | 2nd |
| 6 | | 1st | 1st–2nd |
| 7 | | 1st | 2nd |
| 8 | | 1st | 2nd |
| 9 | | 2nd | 2nd |
| 10 | | 2nd | 2nd |

D = Dead
1st instar stage = 1st
2nd instar stage = 2nd
** = no data

TABLE 10

B.t. STRAINS VERSUS *Heliothis Zea*
AT 6 DAYS AFTER TREATMENT

| | 4580 tenebrionis | | 4835 | | 4360 kurstaki | |
|---|---|---|---|---|---|---|
| | 1 | 2 | 1 | 2 | 1 | 2 |
| PREP 1 | 4 | 8 | 100 | 96 | 100 | 100 |
| PREP 2 | 4 | 0 | 60 | 34 | 96 | 100 |
| PREP 3 | 9 | 0 | 100 | 100 | 100 | 100 |
| PREP 4 | 0 | 4 | 100 | 100 | 100 | 100 |

CONTROL 1 = 3.5%
CONTROL 2 = 2%
RESULTS EXPRESSED AS % MORTALITY AT 80 PARTS PER MILLION

TABLE 11

EUROPEAN CORN BORER BIOASSAYS

| 1ST Experiments | Prep Number | | | | | |
|---|---|---|---|---|---|---|
| Rate/% R.S. | 1 | 2 | 5 | 6 | 7 | 8 |
| pIC228 500 ppm | 30 | 30 | 63 | 5 | 10 | 75 |
| % R.S. | 100 | 100 | 100 | 100 | 100 | 100 |
| pJH11 500 ppm | 15 | 75 | 85 | 72 | 85 | 80 |
| % R.S. | 100 | 100 | 100 | 100 | 100 | 100 |
| pIC226 500 ppm | 0 | 0 | 10 | 5 | 0 | 10 |
| % R.S. | 0 | 0 | 11 | 6 | 0 | 0 |
| PT712 500 ppm | 0 | 0 | 10 | 0 | 0 | 0 |
| % R.S. | 0 | 0 | 17 | 5 | 0 | 0 |
| Control | 0 | 0 | 8 | 3 | 0 | 8 |
| % R.S. | 0 | 3 | 11 | 0 | 0 | 3 |
| 4835F2 10 ppm | — | — | 100 | 90 | 80 | 100 |
| % R.S. | — | — | xxx | 100 | 100 | xxx |

RESULTS = % MORTALITY AT 6 DAT
% R.S. = % SURVIVORS OF REDUCED SIZE

TABLE 12

COLORADO POTATO BEETLE BIOASSAYS

| | | PREP NUMBER | | | | | |
|---|---|---|---|---|---|---|---|
| SAMPLE | RATE | 1 | 2 | 5 | 6 | 7 | 8 |
| pIC226 | 5000 ppm | 84 | 84 | 60 | 53 | 27 | 93 |
| pJH11 | 5000 ppm | 84 | 100 | 60 | 93 | 79 | 87 |
| PT712 | 5000 ppm | 0 | 17 | 7 | 14 | 7 | 14 |
| pIC228 | 5000 ppm | 0 | 4 | 13 | 7 | 0 | 23 |
| Control | — | 0 | 0 | 7 | 7 | 0 | 13 |
| 4580F2 | 40 ppm | — | — | 100 | 93 | 100 | 73 |

RESULTS = % MORTALITY AT 3 DAYS AFTER TREATMENT

TABLE 13

EUROPEAN CORN BORER BIOASSAY AT 6 DAYS AFTER TREATMENT

| Rate (ppm) | Prep | NON-TREATMENT CONTROLS Pre | NON-TREATMENT CONTROLS Post | (% MORTALITY/AVE. SIZE IN mm) MonoQ Fractions A | (% MORTALITY/AVE. SIZE IN mm) MonoQ Fractions B | (% MORTALITY/AVE. SIZE IN mm) MonoQ Fractions C | B.t. STRAIN 4835 |
|---|---|---|---|---|---|---|---|
| 113 | 1 | — | — | 88/1.5 | | | |
| 98 | 2 | | | | | 56/1.75 | |
| 67 | 1 | | | | | 66/1.5 | |
| 65 | 2 | | | | | 67/1.8 | |
| 65 | 3 | | | | | 78/1.5 | |
| 62 | 1 | | | | 100/1.1 | | |
| 57 | 2 | | | | 71/2.0 | | |
| 42 | 2 | | | 89/1.5 | | | |
| 11.5 | 3 | | | | | | |
| 10 | 2 | | | | | | 78/1.75 |
| 6.5 | 2 | | | | | | 62/1.8 |
| 6.5 | 3 | | | | | 17/2.7 | |
| 6.3 | 1 | | | | | 22/3.1 | |
| 6.0 | 2 | | | | 22/2.7 | | |
| 4 | 2 | | | 0/2.4 | | | |
| 3.8 | 1 | | 11/5.4 | | | | |
| 3 | 1 | | | | | 0/5.0 | |
| — | 1 | 0/8.5 | 0/10 | | | | |
| — | 2 | 11/6.2 | 0/6.0 | | | | |
| — | 3 | 0/9.5 | 13/9.1 | | | | |

AVE SIZE IN mm = Average Size Of Surviving Larvae

TABLE 14

81kD PROTEIN VS. EUROPEAN CORN BORER

| | | | IA | JH | JH |
|---|---|---|---|---|---|
| | | Rate | % Mortality | % Mortality | Ave. Size |
| PREP 1 | | | | | |
| 81kD | Prot | 83 ppm | — | 0 | 2.7 mm |
| 17/20 | Ctrl | 5 ppm | — | 0 | 9.5 mm |
| Tris | Ctrl | — | — | 0 | 10 mm |
| PREP 2 | | | | | |
| 81kD | Prot | 16 ppm | 100 | — | — |
| | | 9.5 ppm | — | 25 | 2.1 mm |
| 17/20 | Ctrl | 5 ppm | — | 0 | 6 mm |
| Tril | Ctrl | — | — | 40 | 0 | 6 mm |

IA = IOWA, JH = JEALOTT'S HILL, CTRL = CONTROL AVE SIZE = AVERAGE SIZE OF SURVING LARVAE

TABLE 15

82kD PROTEIN VERSUS COLORADO POTATO BEETLE

| | Control | Mono Q Fractions A | Mono Q Fractions B | Mono Q Fractions C | 81k/D | B.t. Strain 4580 |
|---|---|---|---|---|---|---|
| PREP 1 | | | | | | |
| Rate (ppm): | — | 330 | 213 | 270 | — | 40 |
| | 0 | 47 | 21 | 47 | — | 80 |
| PREP 2 | | | | | | |
| Rate (ppm): | — | 466 | 366 | 342 | 148 | 40 |
| | 0 | 87 | 67 | 87 | 33 | 100 |
| PREP 3 | | | | | | |
| Rate (ppm): | — | — | — | 588 | 257 | 40 |
| | 0 | — | — | 60 | 73 | 80 |

Results = % Mortality at 3 Days After Treatmemt

We claim:

1. An isolated DNA coding for the amino acid sequence set forth in FIGS. 6A–6J (SEQ ID NO:4).

2. The isolated DNA according to claim 1 in plasmid vector deposited at the National Collections of Industrial and Marine Bacteria on Apr. 26, 1990 under the accession number 40279.

3. The isolated DNA according to claim 1 in E. coli strain BL21/pJH11 deposited at the National Collections of Industrial and Marine Bacteria under the accession number 40275.

4. The isolated DNA of claim 1 which is a gene sequence from either Bacillus thuringiensis strain JHCC 4835 or strain JHCC 4353 which have been deposited on Dec. 7, 1988 with the National Collections of Industrial and Marine Bacteria under the accession numbers NCIB 40091 and NCIB 40090, respectively.

5. An isolated DNA coding for the amino acid sequence set forth in FIGS. 11A–11K (SEQ ID NO:8).

6. The isolated DNA according to claim 5 in the plasmid vector deposited at the National Collections of Industrial and Marine Bacteria on Apr. 26, 1990 under the accession number 40279.

7. The isolated DNA according to claim 5 in E. coli strain BL21/pJH11 deposited at the national Collections of Industrial and Marine Bacteria under the accession number 40275.

8. The isolated DNA of claim 5 which is a gene sequence from either Bacillus thuringiensis strain JHCC 4835 or strain JHCC 4353 which have been deposited on Dec. 7, 1988 with the National Collections of Industrial and Marine Bacteria under the accession numbers NCIB 40091 and NCIB 40090, respectively.

9. An isolated DNA coding for amino acids 1–766 of FIGS. 5A–5U (SEQ ID NO:2).

10. The isolated DNA according to claim 9 in the plasmid vector deposited at the National Collections of Industrial and Marine Bacteria on Apr. 26, 1990 under the accession number 40279.

11. The isolated DNA according to claim 9 in *E. coli* strain BL21/pJH11 deposited at the National Collections of Industrial and Marine Bacteria under the accession number 40275.

12. The isolated DNA of claim 9 which is a gene sequence from either *Bacillus thuringiensis* strain JHCC 4835 or strain JHCC 4353 which have been deposited on Dec. 7, 1988 with the National Collections of Industrial and Marine Bacteria under the accession numbers NCIB 40091 and NCIB 40090, respectively.

13. An isolated DNA having a sequence set forth in FIGS. 6A–6J (SEQ ID NO:3).

14. An isolated DNA having a sequence set forth in FIGS. 11A–11K (SEQ ID NO:7).

15. An isolated DNA having a sequence of nucleotides 1–2298 set forth in FIGS. 5A–5U (SEQ ID NO:1).

16. A process of protecting a plant against attack by susceptible insects of the orders Coleoptera or Lepidoptera which comprises exposing said insects to a protein encoded by the DNA of claim 1.

17. A process of protecting a plant against attack by susceptible insects of the orders Coleoptera or Lepidoptera which comprises exposing said insects to a protein encoded by the DNA of claim 5.

18. A process of protecting a plant against attack by susceptible insects of the orders Coleoptera or Lepidoptera which comprises exposing said insects to a protein encoded by the DNA of claim 9.

19. The process of claim 16, wherein said plant is maize.

20. The process of claim 17, wherein said plant is maize.

21. The process of claim 18 wherein said plant is maize.

22. The process of claim 16 wherein said insect is the European corn borer.

23. The process of claim 17 wherein said insect is the European corn borer.

24. The process of claim 18 wherein said insect is the European corn borer.

25. A process of killing insects of the orders Coleoptera or Lepidoptera which comprises exposing said insects to a protein encoded by the DNA of claim 1.

26. A process of killing insects of the orders Coleoptera or Lepidoptera which comprises exposing said insects to a protein encoded by the DNA of claim 5.

27. A process of killing insects of the orders Coleoptera or Lepidoptera which comprises exposing said insects to a protein encoded by the DNA of claim 9.

28. A process of protecting plants against attack by susceptible insects of the order Coleoptera or Lepidoptera comprising exposing said insects to an endotoxin containing at least 536 contiguous amino acids of FIGS. 5A–5U (SEQ ID NO:2).

29. A process of protecting plants against attack by susceptible insects of the order Coleoptera or Lepidoptera comprising exposing said insects to an endotoxin containing at least 536 contiguous amino acids of FIGS. 6A–6J (SEQ ID NO:4).

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 2965 base pairs
      (B) TYPE: nucleic acid
      (C) STRANDEDNESS: both
      (D) TOPOLOGY: linear (xi) SEQUENCE DESCRIPTION: SEQ ID NO:1:

```
CATATGTATA GAGCAACTTA ATCAAGCAGA GATATTTTCA CCTATCGATG AAAATATCTC      60

TGCTTTTTCT TTTTTTATTT GGTATATGCT TTACTTGTAA TCGAAAATAA AGCACTAATA     120

AGAGTATTTA TAGGTGTTTG AAGTTATTTC AGTTCATTTT TAAAGAAGGT TTAAAGACGT     180

TAGAAAGTTA TTAAGGAATA ATATTTATTA GTAAATTCCA CATATATTAT ATAATTAATT     240

ATGAAATATA TGTATAAATT GAAAATGCTT TATTTGACAT TACAGCTAAG TATAATTTTG     300

TATGAATAAA ATTATATCTG AAAATTAAAT AATAGTATAA GTGGAGGGAT TAATATGAAA     360

CTAAAGAATC AAGATAAGCA TCAAAGTTTT TCTAGCAATG CGAAAGTAGA TAAAATCTCT     420

ACGGATTCAC TAAAAAATGA AACAGATATA GAATTACAAA ACATTAATCA TGAAGATTGT     480

TTGAAAATGT CTGAGTATGA AAATGTAGAG CCGTTTGTTA GTGCATCAAC AATTCAAACA     540

GGTATTGGTA TTGCGGGTAA ATACTTGGT ACCCTAGGCG TTCCTTTTGC AGGACAAGTA     600

GCTAGTCTTT ATAGTTTTAT CTTAGGTGAG CTATGGCCTA AGGGGAAAAA TCAATGGGAA     660

ATCTTTATGG AACATGTAGA AGAGATTATT AATCAAAAAA TATCAACTTA TGCAAGAAAT     720

AAAGCACTTA CAGACTTGAA AGGATTAGGA GATGCCTTAG CTGTCTACCA TGATTCGCTT     780

GAAAGTTGGG TTGGAAATCG TAATAACACA AGGGCTAGGA GTGTTGTCAA GAGCCAATAT     840

ATCGCATTAG AATTGATGTT CGTTCAGAAA CTACCTTCTT TTGCAGTGTC TGGAGAGGAG     900

GTACCATTAT TACCGATATA TGCCCAAGCT GCAAATTTAC ATTTGTTGCT ATTAAGAGAT     960

GCATCTATTT TTGGAAAAGA GTGGGGATTA TCATCTTCAG AAATTTCAAC ATTTTATAAC    1020

CGTCAAGTCG AACGAGCAGG AGATTATTCC TACCATTGTG TGAAATGGTA TAGCACAGGT    1080

CTAAATAACT TGAGGGGTAC AAATGCCGAA AGTTGGGTAC GATATAATCA ATTCCGTAGA    1140

GACATGACTT TAATGGTACT AGATTTAGTG GCACTATTTC CAAGCTATGA TACACAAATG    1200

TATCCAATTA AAACTACAGC CCAACTTACA AGAGAAGTAT ATACAGACGC AATTGGGACA    1260

GTACATCCGC ATCCAAGTTT TACAAGTACG ACTTGGTATA ATAATAATGC ACCTTCGTTC    1320

TCTGCCATAG AGGCTGCTGT TGTTCGAAAC CCGCATCTAC TCGATTTTCT AGAACAAGTT    1380

ACAATTTACA GCTTATTAAG TCGATGGAGT AACACTCAGT ATATGAATAT GTGGGGAGGA    1440

CATAAACTAG AATTCCGAAC AATAGGAGGA ACGTTAAATA TCTCAACACA AGGATCTACT    1500

AATACTTCTA TTAATCCTGT AACATTACCG TTCACTTCTC GAGACGTCTA TAGGACTGAA    1560

TCATTGGCAG GGCTGAATCT ATTTTTAACT CAACCTGTTA ATGGAGTACC TAGGGTTGAT    1620

TTTCATTGGA AATTCGTCAC ACATCCGATC GCATCTGATA ATTTCTATTA TCCAGGGTAT    1680

GCTGGAATTG GGACGCAATT ACAGGATTCA GAAAATGAAT TACCACCTGA AGCAACAGGA    1740

CAGCCAAATT ATGAATCTTA TAGTCATAGA TTATCTCATA TAGGACTCAT TTCAGCATCA    1800

CATGTGAAAG CATTGGTATA TTCTTGGACG CATCGTAGTG CAGATCGTAC AAATACAATT    1860

GAGCCAAATA GCATTACACA AATACCATTA GTAAAAGCTT TCAATCTGTC TTCAGGTGCC    1920

GCTGTAGTGA GAGGACCAGG ATTTACAGGT GGGGATATCC TTCGAAGAAC GAATACTGGT    1980

ACATTTGGGG ATATACGAGT AAATATTAAT CCACCATTTG CACAAAGATA TCGCGTGAGG    2040

ATTCGCTATG CTTCTACCAC AGATTACAA TTCCATACGT CAATTAACGG TAAAGCTATT    2100

AATCAAGGTA ATTTTTCAGC AACTATGAAT AGAGGAGAGG ACTTAGACTA TAAAACCTTT    2160

MGAACTGTAG GCTTTACCAC TCCATTTAGC TTTTTAGATG TACAAAGTAC ATTCACAATA    2220

GGTGCTTGGA ACTTCTCTTC AGGTAACGAA GTTTATATAG ATAGAATTGA ATTTGTTCCG    2280
```

-continued

```
GTAGAAGTAA CATATGAGGC AGAATATGAT TTTGAAAAAG CGCAAGAGAA GGTTACTGCA    2340

CTGTTTACAT CTACGAATCC AAGAGGATTA AAAACAGATG TAAAGGATTA TCATATTGAC    2400

CAGGTATCAA ATTTAGTAGA GTCTCTATCA GATGAATTCT ATCTTGATGA AAAGAGAGAA    2460

TTATTCGAGA TAGTTAAATA CGCGAAGCAA CTCCATATTG AGCGTAACAT GTAGAATTAA    2520

AATCTACCTA AATCCAGAAA AATAAAAGGG TTAAATATAC AATTCTTGTA CCAATATTTT    2580

GAGTGATTAG ATGTAGGATG AAATTTAATT GTATGCTATT TAACAGTAGA GATATTAAAA    2640

ATTAATTTAT CTACACATTA ATAGTATAGA CATACAAACA TAAGAGAGCA TTGTCTTTTC    2700

GTAGGCTACA ATGCTCTCTA TTTACTATTT ATTTTTCTTT TGTATCTTCA AATTGACGTT    2760

GTTCTAAGCG TTCTATTGCA GCTCGTCGTT TAGTATCATC AATGTTTGTA TAAAGAGATG    2820

TTGTTTCCAT AGAATTATGT CCCATTTGAT TTGCTAATAA TACTAAATCT TTATTTTCAT    2880

TATAGTGATT AGTAGCATAA GTATGACGTA ATTTATGAGG GCTTTTCTTT TCATCAAAAG    2940

CCCTTGTGTA TTTCTCTGTA AGCTT                                          2965
```

(2) INFORMATION FOR SEQ ID NO:2:

(i) SEQUENCE CHARACTERISTICS:
        (A) LENGTH: 2965 base pairs
        (B) TYPE: nucleic acid
        (C) STRANDEDNESS: both
        (D) TOPOLOGY: linear (ii) MOLECULE TYPE: DNA (genomic)

(ix) FEATURE:
        (A) NAME/KEY: CDS
        (B) LOCATION: 1..2965

(xi) SEQUENCE DESCRIPTION: SEQ ID NO:2:

```
CAT ATG TAT AGA GCA ACT TAA TCA AGC AGA GAT ATT TTC ACC TAT CGA         48
His Met Tyr Arg Ala Thr  *  Ser Ser Arg Asp Ile Phe Thr Tyr Arg
 1               5                  10                  15

TGA AAA TAT CTC TGC TTT TTC TTT TTT TAT TTG GTA TAT GCT TTA CTT         96
 *  Lys Tyr Leu Cys Phe Phe Phe Phe Tyr Leu Val Tyr Ala Leu Leu
             20                  25                  30

GTA ATC GAA AAT AAA GCA CTA ATA AGA GTA TTT ATA GGT GTT TGA AGT        144
Val Ile Glu Asn Lys Ala Leu Ile Arg Val Phe Ile Gly Val  *  Ser
         35                  40                  45

TAT TTC AGT TCA TTT TTA AAG AAG GTT TAA AGA CGT TAG AAA GTT ATT        192
Tyr Phe Ser Ser Phe Leu Lys Lys Val  *  Arg Arg  *  Lys Val Ile
     50                  55                  60

AAG GAA TAA TAT TTA TTA GTA AAT TCC ACA TAT ATT ATA TAA TTA ATT        240
Lys Glu  *  Tyr Leu Leu Val Asn Ser Thr Tyr Ile Ile  *  Leu Ile
 65              70                  75                  80

ATG AAA TAT ATG TAT AAA TTG AAA ATG CTT TAT TTG ACA TTA CAG CTA        288
Met Lys Tyr Met Tyr Lys Leu Lys Met Leu Tyr Leu Thr Leu Gln Leu
                 85                  90                  95

AGT ATA ATT TTG TAT GAA TAA AAT TAT ATC TGA AAA TTA AAT AAT AGT        336
Ser Ile Ile Leu Tyr Glu  *  Asn Tyr Ile  *  Lys Leu Asn Asn Ser
            100                 105                 110

ATA AGT GGA GGG ATT AAT ATG AAA CTA AAG AAT CAA GAT AAG CAT CAA        384
Ile Ser Gly Gly Ile Asn Met Lys Leu Lys Asn Gln Asp Lys His Gln
        115                 120                 125

AGT TTT TCT AGC AAT GCG AAA GTA GAT AAA ATC TCT ACG GAT TCA CTA        432
Ser Phe Ser Ser Asn Ala Lys Val Asp Lys Ile Ser Thr Asp Ser Leu
    130                 135                 140

AAA AAT GAA ACA GAT ATA GAA TTA CAA AAC ATT AAT CAT GAA GAT TGT        480
```

```
                                                        -continued

Lys Asn Glu Thr Asp Ile Glu Leu Gln Asn Ile Asn His Glu Asp Cys
145                 150                 155                 160

TTG AAA ATG TCT GAG TAT GAA AAT GTA GAG CCG TTT GTT AGT GCA TCA          528
Leu Lys Met Ser Glu Tyr Glu Asn Val Glu Pro Phe Val Ser Ala Ser
                165                 170                 175

ACA ATT CAA ACA GGT ATT GGT ATT GCG GGT AAA ATA CTT GGT ACC CTA          576
Thr Ile Gln Thr Gly Ile Gly Ile Ala Gly Lys Ile Leu Gly Thr Leu
            180                 185                 190

GGC GTT CCT TTT GCA GGA CAA GTA GCT AGT CTT TAT AGT TTT ATC TTA          624
Gly Val Pro Phe Ala Gly Gln Val Ala Ser Leu Tyr Ser Phe Ile Leu
        195                 200                 205

GGT GAG CTA TGG CCT AAG GGG AAA AAT CAA TGG GAA ATC TTT ATG GAA          672
Gly Glu Leu Trp Pro Lys Gly Lys Asn Gln Trp Glu Ile Phe Met Glu
    210                 215                 220

CAT GTA GAA GAG ATT ATT AAT CAA AAA ATA TCA ACT TAT GCA AGA AAT          720
His Val Glu Glu Ile Ile Asn Gln Lys Ile Ser Thr Tyr Ala Arg Asn
225                 230                 235                 240

AAA GCA CTT ACA GAC TTG AAA GGA TTA GGA GAT GCC TTA GCT GTC TAC          768
Lys Ala Leu Thr Asp Leu Lys Gly Leu Gly Asp Ala Leu Ala Val Tyr
                245                 250                 255

CAT GAT TCG CTT GAA AGT TGG GTT GGA AAT CGT AAT AAC ACA AGG GCT          816
His Asp Ser Leu Glu Ser Trp Val Gly Asn Arg Asn Asn Thr Arg Ala
            260                 265                 270

AGG AGT GTT GTC AAG AGC CAA TAT ATC GCA TTA GAA TTG ATG TTC GTT          864
Arg Ser Val Val Lys Ser Gln Tyr Ile Ala Leu Glu Leu Met Phe Val
        275                 280                 285

CAG AAA CTA CCT TCT TTT GCA GTG TCT GGA GAG GAG GTA CCA TTA TTA          912
Gln Lys Leu Pro Ser Phe Ala Val Ser Gly Glu Glu Val Pro Leu Leu
    290                 295                 300

CCG ATA TAT GCC CAA GCT GCA AAT TTA CAT TTG TTG CTA TTA AGA GAT          960
Pro Ile Tyr Ala Gln Ala Ala Asn Leu His Leu Leu Leu Arg Asp
305                 310                 315                 320

GCA TCT ATT TTT GGA AAA GAG TGG GGA TTA TCA TCT TCA GAA ATT TCA         1008
Ala Ser Ile Phe Gly Lys Glu Trp Gly Leu Ser Ser Ser Glu Ile Ser
                325                 330                 335

ACA TTT TAT AAC CGT CAA GTC GAA CGA GCA GGA GAT TAT TCC TAC CAT         1056
Thr Phe Tyr Asn Arg Gln Val Glu Arg Ala Gly Asp Tyr Ser Tyr His
            340                 345                 350

TGT GTG AAA TGG TAT AGC ACA GGT CTA AAT AAC TTG AGG GGT ACA AAT         1104
Cys Val Lys Trp Tyr Ser Thr Gly Leu Asn Asn Leu Arg Gly Thr Asn
        355                 360                 365

GCC GAA AGT TGG GTA CGA TAT AAT CAA TTC CGT AGA GAC ATG ACT TTA         1152
Ala Glu Ser Trp Val Arg Tyr Asn Gln Phe Arg Arg Asp Met Thr Leu
    370                 375                 380

ATG GTA CTA GAT TTA GTG GCA CTA TTT CCA AGC TAT GAT ACA CAA ATG         1200
Met Val Leu Asp Leu Val Ala Leu Phe Pro Ser Tyr Asp Thr Gln Met
385                 390                 395                 400

TAT CCA ATT AAA ACT ACA GCC CAA CTT ACA AGA GAA GTA TAT ACA GAC         1248
Tyr Pro Ile Lys Thr Thr Ala Gln Leu Thr Arg Glu Val Tyr Thr Asp
                405                 410                 415

GCA ATT GGG ACA GTA CAT CCG CAT CCA AGT TTT ACA AGT ACG ACT TGG         1296
Ala Ile Gly Thr Val His Pro His Pro Ser Phe Thr Ser Thr Thr Trp
            420                 425                 430

TAT AAT AAT AAT GCA CCT TCG TTC TCT GCC ATA GAG GCT GCT GTT GTT         1344
Tyr Asn Asn Asn Ala Pro Ser Phe Ser Ala Ile Glu Ala Ala Val Val
        435                 440                 445

CGA AAC CCG CAT CTA CTC GAT TTT CTA GAA CAA GTT ACA ATT TAC AGC         1392
Arg Asn Pro His Leu Leu Asp Phe Leu Glu Gln Val Thr Ile Tyr Ser
    450                 455                 460
```

```
TTA TTA AGT CGA TGG AGT AAC ACT CAG TAT ATG AAT ATG TGG GGA GGA        1440
Leu Leu Ser Arg Trp Ser Asn Thr Gln Tyr Met Asn Met Trp Gly Gly
465                 470                 475                 480

CAT AAA CTA GAA TTC CGA ACA ATA GGA GGA ACG TTA AAT ATC TCA ACA        1488
His Lys Leu Glu Phe Arg Thr Ile Gly Gly Thr Leu Asn Ile Ser Thr
                485                 490                 495

CAA GGA TCT ACT AAT ACT TCT ATT AAT CCT GTA ACA TTA CCG TTC ACT        1536
Gln Gly Ser Thr Asn Thr Ser Ile Asn Pro Val Thr Leu Pro Phe Thr
            500                 505                 510

TCT CGA GAC GTC TAT AGG ACT GAA TCA TTG GCA GGG CTG AAT CTA TTT        1584
Ser Arg Asp Val Tyr Arg Thr Glu Ser Leu Ala Gly Leu Asn Leu Phe
        515                 520                 525

TTA ACT CAA CCT GTT AAT GGA GTA CCT AGG GTT GAT TTT CAT TGG AAA        1632
Leu Thr Gln Pro Val Asn Gly Val Pro Arg Val Asp Phe His Trp Lys
530                 535                 540

TTC GTC ACA CAT CCG ATC GCA TCT GAT AAT TTC TAT TAT CCA GGG TAT        1680
Phe Val Thr His Pro Ile Ala Ser Asp Asn Phe Tyr Tyr Pro Gly Tyr
545                 550                 555                 560

GCT GGA ATT GGG ACG CAA TTA CAG GAT TCA GAA AAT GAA TTA CCA CCT        1728
Ala Gly Ile Gly Thr Gln Leu Gln Asp Ser Glu Asn Glu Leu Pro Pro
                565                 570                 575

GAA GCA ACA GGA CAG CCA AAT TAT GAA TCT TAT AGT CAT AGA TTA TCT        1776
Glu Ala Thr Gly Gln Pro Asn Tyr Glu Ser Tyr Ser His Arg Leu Ser
            580                 585                 590

CAT ATA GGA CTC ATT TCA GCA TCA CAT GTG AAA GCA TTG GTA TAT TCT        1824
His Ile Gly Leu Ile Ser Ala Ser His Val Lys Ala Leu Val Tyr Ser
        595                 600                 605

TGG ACG CAT CGT AGT GCA GAT CGT ACA AAT ACA ATT GAG CCA AAT AGC        1872
Trp Thr His Arg Ser Ala Asp Arg Thr Asn Thr Ile Glu Pro Asn Ser
610                 615                 620

ATT ACA CAA ATA CCA TTA GTA AAA GCT TTC AAT CTG TCT TCA GGT GCC        1920
Ile Thr Gln Ile Pro Leu Val Lys Ala Phe Asn Leu Ser Ser Gly Ala
625                 630                 635                 640

GCT GTA GTG AGA GGA CCA GGA TTT ACA GGT GGG GAT ATC CTT CGA AGA        1968
Ala Val Val Arg Gly Pro Gly Phe Thr Gly Gly Asp Ile Leu Arg Arg
                645                 650                 655

ACG AAT ACT GGT ACA TTT GGG GAT ATA CGA GTA AAT ATT AAT CCA CCA        2016
Thr Asn Thr Gly Thr Phe Gly Asp Ile Arg Val Asn Ile Asn Pro Pro
            660                 665                 670

TTT GCA CAA AGA TAT CGC GTG AGG ATT CGC TAT GCT TCT ACC ACA GAT        2064
Phe Ala Gln Arg Tyr Arg Val Arg Ile Arg Tyr Ala Ser Thr Thr Asp
        675                 680                 685

TTA CAA TTC CAT ACG TCA ATT AAC GGT AAA GCT ATT AAT CAA GGT AAT        2112
Leu Gln Phe His Thr Ser Ile Asn Gly Lys Ala Ile Asn Gln Gly Asn
690                 695                 700

TTT TCA GCA ACT ATG AAT AGA GGA GAG GAC TTA GAC TAT AAA ACC TTT        2160
Phe Ser Ala Thr Met Asn Arg Gly Glu Asp Leu Asp Tyr Lys Thr Phe
705                 710                 715                 720

MGA ACT GTA GGC TTT ACC ACT CCA TTT AGC TTT TTA GAT GTA CAA AGT        2208
Arg Thr Val Gly Phe Thr Thr Pro Phe Ser Phe Leu Asp Val Gln Ser
                725                 730                 735

ACA TTC ACA ATA GGT GCT TGG AAC TTC TCT TCA GGT AAC GAA GTT TAT        2256
Thr Phe Thr Ile Gly Ala Trp Asn Phe Ser Ser Gly Asn Glu Val Tyr
            740                 745                 750

ATA GAT AGA ATT GAA TTT GTT CCG GTA GAA GTA ACA TAT GAG GCA GAA        2304
Ile Asp Arg Ile Glu Phe Val Pro Val Glu Val Thr Tyr Glu Ala Glu
        755                 760                 765

TAT GAT TTT GAA AAA GCG CAA GAG AAG GTT ACT GCA CTG TTT ACA TCT        2352
Tyr Asp Phe Glu Lys Ala Gln Glu Lys Val Thr Ala Leu Phe Thr Ser
770                 775                 780
```

```
ACG AAT CCA AGA GGA TTA AAA ACA GAT GTA AAG GAT TAT CAT ATT GAC      2400
Thr Asn Pro Arg Gly Leu Lys Thr Asp Val Lys Asp Tyr His Ile Asp
785                 790                 795                 800

CAG GTA TCA AAT TTA GTA GAG TCT CTA TCA GAT GAA TTC TAT CTT GAT      2448
Gln Val Ser Asn Leu Val Glu Ser Leu Ser Asp Glu Phe Tyr Leu Asp
                805                 810                 815

GAA AAG AGA GAA TTA TTC GAG ATA GTT AAA TAC GCG AAG CAA CTC CAT      2496
Glu Lys Arg Glu Leu Phe Glu Ile Val Lys Tyr Ala Lys Gln Leu His
            820                 825                 830

ATT GAG CGT AAC ATG TAG AAT TAA AAT CTA CCT AAA TCC AGA AAA ATA      2544
Ile Glu Arg Asn Met  *  Asn  *  Asn Leu Pro Lys Ser Arg Lys Ile
        835                 840                 845

AAA GGG TTA AAT ATA CAA TTC TTG TAC CAA TAT TTT GAG TGA TTA GAT      2592
Lys Gly Leu Asn Ile Gln Phe Leu Tyr Gln Tyr Phe Glu  *  Leu Asp
850                 855                 860

GTA GGA TGA AAT TTA ATT GTA TGC TAT TTA ACA GTA GAG ATA TTA AAA      2640
Val Gly  *  Asn Leu Ile Val Cys Tyr Leu Thr Val Glu Ile Leu Lys
865                 870                 875                 880

ATT AAT TTA TCT ATA CAT TAA TAG TAT AGA CAT ACA AAC ATA AGA GAG      2688
Ile Asn Leu Ser Ile His  *   *  Tyr Arg His Thr Asn Ile Arg Glu
                885                 890                 895

CAT TGT CTT TTC GTA GGC TAC AAT GCT CTC TAT TTA CTA TTT ATT TTT      2736
His Cys Leu Phe Val Gly Tyr Asn Ala Leu Tyr Leu Leu Phe Ile Phe
            900                 905                 910

CTT TTG TAT CTT CAA ATT GAC GTT GTT CTA AGC GTT CTA TTG CAG CTC      2784
Leu Leu Tyr Leu Gln Ile Asp Val Val Leu Ser Val Leu Leu Gln Leu
        915                 920                 925

GTC GTT TAG TAT CAT CAA TGT TTG TAT AAA GAG ATG TTG TTT CCA TAG      2832
Val Val  *  Tyr His Gln Cys Leu Tyr Lys Glu Met Leu Phe Pro  *
930                 935                 940

AAT TAT GTC CCA TTT GAT TTG CTA ATA ATA CTA AAT CTT TAT TTT CAT      2880
Asn Tyr Val Pro Phe Asp Leu Leu Ile Ile Leu Asn Leu Tyr Phe His
945                 950                 955                 960

TAT AGT GAT TAG TAG CAT AAG TAT GAC GTA ATT TAT GAG GGC TTT TCT      2928
Tyr Ser Asp  *   *  His Lys Tyr Asp Val Ile Tyr Glu Gly Phe Ser
                965                 970                 975

TTT CAT CAA AAG CCC TTG TGT ATT TCT CTG TAA GCT T                    2965
Phe His Gln Lys Pro Leu Cys Ile Ser Leu  *  Ala
            980                 985

(2) INFORMATION FOR SEQ ID NO:3:

(i) SEQUENCE CHARACTERISTICS:
        (A) LENGTH: 1946 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1946

(xi) SEQUENCE DESCRIPTION: SEQ ID NO:3:

ATG AAA CTA AAG AAT CAA GAT AAG CAT CAA AGT TTT TCT AGC AAT GCG       48
Met Lys Leu Lys Asn Gln Asp Lys His Gln Ser Phe Ser Ser Asn Ala
1                   5                  10                  15

AAA GTA GAT AAA ATC TCT ACG GAT TCA CTA AAA AAT GAA ACA GAT ATA       96
Lys Val Asp Lys Ile Ser Thr Asp Ser Leu Lys Asn Glu Thr Asp Ile
                20                  25                  30

GAA TTA CAA AAC ATT AAT CAT GAA GAT TGT TTG AAA ATG TCT GAG TAT      144
```

```
Glu Leu Gln Asn Ile Asn His Glu Asp Cys Leu Lys Met Ser Glu Tyr
         35                  40                  45

GAA AAT GTA GAG CCG TTT GTT AGT GCA TCA ACA ATT CAA ACA GGT ATT    192
Glu Asn Val Glu Pro Phe Val Ser Ala Ser Thr Ile Gln Thr Gly Ile
     50                  55                  60

GGT ATT GCG GGT AAA ATA CTT GGT ACC CTA GGC GTT CCT TTT GCA GGA    240
Gly Ile Ala Gly Lys Ile Leu Gly Thr Leu Gly Val Pro Phe Ala Gly
 65                  70                  75                  80

CAA GTA GCT AGT CTT TAT AGT TTT ATC TTA GGT GAG CTA TGG CCT AAG    288
Gln Val Ala Ser Leu Tyr Ser Phe Ile Leu Gly Glu Leu Trp Pro Lys
                 85                  90                  95

GGG AAA AAT CAA TGG GAA ATC TTT ATG GAA CAT GTA GAA GAG ATT ATT    336
Gly Lys Asn Gln Trp Glu Ile Phe Met Glu His Val Glu Glu Ile Ile
            100                 105                 110

AAT CAA AAA ATA TCA ACT TAT GCA AGA AAT AAA GCA CTT ACA GAC TTG    384
Asn Gln Lys Ile Ser Thr Tyr Ala Arg Asn Lys Ala Leu Thr Asp Leu
            115                 120                 125

AAA GGA TTA GGA GAT GCC TTA GCT GTC TAC CAT GAT TCG CTT GAA AGT    432
Lys Gly Leu Gly Asp Ala Leu Ala Val Tyr His Asp Ser Leu Glu Ser
        130                 135                 140

TGG GTT GGA AAT CGT AAT AAC ACA AGG GCT AGG AGT GTT GTC AAG AGC    480
Trp Val Gly Asn Arg Asn Asn Thr Arg Ala Arg Ser Val Val Lys Ser
145                 150                 155                 160

CAA TAT ATC GCA TTA GAA TTG ATG TTC GTT CAG AAA CTA CCT TCT TTT    528
Gln Tyr Ile Ala Leu Glu Leu Met Phe Val Gln Lys Leu Pro Ser Phe
                165                 170                 175

GCA GTG TCT GGA GAG GAG GTA CCA TTA TTA CCG ATA TAT GCC CAA GCT    576
Ala Val Ser Gly Glu Glu Val Pro Leu Leu Pro Ile Tyr Ala Gln Ala
            180                 185                 190

GCA AAT TTA CAT TTG TTG CTA TTA AGA GAT GCA TCT ATT TTT GGA AAA    624
Ala Asn Leu His Leu Leu Leu Arg Asp Ala Ser Ile Phe Gly Lys
            195                 200                 205

GAG TGG GGA TTA TCA TCT TCA GAA ATT TCA ACA TTT TAT AAC CGT CAA    672
Glu Trp Gly Leu Ser Ser Ser Glu Ile Ser Thr Phe Tyr Asn Arg Gln
210                 215                 220

GTC GAA CGA GCA GGA GAT TAT TCC GAC CAT TGT GTG AAA TGG TAT AGC    720
Val Glu Arg Ala Gly Asp Tyr Ser Asp His Cys Val Lys Trp Tyr Ser
225                 230                 235                 240

ACA GGT CTA AAT AAC TTG AGG GGT ACA AAT GCC GAA AGT TGG GTA CGA    768
Thr Gly Leu Asn Asn Leu Arg Gly Thr Asn Ala Glu Ser Trp Val Arg
                245                 250                 255

TAT AAT CAA TTC CGT AGA GAC ATG ACT TTA ATG GTA CTA GAT TTA GTG    816
Tyr Asn Gln Phe Arg Arg Asp Met Thr Leu Met Val Leu Asp Leu Val
            260                 265                 270

GCA CTA TTT CCA AGC TAT GAT ACA CAA ATG TAT CCA ATT AAA ACT ACA    864
Ala Leu Phe Pro Ser Tyr Asp Thr Gln Met Tyr Pro Ile Lys Thr Thr
            275                 280                 285

GCC CAA CTT ACA AGA GAA GTA TAT ACA GAC GCA ATT GGG ACA GTA CAT    912
Ala Gln Leu Thr Arg Glu Val Tyr Thr Asp Ala Ile Gly Thr Val His
290                 295                 300

CCG CAT CCA AGT TTT ACA AGT ACG ACT TGG TAT AAT AAT AAT GCA CCT    960
Pro His Pro Ser Phe Thr Ser Thr Thr Trp Tyr Asn Asn Asn Ala Pro
305                 310                 315                 320

TCG TTC TCT GCC ATA GAG GCT GCT GTT GTT CGA AAC CCG CAT CTA CTC   1008
Ser Phe Ser Ala Ile Glu Ala Ala Val Val Arg Asn Pro His Leu Leu
                325                 330                 335

GAT TTT CTA GAA CAA GTT ACA ATT TAC AGC TTA TTA AGT CGA TGG AGT   1056
Asp Phe Leu Glu Gln Val Thr Ile Tyr Ser Leu Leu Ser Arg Trp Ser
            340                 345                 350
```

```
AAC ACT CAG TAT ATG AAT ATG TGG GGA GGA CAT AAA CTA GAA TTC CGA          1104
Asn Thr Gln Tyr Met Asn Met Trp Gly Gly His Lys Leu Glu Phe Arg
        355                 360                 365

ACA ATA GGA GGA ACG TTA AAT ATC TCA ACA CAA GGA TCT ACT AAT ACT          1152
Thr Ile Gly Gly Thr Leu Asn Ile Ser Thr Gln Gly Ser Thr Asn Thr
    370                 375                 380

TCT ATT AAT CCT GTA ACA TTA CCG TTC ACT TCT CGA GAC GTC TAT AGG          1200
Ser Ile Asn Pro Val Thr Leu Pro Phe Thr Ser Arg Asp Val Tyr Arg
385                 390                 395                 400

ACT GAA TCA TTG GCA GGG CTG AAT CTA TTT TTA ACT CAA CCT GTT AAT          1248
Thr Glu Ser Leu Ala Gly Leu Asn Leu Phe Leu Thr Gln Pro Val Asn
                405                 410                 415

GGA GTA CCT AGG GTT GAT TTT CAT TGG AAA TTC GTC ACA CAT CCG ATC          1296
Gly Val Pro Arg Val Asp Phe His Trp Lys Phe Val Thr His Pro Ile
            420                 425                 430

GCA TCT GAT AAT TTC TAT TAT CCA GGG TAT GCT GGA ATT GGG ACG CAA          1344
Ala Ser Asp Asn Phe Tyr Tyr Pro Gly Tyr Ala Gly Ile Gly Thr Gln
                435                 440                 445

TTA CAG GAT TCA GAA AAT GAA TTA CCA CCT GAA GCA ACA GGA CAG CCA          1392
Leu Gln Asp Ser Glu Asn Glu Leu Pro Pro Glu Ala Thr Gly Gln Pro
    450                 455                 460

AAT TAT GAA TCT TAT AGT CAT AGA TTA TCT CAT ATA GGA CTC ATT TCA          1440
Asn Tyr Glu Ser Tyr Ser His Arg Leu Ser His Ile Gly Leu Ile Ser
465                 470                 475                 480

GCA TCA CAT GTG AAA GCA TTG GTA TAT TCT TGG ACG CAT CGT AGT GCA          1488
Ala Ser His Val Lys Ala Leu Val Tyr Ser Trp Thr His Arg Ser Ala
                485                 490                 495

GAT CGT ACA AAT ACA ATT GAG CCA AAT AGC ATT ACA CAA ATA CCA TTA          1536
Asp Arg Thr Asn Thr Ile Glu Pro Asn Ser Ile Thr Gln Ile Pro Leu
                500                 505                 510

GTA AAA GCT TTC AAT CTG TCT TCA GGT GCC GCT GTA GTG AGA GGA CCA          1584
Val Lys Ala Phe Asn Leu Ser Ser Gly Ala Ala Val Val Arg Gly Pro
        515                 520                 525

GGA TTT ACA GGT GGG GAT ATC CTT CGA AGA ACG AAT ACT GGT ACA TTT          1632
Gly Phe Thr Gly Gly Asp Ile Leu Arg Arg Thr Asn Thr Gly Thr Phe
    530                 535                 540

GGG GAT ATA CGA GTA AAT ATT AAT CCA CCA TTT GCA CAA AGA TAT CGC          1680
Gly Asp Ile Arg Val Asn Ile Asn Pro Pro Phe Ala Gln Arg Tyr Arg
545                 550                 555                 560

GTG AGG ATT CGC TAT GCT TCT ACC ACA GAT TTA CAA TTC CAT ACG TCA          1728
Val Arg Ile Arg Tyr Ala Ser Thr Thr Asp Leu Gln Phe His Thr Ser
                565                 570                 575

ATT AAC GGT AAA GCT ATT AAT CAA GGT AAT TTT TCA GCA ACT ATG AAT          1776
Ile Asn Gly Lys Ala Ile Asn Gln Gly Asn Phe Ser Ala Thr Met Asn
                580                 585                 590

AGA GGA GAG GAC TTA GAC TAT AAA ACC TTT AGA ACT GTA GGC TTT ACC          1824
Arg Gly Glu Asp Leu Asp Tyr Lys Thr Phe Arg Thr Val Gly Phe Thr
            595                 600                 605

ACT CCA TTT AGC TTT TTA GAT GTA CAA AGT ACA TTC ACA ATA GGT GCT          1872
Thr Pro Phe Ser Phe Leu Asp Val Gln Ser Thr Phe Thr Ile Gly Ala
    610                 615                 620

TGG AAC TTC TCT TCA GGT AAC GAA GTT TAT ATA GAT AGA ATT GAA TTT          1920
Trp Asn Phe Ser Ser Gly Asn Glu Val Tyr Ile Asp Arg Ile Glu Phe
625                 630                 635                 640

GTT CCG GTA GAA GTA ACA TAT GAG TG                                        1946
Val Pro Val Glu Val Thr Tyr Glu
                645
```

(2) INFORMATION FOR SEQ ID NO:4:

(i) SEQUENCE CHARACTERISTICS:
    (A) LENGTH: 648 amino acids
    (B) TYPE: amino acid
    (D) TOPOLOGY: linear (ii) MOLECULE TYPE: protein (xi) SEQUENCE DESCRIPTION: SEQ ID NO:4:

```
Met Lys Leu Lys Asn Gln Asp Lys His Gln Ser Phe Ser Ser Asn Ala
 1               5                  10                  15

Lys Val Asp Lys Ile Ser Thr Asp Ser Leu Lys Asn Glu Thr Asp Ile
            20                  25                  30

Glu Leu Gln Asn Ile Asn His Glu Asp Cys Leu Lys Met Ser Glu Tyr
        35                  40                  45

Glu Asn Val Glu Pro Phe Val Ser Ala Ser Thr Ile Gln Thr Gly Ile
    50                  55                  60

Gly Ile Ala Gly Lys Ile Leu Gly Thr Leu Gly Val Pro Phe Ala Gly
65                  70                  75                  80

Gln Val Ala Ser Leu Tyr Ser Phe Ile Leu Gly Glu Leu Trp Pro Lys
                85                  90                  95

Gly Lys Asn Gln Trp Glu Ile Phe Met Glu His Val Glu Glu Ile Ile
            100                 105                 110

Asn Gln Lys Ile Ser Thr Tyr Ala Arg Asn Lys Ala Leu Thr Asp Leu
        115                 120                 125

Lys Gly Leu Gly Asp Ala Leu Ala Val Tyr His Asp Ser Leu Glu Ser
    130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Leu Arg Asp Ala Ser Ile Phe Gly Lys
        195                 200                 205

Glu Trp Gly Leu Ser Ser Ser Glu Ile Ser Thr Phe Tyr Asn Arg Gln
    210                 215                 220

Val Glu Arg Ala Gly Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
        275                 280                 285

Ala Gln Leu Thr Arg Glu Val Tyr Thr Asp Ala Ile Gly Thr Val His
    290                 295                 300

Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Ile Ser Thr Gln Gly Ser Thr Asn Thr
```

-continued

```
            370                 375                 380
Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
            435                 440                 445

Leu Gln Asp Ser Glu Asn Glu Leu Pro Pro Glu Ala Thr Gly Gln Pro
450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
            515                 520                 525

Gly Phe Thr Gly Gly Asp Ile Leu Arg Arg Thr Asn Thr Gly Thr Phe
            530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
            595                 600                 605

Thr Pro Phe Ser Phe Leu Asp Val Gln Ser Thr Phe Thr Ile Gly Ala
            610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu
                645

(2) INFORMATION FOR SEQ ID NO:5:

(i) SEQUENCE CHARACTERISTICS:
        (A) LENGTH: 1607 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1607

(xi) SEQUENCE DESCRIPTION: SEQ ID NO:5:

ATG AAA CTA AAG AAT CAA GAT AAG CAT CAA AGT TTT TCT AGC AAT GCG      48
Met Lys Leu Lys Asn Gln Asp Lys His Gln Ser Phe Ser Ser Asn Ala
1               5                  10                  15

AAA GTA GAT AAA ATC TCT ACG GAT TCA CTA AAA AAT GAA ACA GAT ATA      96
Lys Val Asp Lys Ile Ser Thr Asp Ser Leu Lys Asn Glu Thr Asp Ile
                20                  25                  30

GAA TTA CAA AAC ATT AAT CAT GAA GAT TGT TTG AAA ATG TCT GAG TAT     144
```

```
Glu Leu Gln Asn Ile Asn His Glu Asp Cys Leu Lys Met Ser Glu Tyr
         35                  40                  45

GAA AAT GTA GAG CCG TTT GTT AGT GCA TCA ACA ATT CAA ACA GGT ATT        192
Glu Asn Val Glu Pro Phe Val Ser Ala Ser Thr Ile Gln Thr Gly Ile
     50                  55                  60

GGT ATT GCG GGT AAA ATA CTT GGT ACC CTA GGC GTT CCT TTT GCA GGA        240
Gly Ile Ala Gly Lys Ile Leu Gly Thr Leu Gly Val Pro Phe Ala Gly
 65                  70                  75                  80

CAA GTA GCT AGT CTT TAT AGT TTT ATC TTA GGT GAG CTA TGG CCT AAG        288
Gln Val Ala Ser Leu Tyr Ser Phe Ile Leu Gly Glu Leu Trp Pro Lys
                 85                  90                  95

GGG AAA AAT CAA TGG GAA ATC TTT ATG GAA CAT GTA GAA GAG ATT ATT        336
Gly Lys Asn Gln Trp Glu Ile Phe Met Glu His Val Glu Glu Ile Ile
            100                 105                 110

AAT CAA AAA ATA TCA ACT TAT GCA AGA AAT AAA GCA CTT ACA GAC TTG        384
Asn Gln Lys Ile Ser Thr Tyr Ala Arg Asn Lys Ala Leu Thr Asp Leu
        115                 120                 125

AAA GGA TTA GGA GAT GCC TTA GCT GTC TAC CAT GAT TCG CTT GAA AGT        432
Lys Gly Leu Gly Asp Ala Leu Ala Val Tyr His Asp Ser Leu Glu Ser
130                 135                 140

TGG GTT GGA AAT CGT AAT AAC ACA AGG GCT AGG AGT GTT GTC AAG AGC        480
Trp Val Gly Asn Arg Asn Asn Thr Arg Ala Arg Ser Val Val Lys Ser
145                 150                 155                 160

CAA TAT ATC GCA TTA GAA TTG ATG TTC GTT CAG AAA CTA CCT TCT TTT        528
Gln Tyr Ile Ala Leu Glu Leu Met Phe Val Gln Lys Leu Pro Ser Phe
                165                 170                 175

GCA GTG TCT GGA GAG GAG GTA CCA TTA TTA CCG ATA TAT GCC CAA GCT        576
Ala Val Ser Gly Glu Glu Val Pro Leu Leu Pro Ile Tyr Ala Gln Ala
            180                 185                 190

GCA AAT TTA CAT TTG TTG CTA TTA AGA GAT GCA TCT ATT TTT GGA AAA        624
Ala Asn Leu His Leu Leu Leu Arg Asp Ala Ser Ile Phe Gly Lys
        195                 200                 205

GAG TGG GGA TTA TCA TCT TCA GAA ATT TCA ACA TTT TAT AAC CGT CAA        672
Glu Trp Gly Leu Ser Ser Ser Glu Ile Ser Thr Phe Tyr Asn Arg Gln
210                 215                 220

GTC GAA CGA GCA GGA GAT TAT TCC GAC CAT TGT GTG AAA TGG TAT AGC        720
Val Glu Arg Ala Gly Asp Tyr Ser Asp His Cys Val Lys Trp Tyr Ser
225                 230                 235                 240

ACA GGT CTA AAT AAC TTG AGG GGT ACA AAT GCC GAA AGT TGG GTA CGA        768
Thr Gly Leu Asn Asn Leu Arg Gly Thr Asn Ala Glu Ser Trp Val Arg
                245                 250                 255

TAT AAT CAA TTC CGT AGA GAC ATG ACT TTA ATG GTA CTA GAT TTA GTG        816
Tyr Asn Gln Phe Arg Arg Asp Met Thr Leu Met Val Leu Asp Leu Val
            260                 265                 270

GCA CTA TTT CCA AGC TAT GAT ACA CAA ATG TAT CCA ATT AAA ACT ACA        864
Ala Leu Phe Pro Ser Tyr Asp Thr Gln Met Tyr Pro Ile Lys Thr Thr
        275                 280                 285

GCC CAA CTT ACA AGA GAA GTA TAT ACA GAC GCA ATT GGG ACA GTA CAT        912
Ala Gln Leu Thr Arg Glu Val Tyr Thr Asp Ala Ile Gly Thr Val His
290                 295                 300

CCG CAT CCA AGT TTT ACA AGT ACG ACT TGG TAT AAT AAT AAT GCA CCT        960
Pro His Pro Ser Phe Thr Ser Thr Thr Trp Tyr Asn Asn Asn Ala Pro
305                 310                 315                 320

TCG TTC TCT GCC ATA GAG GCT GCT GTT GTT CGA AAC CCG CAT CTA CTC       1008
Ser Phe Ser Ala Ile Glu Ala Ala Val Val Arg Asn Pro His Leu Leu
                325                 330                 335

GAT TTT CTA GAA CAA GTT ACA ATT TAC AGC TTA TTA AGT CGA TGG AGT       1056
Asp Phe Leu Glu Gln Val Thr Ile Tyr Ser Leu Leu Ser Arg Trp Ser
            340                 345                 350
```

```
AAC ACT CAG TAT ATG AAT ATG TGG GGA GGA CAT AAA CTA GAA TTC CGA      1104
Asn Thr Gln Tyr Met Asn Met Trp Gly Gly His Lys Leu Glu Phe Arg
        355                 360                 365

ACA ATA GGA GGA ACG TTA AAT ATC TCA ACA CAA GGA TCT ACT AAT ACT      1152
Thr Ile Gly Gly Thr Leu Asn Ile Ser Thr Gln Gly Ser Thr Asn Thr
        370                 375                 380

TCT ATT AAT CCT GTA ACA TTA CCG TTC ACT TCT CGA GAC GTC TAT AGG      1200
Ser Ile Asn Pro Val Thr Leu Pro Phe Thr Ser Arg Asp Val Tyr Arg
385                 390                 395                 400

ACT GAA TCA TTG GCA GGG CTG AAT CTA TTT TTA ACT CAA CCT GTT AAT      1248
Thr Glu Ser Leu Ala Gly Leu Asn Leu Phe Leu Thr Gln Pro Val Asn
                405                 410                 415

GGA GTA CCT AGG GTT GAT TTT CAT TGG AAA TTC GTC ACA CAT CCG ATC      1296
Gly Val Pro Arg Val Asp Phe His Trp Lys Phe Val Thr His Pro Ile
        420                 425                 430

GCA TCT GAT AAT TTC TAT TAT CCA GGG TAT GCT GGA ATT GGG ACG CAA      1344
Ala Ser Asp Asn Phe Tyr Tyr Pro Gly Tyr Ala Gly Ile Gly Thr Gln
        435                 440                 445

TTA CAG GAT TCA GAA AAT GAA TTA CCA CCT GAA GCA ACA GGA CAG CCA      1392
Leu Gln Asp Ser Glu Asn Glu Leu Pro Pro Glu Ala Thr Gly Gln Pro
450                 455                 460

AAT TAC GAA TCT TAT AGT CAT AGA TTA TCT CAT ATA GGA CTC ATT TCA      1440
Asn Tyr Glu Ser Tyr Ser His Arg Leu Ser His Ile Gly Leu Ile Ser
465                 470                 475                 480

GCA TCA CAT GTG AAA GCA TTG GTA TAT TCT TGG ACG CAT CGT AGT GCA      1488
Ala Ser His Val Lys Ala Leu Val Tyr Ser Trp Thr His Arg Ser Ala
                485                 490                 495

GAT CGT ACA AAT ACA ATT GAG CCA AAT AGC ATT ACA CAA ATA CCA TTA      1536
Asp Arg Thr Asn Thr Ile Glu Pro Asn Ser Ile Thr Gln Ile Pro Leu
                500                 505                 510

GTA AAA GCT TTC AAT CTG TCT TCA GGT GCC GCT GTA GTG AGA GGA CCA      1584
Val Lys Ala Phe Asn Leu Ser Ser Gly Ala Ala Val Val Arg Gly Pro
        515                 520                 525

GGA TTT ACA GGT GGG GAT ATC TA                                       1607
Gly Phe Thr Gly Gly Asp Ile
        530                 535
```

(2) INFORMATION FOR SEQ ID NO:6:

(i) SEQUENCE CHARACTERISTICS:
        (A) LENGTH: 535 amino acids
        (B) TYPE: amino acid
        (D) TOPOLOGY: linear (ii) MOLECULE TYPE: protein (xi) SEQUENCE DESCRIPTION: SEQ ID NO:6:

```
Met Lys Leu Lys Asn Gln Asp Lys His Gln Ser Phe Ser Ser Asn Ala
 1               5                  10                  15

Lys Val Asp Lys Ile Ser Thr Ser Leu Lys Asn Glu Thr Asp Ile
                20                  25                  30

Glu Leu Gln Asn Ile Asn His Glu Asp Cys Leu Lys Met Ser Glu Tyr
                35                  40                  45

Glu Asn Val Glu Pro Phe Val Ser Ala Ser Thr Ile Gln Thr Gly Ile
        50                  55                  60

Gly Ile Ala Gly Lys Ile Leu Gly Thr Leu Gly Val Pro Phe Ala Gly
 65                  70                  75                  80

Gln Val Ala Ser Leu Tyr Ser Phe Ile Leu Gly Glu Leu Trp Pro Lys
                85                  90                  95

Gly Lys Asn Gln Trp Glu Ile Phe Met Glu His Val Glu Glu Ile Ile
```

-continued

```
                100                 105                 110
Asn Gln Lys Ile Ser Thr Tyr Ala Arg Asn Lys Ala Leu Thr Asp Leu
            115                 120                 125

Lys Gly Leu Gly Asp Ala Leu Ala Val Tyr His Asp Ser Leu Glu Ser
130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
            195                 200                 205

Glu Trp Gly Leu Ser Ser Ser Glu Ile Ser Thr Phe Tyr Asn Arg Gln
        210                 215                 220

Val Glu Arg Ala Gly Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
        275                 280                 285

Ala Gln Leu Thr Arg Glu Val Tyr Thr Asp Ala Ile Gly Thr Val His
        290                 295                 300

Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
        355                 360                 365

Thr Ile Gly Gly Thr Leu Asn Ile Ser Thr Gln Gly Ser Thr Asn Thr
370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
        435                 440                 445

Leu Gln Asp Ser Glu Asn Glu Leu Pro Pro Glu Ala Thr Gly Gln Pro
        450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525
```

```
Gly Phe Thr Gly Gly Asp Ile
    530                 535

(2) INFORMATION FOR SEQ ID NO:7:

(i) SEQUENCE CHARACTERISTICS:
        (A) LENGTH: 2159 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..2159

(xi) SEQUENCE DESCRIPTION: SEQ ID NO:7:

ATG AAG CTG AAG AAC CAA GAC AAG CAC CAA TCG TTC TCC AGC AAC GCG     48
Met Lys Leu Lys Asn Gln Asp Lys His Gln Ser Phe Ser Ser Asn Ala
 1               5                   10                  15

AAA GTG GAC AAG ATC AGC ACC GAC TCC CTG AAG AAC GAG ACC GAC ATC     96
Lys Val Asp Lys Ile Ser Thr Asp Ser Leu Lys Asn Glu Thr Asp Ile
             20                  25                  30

GAG CTC CAG AAC ATC AAC CAC GAA GAT TGC CTG AAG ATG TCC GAG TAC    144
Glu Leu Gln Asn Ile Asn His Glu Asp Cys Leu Lys Met Ser Glu Tyr
         35                  40                  45

GAG AAC GTG GAG CCG TTC GTG AGC GCC TCC ACC ATC CAG ACC GGC ATC    192
Glu Asn Val Glu Pro Phe Val Ser Ala Ser Thr Ile Gln Thr Gly Ile
     50                  55                  60

GGC ATC GCG GGC AAG ATC CTG GGT ACC CTG GGC GTG CCG TTT GCC GGC    240
Gly Ile Ala Gly Lys Ile Leu Gly Thr Leu Gly Val Pro Phe Ala Gly
 65                  70                  75                  80

CAA GTG GCT AGC CTG TAC AGC TTC ATC CTC GGC GAG CTG TGG CCT AAG    288
Gln Val Ala Ser Leu Tyr Ser Phe Ile Leu Gly Glu Leu Trp Pro Lys
                 85                  90                  95

GGC AAG AAC CAA TGG GAG ATC TTC ATG GAG CAC GTG GAG GAG ATC ATC    336
Gly Lys Asn Gln Trp Glu Ile Phe Met Glu His Val Glu Glu Ile Ile
            100                 105                 110

AAC CAG AAG ATT TCC ACC TAC GCC CGC AAC AAG GCC CTT ACC GAC CTG    384
Asn Gln Lys Ile Ser Thr Tyr Ala Arg Asn Lys Ala Leu Thr Asp Leu
        115                 120                 125

AAG GGC CTC GGC GAC GCC CTG GCT GTC TAC CAC GAC TCC CTG GAG AGC    432
Lys Gly Leu Gly Asp Ala Leu Ala Val Tyr His Asp Ser Leu Glu Ser
130                 135                 140

TGG GTG GGC AAC CGC AAC AAC ACG AGG GCC CGC AGC GTG GTG AAG AGC    480
Trp Val Gly Asn Arg Asn Asn Thr Arg Ala Arg Ser Val Val Lys Ser
145                 150                 155                 160

CAG TAC ATC GCC CTG GAG CTG ATG TTC GTG CAG AAG CTG CCG TCC TTC    528
Gln Tyr Ile Ala Leu Glu Leu Met Phe Val Gln Lys Leu Pro Ser Phe
                165                 170                 175

GCC GTG TCT GGT GAG GAG GTG CCC CTG CTG CCG ATC TAC GCC CAG GCC    576
Ala Val Ser Gly Glu Glu Val Pro Leu Leu Pro Ile Tyr Ala Gln Ala
            180                 185                 190

GCC AAC CTC CAC CTC CTG CTC CTG CGC GAC GCC AGC ATC TTC GGC AAG    624
Ala Asn Leu His Leu Leu Leu Leu Arg Asp Ala Ser Ile Phe Gly Lys
        195                 200                 205

GAG TGG GGC CTG TCC TCC AGC GAG ATC AGC ACG TTC TAC AAC AGG CAG    672
Glu Trp Gly Leu Ser Ser Ser Glu Ile Ser Thr Phe Tyr Asn Arg Gln
    210                 215                 220

GTG GAG CGC GCC GGC GAC TAC AGC GAC CAT TGC GTG AAG TGG TAC AGC    720
Val Glu Arg Ala Gly Asp Tyr Ser Asp His Cys Val Lys Trp Tyr Ser
```

```
               225                 230                 235                 240
ACC GGC CTG AAC AAC CTG AGG GGC ACC AAC GCC GAG AGC TGG GTC CGC              768
Thr Gly Leu Asn Asn Leu Arg Gly Thr Asn Ala Glu Ser Trp Val Arg
                    245                 250                 255

TAC AAT CAG TTC CGC CGC GAC ATG ACC CTG ATG GTG CTG GAC CTG GTG              816
Tyr Asn Gln Phe Arg Arg Asp Met Thr Leu Met Val Leu Asp Leu Val
            260                 265                 270

GCC CTG TTC CCG AGC TAC GAC ACC CAG ATG TAC CCG ATC AAG ACC ACC              864
Ala Leu Phe Pro Ser Tyr Asp Thr Gln Met Tyr Pro Ile Lys Thr Thr
        275                 280                 285

GCC CAG CTG ACC CGC GAG GTG TAC ACC GAC GCC ATT GGC ACC GTG CAC              912
Ala Gln Leu Thr Arg Glu Val Tyr Thr Asp Ala Ile Gly Thr Val His
    290                 295                 300

CCG CAC CCG AGC TTC ACG AGC ACC ACC TGG TAC AAC AAC AAC GCC CCA              960
Pro His Pro Ser Phe Thr Ser Thr Thr Trp Tyr Asn Asn Asn Ala Pro
305                 310                 315                 320

AGC TTC AGC GCC ATC GAG GCC GCC GTG GTG CGC AAC CCC CAC CTC CTG             1008
Ser Phe Ser Ala Ile Glu Ala Ala Val Val Arg Asn Pro His Leu Leu
                    325                 330                 335

GAC TTC CTG GAG CAG GTG ACC ATC TAC AGC CTG CTG AGC CGG TGG AGC             1056
Asp Phe Leu Glu Gln Val Thr Ile Tyr Ser Leu Leu Ser Arg Trp Ser
            340                 345                 350

AAC ACG CAG TAC ATG AAC ATG TGG GGC GGC CAT AAG CTG GAG TTC AGG             1104
Asn Thr Gln Tyr Met Asn Met Trp Gly Gly His Lys Leu Glu Phe Arg
        355                 360                 365

ACC ATC GGC GGC ACC CTC AAC ATC AGC ACC CAA GGC AGC ACC AAC ACC             1152
Thr Ile Gly Gly Thr Leu Asn Ile Ser Thr Gln Gly Ser Thr Asn Thr
    370                 375                 380

AGC ATC AAC CCG GTC ACC CTG CCC TTC ACC AGC CGC GAC GTG TAC CGC             1200
Ser Ile Asn Pro Val Thr Leu Pro Phe Thr Ser Arg Asp Val Tyr Arg
385                 390                 395                 400

ACC GAG AGC CTG GCC GGC CTG AAC CTG TTC CTG ACC CAG CCC GTG AAC             1248
Thr Glu Ser Leu Ala Gly Leu Asn Leu Phe Leu Thr Gln Pro Val Asn
                    405                 410                 415

GGC GTG CCC CGC GTG GAC TTT CAC TGG AAG TTC GTG ACC CAC CCG ATC             1296
Gly Val Pro Arg Val Asp Phe His Trp Lys Phe Val Thr His Pro Ile
            420                 425                 430

GCC AGC GAC AAC TTC TAC TAC CCC GGC TAC GCT GGC ATT GGC ACC CAA             1344
Ala Ser Asp Asn Phe Tyr Tyr Pro Gly Tyr Ala Gly Ile Gly Thr Gln
        435                 440                 445

CTC CAG GAC AGC GAG AAC GAG CTG CCG CCC GAG GCC ACC GGT CAG CCG             1392
Leu Gln Asp Ser Glu Asn Glu Leu Pro Pro Glu Ala Thr Gly Gln Pro
    450                 455                 460

AAC TAC GAG AGC TAC AGC CAC CGC CTG AGC CAC ATC GGC CTG ATC TCC             1440
Asn Tyr Glu Ser Tyr Ser His Arg Leu Ser His Ile Gly Leu Ile Ser
465                 470                 475                 480

GCC TCC CAC GTG AAG GCC CTG GTG TAC TCC TGG ACC CAC CGC AGC GCC             1488
Ala Ser His Val Lys Ala Leu Val Tyr Ser Trp Thr His Arg Ser Ala
                    485                 490                 495

GAC CGC ACC AAC ACC ATC GAG CCG AAC AGC ATC ACG CAG ATC CCG CTG             1536
Asp Arg Thr Asn Thr Ile Glu Pro Asn Ser Ile Thr Gln Ile Pro Leu
            500                 505                 510

GTG AAG GCC TTC AAC CTG AGC TCC GGT GCT GCA GTG GTG CGC GGT CCA             1584
Val Lys Ala Phe Asn Leu Ser Ser Gly Ala Ala Val Val Arg Gly Pro
        515                 520                 525

GGC TTC ACA GGC GGC GAC ATC CTG CGC AGG ACC AAC ACC GGC ACC TTC             1632
Gly Phe Thr Gly Gly Asp Ile Leu Arg Arg Thr Asn Thr Gly Thr Phe
    530                 535                 540

GGC GAC ATC CGC GTG AAC ATC AAC CCC CCG TTC GCC CAG CGC TAC AGG             1680
```

-continued

```
Gly Asp Ile Arg Val Asn Ile Asn Pro Pro Phe Ala Gln Arg Tyr Arg
545                 550                 555                 560

GTG AGG ATC AGG TAC GCC AGC ACC ACC GAC CTC CAG TTC CAC ACC AGC    1728
Val Arg Ile Arg Tyr Ala Ser Thr Thr Asp Leu Gln Phe His Thr Ser
                565                 570                 575

ATC AAC GGC AAG GCC ATC AAC CAG GGC AAC TTC AGC GCC ACC ATG AAC    1776
Ile Asn Gly Lys Ala Ile Asn Gln Gly Asn Phe Ser Ala Thr Met Asn
                580                 585                 590

CGC GGT GAG GAC CTG GAC TAC AAG ACC TTC CGC ACC GTG GGC TTC ACC    1824
Arg Gly Glu Asp Leu Asp Tyr Lys Thr Phe Arg Thr Val Gly Phe Thr
                595                 600                 605

ACC CCG TTC AGC TTC CTG GAC GTG CAG AGC ACC TTC ACC ATC GGC GCC    1872
Thr Pro Phe Ser Phe Leu Asp Val Gln Ser Thr Phe Thr Ile Gly Ala
        610                 615                 620

TGG AAC TTC AGC AGC GGC AAC GAG GTG TAC ATC GAC CGC ATC GAG TTC    1920
Trp Asn Phe Ser Ser Gly Asn Glu Val Tyr Ile Asp Arg Ile Glu Phe
625                 630                 635                 640

GTG CCC GTG GAG GTG ACC TAC GAG GCC GAG TAC GAC TTC GAG AAG GCC    1968
Val Pro Val Glu Val Thr Tyr Glu Ala Glu Tyr Asp Phe Glu Lys Ala
                645                 650                 655

CAG GAG AAG GTC ACC GCC CTG TTC ACC AGC ACC AAC CCG CGC GGC CTG    2016
Gln Glu Lys Val Thr Ala Leu Phe Thr Ser Thr Asn Pro Arg Gly Leu
                660                 665                 670

AAG ACC GAC GTG CAG GAC TAC CAC ATC GAC CAG GTG AGC AAC TTG GTG    2064
Lys Thr Asp Val Gln Asp Tyr His Ile Asp Gln Val Ser Asn Leu Val
                675                 680                 685

GAG TCC CTG AGC GAC GAG TTC TAC CTG GAC GAG AAG CGC GAG CTG TTC    2112
Glu Ser Leu Ser Asp Glu Phe Tyr Leu Asp Glu Lys Arg Glu Leu Phe
        690                 695                 700

GAG ATC GTG AAG TAC GCC AAG CAG CTG CAC ATC GAG CGC AAC ATG TA     2159
Glu Ile Val Lys Tyr Ala Lys Gln Leu His Ile Glu Arg Asn Met
705                 710                 715                 720
```

(2) INFORMATION FOR SEQ ID NO:8:

(i) SEQUENCE CHARACTERISTICS:
        (A) LENGTH: 719 amino acids
        (B) TYPE: amino acid
        (D) TOPOLOGY: linear (ii) MOLECULE TYPE: protein (xi) SEQUENCE DESCRIPTION: SEQ ID NO:8:

```
Met Lys Leu Lys Asn Gln Asp Lys His Gln Ser Phe Ser Ser Asn Ala
1               5                   10                  15

Lys Val Asp Lys Ile Ser Thr Asp Ser Leu Lys Asn Glu Thr Asp Ile
            20                  25                  30

Glu Leu Gln Asn Ile Asn His Glu Asp Cys Leu Lys Met Ser Glu Tyr
        35                  40                  45

Glu Asn Val Glu Pro Phe Val Ser Ala Ser Thr Ile Gln Thr Gly Ile
    50                  55                  60

Gly Ile Ala Gly Lys Ile Leu Gly Thr Leu Gly Val Pro Phe Ala Gly
65              70                  75                  80

Gln Val Ala Ser Leu Tyr Ser Phe Ile Leu Gly Glu Leu Trp Pro Lys
                85                  90                  95

Gly Lys Asn Gln Trp Glu Ile Phe Met Glu His Val Glu Glu Ile Ile
            100                 105                 110

Asn Gln Lys Ile Ser Thr Tyr Ala Arg Asn Lys Ala Leu Thr Asp Leu
        115                 120                 125
```

-continued

```
Lys Gly Leu Gly Asp Ala Leu Ala Val Tyr His Asp Ser Leu Glu Ser
    130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
                165                 170                 175

Ala Val Ser Gly Glu Glu Val Pro Leu Leu Pro Ile Tyr Ala Gln Ala
            180                 185                 190

Ala Asn Leu His Leu Leu Leu Arg Asp Ala Ser Ile Phe Gly Lys
            195                 200                 205

Glu Trp Gly Leu Ser Ser Glu Ile Ser Thr Phe Tyr Asn Arg Gln
    210                 215                 220

Val Glu Arg Ala Gly Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
                245                 250                 255

Tyr Asn Gln Phe Arg Arg Asp Met Thr Leu Met Val Leu Asp Leu Val
                260                 265                 270

Ala Leu Phe Pro Ser Tyr Asp Thr Gln Met Tyr Pro Ile Lys Thr Thr
            275                 280                 285

Ala Gln Leu Thr Arg Glu Val Tyr Thr Asp Ala Ile Gly Thr Val His
    290                 295                 300

Pro His Pro Ser Phe Thr Ser Thr Thr Trp Tyr Asn Asn Asn Ala Pro
305                 310                 315                 320

Ser Phe Ser Ala Ile Glu Ala Ala Val Val Arg Asn Pro His Leu Leu
                325                 330                 335

Asp Phe Leu Glu Gln Val Thr Ile Tyr Ser Leu Leu Ser Arg Trp Ser
                340                 345                 350

Asn Thr Gln Tyr Met Asn Met Trp Gly Gly His Lys Leu Glu Phe Arg
            355                 360                 365

Thr Ile Gly Gly Thr Leu Asn Ile Ser Thr Gln Gly Ser Thr Asn Thr
    370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
    435                 440                 445

Leu Gln Asp Ser Glu Asn Glu Leu Pro Pro Glu Ala Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
            515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
```

```
545                 550                 555                 560
Val Arg Ile Arg Tyr Ala Ser Thr Thr Asp Leu Gln Phe His Thr Ser
            565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
            595                 600                 605

Thr Pro Phe Ser Phe Leu Asp Val Gln Ser Thr Phe Thr Ile Gly Ala
            610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
            645                 650                 655

Gln Glu Lys Val Thr Ala Leu Phe Thr Ser Thr Asn Pro Arg Gly Leu
            660                 665                 670

Lys Thr Asp Val Gln Asp Tyr His Ile Asp Gln Val Ser Asn Leu Val
            675                 680                 685

Glu Ser Leu Ser Asp Glu Phe Tyr Leu Asp Glu Lys Arg Glu Leu Phe
            690                 695                 700

Glu Ile Val Lys Tyr Ala Lys Gln Leu His Ile Glu Arg Asn Met
705                 710                 715

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: both
        (D) TOPOLOGY: linear (xi) SEQUENCE DESCRIPTION: SEQ ID NO:9:

CCTAGATATC TCACTCA                                                              17

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: both
        (D) TOPOLOGY: linear (xi) SEQUENCE DESCRIPTION: SEQ ID NO:10:

TATGAGTGAG ATATCTAGGA GCT                                                       23
```